US009284573B2

(12) United States Patent
Meade et al.

(10) Patent No.: US 9,284,573 B2
(45) Date of Patent: Mar. 15, 2016

(54) MODIFIED CRY1CA INSECTICIAL CRY PROTEINS

(75) Inventors: Thomas Meade, Zionsville, IN (US); Stephanie L. Burton, Indianapolis, IN (US); Kenneth Narva, Zionsville, IN (US); Aaron T. Woosley, Fishers, IN (US); Timothy D. Hey, Zionsville, IN (US); Ignacio M. Larrinua, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 733 days.

(21) Appl. No.: 13/516,622

(22) PCT Filed: Dec. 16, 2010

(86) PCT No.: PCT/US2010/060826
§ 371 (c)(1),
(2), (4) Date: Oct. 10, 2012

(87) PCT Pub. No.: WO2011/084627
PCT Pub. Date: Jul. 14, 2011

(65) Prior Publication Data
US 2013/0025006 A1    Jan. 24, 2013

Related U.S. Application Data

(60) Provisional application No. 61/284,275, filed on Dec. 16, 2009.

(51) Int. Cl.
A01P 7/04      (2006.01)
C12N 5/10      (2006.01)
A01H 5/00      (2006.01)
C07K 19/00     (2006.01)
A01N 37/18     (2006.01)
C12N 15/82     (2006.01)
C07K 14/325    (2006.01)

(52) U.S. Cl.
CPC .......... C12N 15/8286 (2013.01); C07K 14/325 (2013.01)

(58) Field of Classification Search
None
See application file for complete search history.

(56) References Cited

U.S. PATENT DOCUMENTS 5,380,831 A    1/1995  Adang et al.
6,156,573 A   12/2000  Malvar et al.
2003/0101482 A1*  5/2003  Baum et al. ............. 800/279
2006/0288448 A1  12/2006  Abad et al.

FOREIGN PATENT DOCUMENTS

FR      2795739        1/2001
WO      WO 95/60730 A  3/1995
WO      WO 95/30752 A1 11/1995
WO      WO 98/15567 A3  4/1998
WO      WO 03/082910 A1 10/2003

OTHER PUBLICATIONS

Aguiar et al. A recombinant truncated Cry1Ca protein is toxic to lepidopteran insects and forms large cuboidal crystals in insect cells. Curr Microbiol. 53:287-92. Oct. 2006.*
Accession Q58FMO. Apr. 26, 2005. (alignment of amino acids 1-619 of SEQ ID No. 1 ).*
Accession Q58FMO. Apr. 26, 2005. (alignment of amino acids 28-619 of SEQ ID No. 1 ).*
Ruud A. De Maagd, Domain III Substituttion in *Bacillus thuringiensis* Delta-Endotoxin Cry 1A(b) Results in Superior Toxicity for *Spodoptera exigua* and Altered Membrane Protein Recognition; Applied and Environmental Microbiology, vol. 62, pp. 1537-1543.
Song et al. Carboxy-terminal half of Cry1C can help vegetative insecticidal protein to form inclusion bodies in the mother cell of *Bacillus thuringiensis*. Appl Microbiol Biotechnol (2008) 80:647-654, especially p. 648, col 1, para 3 to col 2, para 2 and the abstract.
Gatehouse. Biotechnological Prospects for Engineering Insect-Resistant Plants. Plant Physiology Mar. 2008 vol. 146, pp. 881-887, especially p. 883, col 2, para 2.
Bosch D et al: "Recombinant *Bacillus thuringiensis* Crystal Proteins with New Properties: Possibilities for Resistance Management" BIO/TECHNOLOGY, vol. 12, Sep. 1994, pp. 915-918, XP008019082 cited in the application, the whole document.
De Maagd Ruud A et al: "Identification of *Bacillus thuringiensis* delta-endotoxin CryIC domain III amino acid residues involved in insect specificity." Applied and Environmental Microbiology, vol. 65, No. 10, Oct. 1999, pp. 4369-4374, XP002246497 ISSN: 0099-2240, p. 4372; table 2.
Ballester V et al: "Role of *Bacillus thuringiensis* toxin domains in toxicity and receptor binding in the diamondback moth." Applied And Environmental Microbiology, vol. 65, No. 5, May 1999, pp. 1900-1903, XP002209206 ISSN: 0099-2240, the whole document.
Soberton, Mario, et al.; Engineering Modified Bt Toxins to Counter Insect Resistance, Science, vol. 318, pp. 1640-1642, Dec. 7, 2007.

* cited by examiner

Primary Examiner — Christian Fronda
(74) Attorney, Agent, or Firm — Ronald S. Maciak; Faegre Baker Daniels LLP

(57) ABSTRACT

The present invention includes modified, insecticidal B.t. Cry1Ca proteins, including the proteins designated herein as DIG-109 and DIG-152, as well as variants of DIG-109 and DIG-152, nucleic acids encoding these proteins, methods of controlling pests using the proteins, methods of producing the proteins in transgenic host cells, and transgenic plants that produce the proteins. The DIG-109 and DIG-152 proteins comprise chimeric peptides composed of a core toxin segment of B.t. Cry1Ca and a Cry1Ab protoxin segment. Insecticidally active variants of the DIG-109 and DIG-152 proteins are also described.

12 Claims, 1 Drawing Sheet

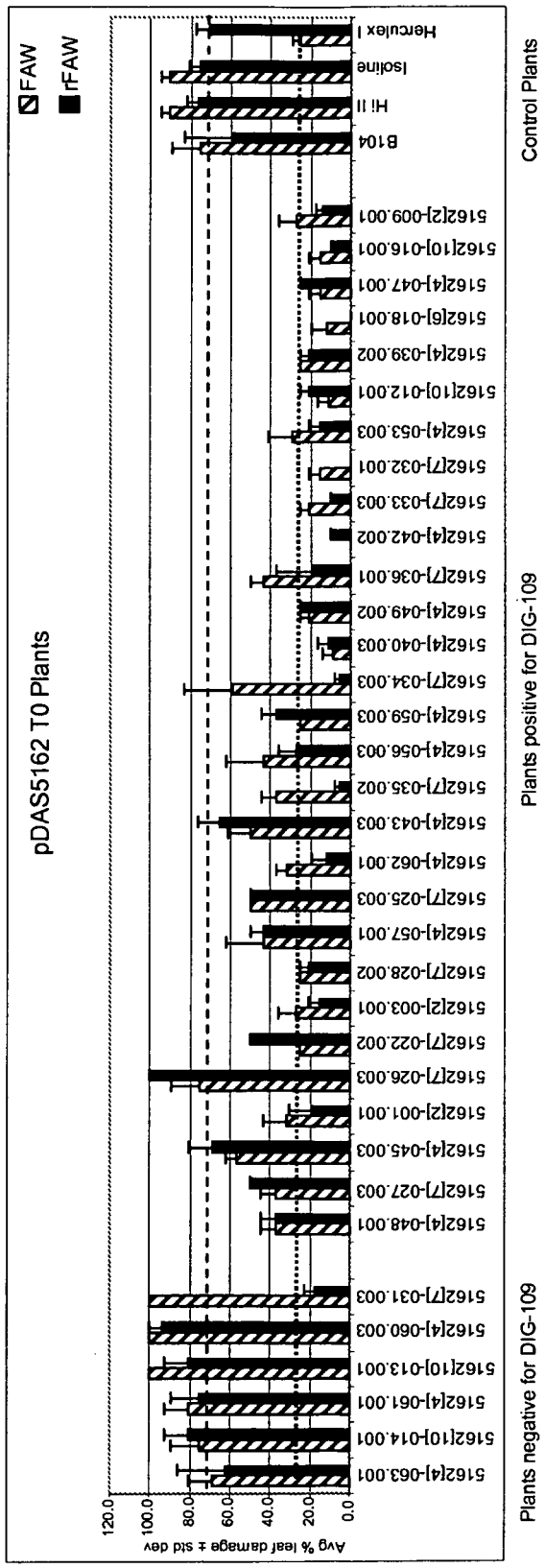
Feeding damage ratings of maize leaf pieces challenged in vitro with neonate larvae of fall armyworm (FAW) and fall armyworm resistant to Cry1F (rFAW). Transgenic T0 plants selected after transformation with pDAS5162 were divided into two groups by immunoblot screening using antibody DIG152R

SEQUENCE LISTING

<160> NUMBER OF SEQ ID NOS: 36

<210> SEQ ID NO 1
<211> LENGTH: 619
<212> TYPE: PRT
<213> ORGANISM: Artificial Sequence
<220> FEATURE:
<223> OTHER INFORMATION: Derived from Cry1Ca3

<400> SEQUENCE: 1

```
Met Asp Asn Asn Pro Asn Ile Asn Glu Cys Ile Pro Tyr Asn Cys Leu
1               5                   10                  15

Ser Asn Pro Glu Glu Val Leu Leu Asp Gly Glu Arg Ile Ser Thr Gly
            20                  25                  30

Asn Ser Ser Ile Asp Ile Ser Leu Ser Leu Val Gln Phe Leu Val Ser
        35                  40                  45

Asn Phe Val Pro Gly Gly Gly Phe Leu Val Gly Leu Ile Asp Phe Val
    50                  55                  60

Trp Gly Ile Val Gly Pro Ser Gln Trp Asp Ala Phe Leu Val Gln Ile
65                  70                  75                  80

Glu Gln Leu Ile Asn Glu Arg Ile Ala Glu Phe Ala Arg Asn Ala Ala
                85                  90                  95

Ile Ala Asn Leu Glu Gly Leu Gly Asn Asn Phe Asn Ile Tyr Val Glu
            100                 105                 110

Ala Phe Lys Glu Trp Glu Glu Asp Pro Lys Asn Pro Ala Thr Arg Thr
        115                 120                 125

Arg Val Ile Asp Arg Phe Arg Ile Leu Asp Gly Leu Leu Glu Arg Asp
    130                 135                 140

Ile Pro Ser Phe Arg Ile Ser Gly Phe Glu Val Pro Leu Leu Ser Val
145                 150                 155                 160

Tyr Ala Gln Ala Ala Asn Leu His Leu Ala Ile Leu Arg Asp Ser Val
                165                 170                 175

Ile Phe Gly Glu Arg Trp Gly Leu Thr Thr Ile Asn Val Asn Glu Asn
            180                 185                 190

Tyr Asn Arg Leu Ile Arg His Ile Asp Glu Tyr Ala Asp His Cys Ala
        195                 200                 205

Asn Thr Tyr Asn Arg Gly Leu Asn Asn Leu Pro Lys Ser Thr Tyr Gln
    210                 215                 220

Asp Trp Ile Thr Tyr Asn Arg Leu Arg Arg Asp Leu Thr Leu Thr Val
225                 230                 235                 240

Leu Asp Ile Ala Ala Phe Phe Pro Asn Tyr Asp Asn Arg Arg Tyr Pro
                245                 250                 255

Ile Gln Pro Val Gly Gln Leu Thr Arg Glu Val Tyr Thr Asp Pro Leu
            260                 265                 270

Ile Asn Phe Asn Pro Gln Leu Gln Ser Val Ala Gln Leu Pro Thr Phe
        275                 280                 285

Asn Val Met Glu Asn Ser Ala Ile Arg Asn Pro His Leu Phe Asp Ile
    290                 295                 300

Leu Asn Asn Leu Thr Ile Phe Thr Asp Trp Phe Ser Val Gly Arg Asn
305                 310                 315                 320

Phe Tyr Trp Gly Gly His Arg Val Ile Ser Ser Leu Ile Gly Gly Gly
                325                 330                 335

Asn Ile Thr Ser Pro Ile Tyr Gly Arg Glu Ala Asn Gln Glu Pro Pro
            340                 345                 350

Arg Ser Phe Thr Phe Asn Gly Pro Val Phe Arg Thr Leu Ser Asn Pro
```

```
                    355                 360                 365
Thr Leu Arg Leu Leu Gln Gln Pro Trp Pro Ala Pro Pro Phe Asn Leu
    370                 375                 380

Arg Gly Val Glu Gly Val Glu Phe Ser Thr Pro Thr Asn Ser Phe Thr
385                 390                 395                 400

Tyr Arg Gly Arg Gly Thr Val Asp Ser Leu Thr Glu Leu Pro Pro Glu
                405                 410                 415

Asp Asn Ser Val Pro Pro Arg Glu Gly Tyr Ser His Arg Leu Cys His
            420                 425                 430

Ala Thr Phe Val Gln Arg Ser Gly Thr Pro Phe Leu Thr Thr Gly Val
        435                 440                 445

Val Phe Ser Trp Thr His Arg Ser Ala Thr Leu Thr Asn Thr Ile Asp
    450                 455                 460

Pro Glu Arg Ile Asn Gln Ile Pro Leu Val Lys Gly Phe Arg Val Trp
465                 470                 475                 480

Gly Gly Thr Ser Val Ile Thr Gly Pro Gly Phe Thr Gly Gly Asp Ile
                485                 490                 495

Leu Arg Arg Asn Thr Phe Gly Asp Phe Val Ser Leu Gln Val Asn Ile
            500                 505                 510

Asn Ser Pro Ile Thr Gln Arg Tyr Arg Leu Arg Phe Arg Tyr Ala Ser
        515                 520                 525

Ser Arg Asp Ala Arg Val Ile Val Leu Thr Gly Ala Ala Ser Thr Gly
    530                 535                 540

Val Gly Gly Gln Val Ser Val Asn Met Pro Leu Gln Lys Thr Met Glu
545                 550                 555                 560

Ile Gly Glu Asn Leu Thr Ser Arg Thr Phe Arg Tyr Thr Asp Phe Ser
                565                 570                 575

Asn Pro Phe Ser Phe Arg Ala Asn Pro Asp Ile Ile Gly Ile Ser Glu
            580                 585                 590

Gln Pro Leu Phe Gly Ala Gly Ser Ile Ser Ser Gly Glu Leu Tyr Ile
        595                 600                 605

Asp Lys Ile Glu Ile Ile Leu Ala Asp Ala Thr
    610                 615

<210> SEQ ID NO 2
<211> LENGTH: 545
<212> TYPE: PRT
<213> ORGANISM: Artificial Sequence
<220> FEATURE:
<223> OTHER INFORMATION: Derived from Cry1Ab

<400> SEQUENCE: 2

Phe Glu Ala Glu Ser Asp Leu Glu Arg Ala Gln Lys Ala Val Asn Ala
1               5                   10                  15

Leu Phe Thr Ser Ser Asn Gln Ile Gly Leu Lys Thr Asp Val Thr Asp
            20                  25                  30

Tyr His Ile Asp Arg Val Ser Asn Leu Val Glu Cys Leu Ser Asp Glu
        35                  40                  45

Phe Cys Leu Asp Glu Lys Lys Glu Leu Ser Glu Lys Val Lys His Ala
    50                  55                  60

Lys Arg Leu Ser Asp Glu Arg Asn Leu Leu Gln Asp Pro Asn Phe Arg
65                  70                  75                  80

Gly Ile Asn Arg Gln Leu Asp Arg Gly Trp Arg Gly Ser Thr Asp Ile
                85                  90                  95

Thr Ile Gln Gly Gly Asp Asp Val Phe Lys Glu Asn Tyr Val Thr Leu
```

```
                100                 105                 110
Leu Gly Thr Phe Asp Glu Cys Tyr Pro Thr Tyr Leu Tyr Gln Lys Ile
            115                 120                 125
Asp Glu Ser Lys Leu Lys Ala Tyr Thr Arg Tyr Gln Leu Arg Gly Tyr
            130                 135                 140
Ile Glu Asp Ser Gln Asp Leu Glu Ile Tyr Leu Ile Arg Tyr Asn Ala
145                 150                 155                 160
Lys His Glu Thr Val Asn Val Pro Gly Thr Gly Ser Leu Trp Pro Leu
                165                 170                 175
Ser Ala Pro Ser Pro Ile Gly Lys Cys Ala His His Ser His His Phe
            180                 185                 190
Ser Leu Asp Ile Asp Val Gly Cys Thr Asp Leu Asn Glu Asp Leu Gly
            195                 200                 205
Val Trp Val Ile Phe Lys Ile Lys Thr Gln Asp Gly His Ala Arg Leu
210                 215                 220
Gly Asn Leu Glu Phe Leu Glu Glu Lys Pro Leu Val Gly Glu Ala Leu
225                 230                 235                 240
Ala Arg Val Lys Arg Ala Glu Lys Lys Trp Arg Asp Lys Arg Glu Lys
                245                 250                 255
Leu Glu Trp Glu Thr Asn Ile Val Tyr Lys Glu Ala Lys Glu Ser Val
                260                 265                 270
Asp Ala Leu Phe Val Asn Ser Gln Tyr Asp Arg Leu Gln Ala Asp Thr
            275                 280                 285
Asn Ile Ala Met Ile His Ala Ala Asp Lys Arg Val His Ser Ile Arg
            290                 295                 300
Glu Ala Tyr Leu Pro Glu Leu Ser Val Ile Pro Gly Val Asn Ala Ala
305                 310                 315                 320
Ile Phe Glu Glu Leu Glu Gly Arg Ile Phe Thr Ala Phe Ser Leu Tyr
                325                 330                 335
Asp Ala Arg Asn Val Ile Lys Asn Gly Asp Phe Asn Asn Gly Leu Ser
            340                 345                 350
Cys Trp Asn Val Lys Gly His Val Asp Val Glu Glu Gln Asn Asn His
            355                 360                 365
Arg Ser Val Leu Val Val Pro Glu Trp Glu Ala Glu Val Ser Gln Glu
            370                 375                 380
Val Arg Val Cys Pro Gly Arg Gly Tyr Ile Leu Arg Val Thr Ala Tyr
385                 390                 395                 400
Lys Glu Gly Tyr Gly Glu Gly Cys Val Thr Ile His Glu Ile Glu Asn
                405                 410                 415
Asn Thr Asp Glu Leu Lys Phe Ser Asn Cys Val Glu Glu Glu Val Tyr
            420                 425                 430
Pro Asn Asn Thr Val Thr Cys Asn Asp Tyr Thr Ala Thr Gln Glu Glu
            435                 440                 445
Tyr Glu Gly Thr Tyr Thr Ser Arg Asn Arg Gly Tyr Asp Gly Ala Tyr
            450                 455                 460
Glu Ser Asn Ser Ser Val Pro Ala Asp Tyr Ala Ser Ala Tyr Glu Glu
465                 470                 475                 480
Lys Ala Tyr Thr Asp Gly Arg Arg Asp Asn Pro Cys Glu Ser Asn Arg
                485                 490                 495
Gly Tyr Gly Asp Tyr Thr Pro Leu Pro Ala Gly Tyr Val Thr Lys Glu
                500                 505                 510
Leu Glu Tyr Phe Pro Glu Thr Asp Lys Val Trp Ile Glu Ile Gly Glu
            515                 520                 525
```

```
Thr Glu Gly Thr Phe Ile Val Asp Ser Val Glu Leu Leu Met Glu
        530                 535                 540
Glu
545

<210> SEQ ID NO 3
<211> LENGTH: 1164
<212> TYPE: PRT
<213> ORGANISM: Artificial Sequence
<220> FEATURE:
<223> OTHER INFORMATION: DIG-152 Chimeric protein

<400> SEQUENCE: 3

Met Asp Asn Asn Pro Asn Ile Asn Glu Cys Ile Pro Tyr Asn Cys Leu
  1               5                  10                  15

Ser Asn Pro Glu Glu Val Leu Leu Asp Gly Glu Arg Ile Ser Thr Gly
             20                  25                  30

Asn Ser Ser Ile Asp Ile Ser Leu Ser Leu Val Gln Phe Leu Val Ser
         35                  40                  45

Asn Phe Val Pro Gly Gly Gly Phe Leu Val Gly Leu Ile Asp Phe Val
     50                  55                  60

Trp Gly Ile Val Gly Pro Ser Gln Trp Asp Ala Phe Leu Val Gln Ile
 65                  70                  75                  80

Glu Gln Leu Ile Asn Glu Arg Ile Ala Glu Phe Ala Arg Asn Ala Ala
                 85                  90                  95

Ile Ala Asn Leu Glu Gly Leu Gly Asn Asn Phe Asn Ile Tyr Val Glu
            100                 105                 110

Ala Phe Lys Glu Trp Glu Glu Asp Pro Lys Asn Pro Ala Thr Arg Thr
        115                 120                 125

Arg Val Ile Asp Arg Phe Arg Ile Leu Asp Gly Leu Leu Glu Arg Asp
    130                 135                 140

Ile Pro Ser Phe Arg Ile Ser Gly Phe Glu Val Pro Leu Leu Ser Val
145                 150                 155                 160

Tyr Ala Gln Ala Ala Asn Leu His Leu Ala Ile Leu Arg Asp Ser Val
                165                 170                 175

Ile Phe Gly Glu Arg Trp Gly Leu Thr Thr Ile Asn Val Asn Glu Asn
            180                 185                 190

Tyr Asn Arg Leu Ile Arg His Ile Asp Glu Tyr Ala Asp His Cys Ala
        195                 200                 205

Asn Thr Tyr Asn Arg Gly Leu Asn Asn Leu Pro Lys Ser Thr Tyr Gln
    210                 215                 220

Asp Trp Ile Thr Tyr Asn Arg Leu Arg Arg Asp Leu Thr Leu Thr Val
225                 230                 235                 240

Leu Asp Ile Ala Ala Phe Phe Pro Asn Tyr Asp Asn Arg Arg Tyr Pro
                245                 250                 255

Ile Gln Pro Val Gly Gln Leu Thr Arg Glu Val Tyr Thr Asp Pro Leu
            260                 265                 270

Ile Asn Phe Asn Pro Gln Leu Gln Ser Val Ala Gln Leu Pro Thr Phe
        275                 280                 285

Asn Val Met Glu Asn Ser Ala Ile Arg Asn Pro His Leu Phe Asp Ile
    290                 295                 300

Leu Asn Asn Leu Thr Ile Phe Thr Asp Trp Phe Ser Val Gly Arg Asn
305                 310                 315                 320

Phe Tyr Trp Gly Gly His Arg Val Ile Ser Ser Leu Ile Gly Gly Gly
                325                 330                 335
```

```
Asn Ile Thr Ser Pro Ile Tyr Gly Arg Glu Ala Asn Gln Glu Pro Pro
            340                 345                 350

Arg Ser Phe Thr Phe Asn Gly Pro Val Phe Arg Thr Leu Ser Asn Pro
            355                 360                 365

Thr Leu Arg Leu Leu Gln Gln Pro Trp Pro Ala Pro Pro Phe Asn Leu
        370                 375                 380

Arg Gly Val Glu Gly Val Glu Phe Ser Thr Pro Thr Asn Ser Phe Thr
385                 390                 395                 400

Tyr Arg Gly Arg Gly Thr Val Asp Ser Leu Thr Glu Leu Pro Pro Glu
                405                 410                 415

Asp Asn Ser Val Pro Pro Arg Glu Gly Tyr Ser His Arg Leu Cys His
            420                 425                 430

Ala Thr Phe Val Gln Arg Ser Gly Thr Pro Phe Leu Thr Thr Gly Val
            435                 440                 445

Val Phe Ser Trp Thr His Arg Ser Ala Thr Leu Thr Asn Thr Ile Asp
        450                 455                 460

Pro Glu Arg Ile Asn Gln Ile Pro Leu Val Lys Gly Phe Arg Val Trp
465                 470                 475                 480

Gly Gly Thr Ser Val Ile Thr Gly Pro Gly Phe Thr Gly Gly Asp Ile
                485                 490                 495

Leu Arg Arg Asn Thr Phe Gly Asp Phe Val Ser Leu Gln Val Asn Ile
            500                 505                 510

Asn Ser Pro Ile Thr Gln Arg Tyr Arg Leu Arg Phe Arg Tyr Ala Ser
            515                 520                 525

Ser Arg Asp Ala Arg Val Ile Val Leu Thr Gly Ala Ala Ser Thr Gly
        530                 535                 540

Val Gly Gly Gln Val Ser Val Asn Met Pro Leu Gln Lys Thr Met Glu
545                 550                 555                 560

Ile Gly Glu Asn Leu Thr Ser Arg Thr Phe Arg Tyr Thr Asp Phe Ser
                565                 570                 575

Asn Pro Phe Ser Phe Arg Ala Asn Pro Asp Ile Ile Gly Ile Ser Glu
            580                 585                 590

Gln Pro Leu Phe Gly Ala Gly Ser Ile Ser Ser Gly Glu Leu Tyr Ile
        595                 600                 605

Asp Lys Ile Glu Ile Ile Leu Ala Asp Ala Thr Phe Glu Ala Glu Ser
            610                 615                 620

Asp Leu Glu Arg Ala Gln Lys Ala Val Asn Ala Leu Phe Thr Ser Ser
625                 630                 635                 640

Asn Gln Ile Gly Leu Lys Thr Asp Val Thr Asp Tyr His Ile Asp Arg
                645                 650                 655

Val Ser Asn Leu Val Glu Cys Leu Ser Asp Glu Phe Cys Leu Asp Glu
            660                 665                 670

Lys Lys Glu Leu Ser Glu Lys Val Lys His Ala Lys Arg Leu Ser Asp
            675                 680                 685

Glu Arg Asn Leu Leu Gln Asp Pro Asn Phe Arg Gly Ile Asn Arg Gln
        690                 695                 700

Leu Asp Arg Gly Trp Arg Gly Ser Thr Asp Ile Thr Ile Gln Gly Gly
705                 710                 715                 720

Asp Asp Val Phe Lys Glu Asn Tyr Val Thr Leu Leu Gly Thr Phe Asp
                725                 730                 735

Glu Cys Tyr Pro Thr Tyr Leu Tyr Gln Lys Ile Asp Glu Ser Lys Leu
            740                 745                 750
```

```
Lys Ala Tyr Thr Arg Tyr Gln Leu Arg Gly Tyr Ile Glu Asp Ser Gln
            755                 760                 765
Asp Leu Glu Ile Tyr Leu Ile Arg Tyr Asn Ala Lys His Glu Thr Val
            770                 775                 780
Asn Val Pro Gly Thr Gly Ser Leu Trp Pro Leu Ser Ala Pro Ser Pro
785                 790                 795                 800
Ile Gly Lys Cys Ala His His Ser His His Phe Ser Leu Asp Ile Asp
                805                 810                 815
Val Gly Cys Thr Asp Leu Asn Glu Asp Leu Gly Val Trp Val Ile Phe
            820                 825                 830
Lys Ile Lys Thr Gln Asp Gly His Ala Arg Leu Gly Asn Leu Glu Phe
            835                 840                 845
Leu Glu Glu Lys Pro Leu Val Gly Glu Ala Leu Ala Arg Val Lys Arg
850                 855                 860
Ala Glu Lys Lys Trp Arg Asp Lys Arg Glu Lys Leu Glu Trp Glu Thr
865                 870                 875                 880
Asn Ile Val Tyr Lys Glu Ala Lys Glu Ser Val Asp Ala Leu Phe Val
                885                 890                 895
Asn Ser Gln Tyr Asp Arg Leu Gln Ala Asp Thr Asn Ile Ala Met Ile
            900                 905                 910
His Ala Ala Asp Lys Arg Val His Ser Ile Arg Glu Ala Tyr Leu Pro
            915                 920                 925
Glu Leu Ser Val Ile Pro Gly Val Asn Ala Ala Ile Phe Glu Glu Leu
            930                 935                 940
Glu Gly Arg Ile Phe Thr Ala Phe Ser Leu Tyr Asp Ala Arg Asn Val
945                 950                 955                 960
Ile Lys Asn Gly Asp Phe Asn Asn Gly Leu Ser Cys Trp Asn Val Lys
                965                 970                 975
Gly His Val Asp Val Glu Glu Gln Asn Asn His Arg Ser Val Leu Val
            980                 985                 990
Val Pro Glu Trp Glu Ala Glu Val Ser Gln Glu Val Arg Val Cys Pro
            995                 1000                1005
Gly Arg Gly Tyr Ile Leu Arg Val Thr Ala Tyr Lys Glu Gly Tyr
        1010                1015                1020
Gly Glu Gly Cys Val Thr Ile His Glu Ile Glu Asn Asn Thr Asp
        1025                1030                1035
Glu Leu Lys Phe Ser Asn Cys Val Glu Glu Glu Val Tyr Pro Asn
        1040                1045                1050
Asn Thr Val Thr Cys Asn Asp Tyr Thr Ala Thr Gln Glu Glu Tyr
        1055                1060                1065
Glu Gly Thr Tyr Thr Ser Arg Asn Arg Gly Tyr Asp Gly Ala Tyr
        1070                1075                1080
Glu Ser Asn Ser Ser Val Pro Ala Asp Tyr Ala Ser Ala Tyr Glu
        1085                1090                1095
Glu Lys Ala Tyr Thr Asp Gly Arg Arg Asp Asn Pro Cys Glu Ser
        1100                1105                1110
Asn Arg Gly Tyr Gly Asp Tyr Thr Pro Leu Pro Ala Gly Tyr Val
        1115                1120                1125
Thr Lys Glu Leu Glu Tyr Phe Pro Glu Thr Asp Lys Val Trp Ile
        1130                1135                1140
Glu Ile Gly Glu Thr Glu Gly Thr Phe Ile Val Asp Ser Val Glu
        1145                1150                1155
Leu Leu Leu Met Glu Glu
```

<210> SEQ ID NO 4
<211> LENGTH: 545
<212> TYPE: PRT
<213> ORGANISM: Artificial Sequence
<220> FEATURE:
<223> OTHER INFORMATION: Derived from Cry1Ab

<400> SEQUENCE: 4

```
Leu Glu Ala Glu Ser Asp Leu Glu Arg Ala Gln Lys Ala Val Asn Ala
1               5                   10                  15

Leu Phe Thr Ser Ser Asn Gln Ile Gly Leu Lys Thr Asp Val Thr Asp
            20                  25                  30

Tyr His Ile Asp Arg Val Ser Asn Leu Val Glu Cys Leu Ser Asp Glu
        35                  40                  45

Phe Cys Leu Asp Glu Lys Lys Glu Leu Ser Glu Lys Val Lys His Ala
    50                  55                  60

Lys Arg Leu Ser Asp Glu Arg Asn Leu Leu Gln Asp Pro Asn Phe Arg
65                  70                  75                  80

Gly Ile Asn Arg Gln Leu Asp Arg Gly Trp Arg Gly Ser Thr Asp Ile
                85                  90                  95

Thr Ile Gln Gly Gly Asp Asp Val Phe Lys Glu Asn Tyr Val Thr Leu
            100                 105                 110

Leu Gly Thr Phe Asp Glu Cys Tyr Pro Thr Tyr Leu Tyr Gln Lys Ile
        115                 120                 125

Asp Glu Ser Lys Leu Lys Ala Tyr Thr Arg Tyr Gln Leu Arg Gly Tyr
    130                 135                 140

Ile Glu Asp Ser Gln Asp Leu Glu Ile Tyr Leu Ile Arg Tyr Asn Ala
145                 150                 155                 160

Lys His Glu Thr Val Asn Val Pro Gly Thr Gly Ser Leu Trp Pro Leu
                165                 170                 175

Ser Ala Pro Ser Pro Ile Gly Lys Cys Ala His His Ser His His Phe
            180                 185                 190

Ser Leu Asp Ile Asp Val Gly Cys Thr Asp Leu Asn Glu Asp Leu Gly
        195                 200                 205

Val Trp Val Ile Phe Lys Ile Lys Thr Gln Asp Gly His Ala Arg Leu
    210                 215                 220

Gly Asn Leu Glu Phe Leu Glu Glu Lys Pro Leu Val Gly Glu Ala Leu
225                 230                 235                 240

Ala Arg Val Lys Arg Ala Glu Lys Lys Trp Arg Asp Lys Arg Glu Lys
                245                 250                 255

Leu Glu Trp Glu Thr Asn Ile Val Tyr Lys Glu Ala Lys Glu Ser Val
            260                 265                 270

Asp Ala Leu Phe Val Asn Ser Gln Tyr Asp Arg Leu Gln Ala Asp Thr
        275                 280                 285

Asn Ile Ala Met Ile His Ala Ala Asp Lys Arg Val His Ser Ile Arg
    290                 295                 300

Glu Ala Tyr Leu Pro Glu Leu Ser Val Ile Pro Gly Val Asn Ala Ala
305                 310                 315                 320

Ile Phe Glu Glu Leu Glu Gly Arg Ile Phe Thr Ala Phe Ser Leu Tyr
                325                 330                 335

Asp Ala Arg Asn Val Ile Lys Asn Gly Asp Phe Asn Asn Gly Leu Ser
            340                 345                 350

Cys Trp Asn Val Lys Gly His Val Asp Val Glu Glu Gln Asn Asn His
```

```
                355                 360                 365
Arg Ser Val Leu Val Pro Glu Trp Glu Ala Glu Val Ser Gln Glu
370                 375                 380

Val Arg Val Cys Pro Gly Arg Gly Tyr Ile Leu Arg Val Thr Ala Tyr
385                 390                 395                 400

Lys Glu Gly Tyr Gly Glu Gly Cys Val Thr Ile His Glu Ile Glu Asn
                405                 410                 415

Asn Thr Asp Glu Leu Lys Phe Ser Asn Cys Val Glu Glu Val Tyr
            420                 425                 430

Pro Asn Asn Thr Val Thr Cys Asn Asp Tyr Thr Ala Thr Gln Glu Glu
                435                 440                 445

Tyr Glu Gly Thr Tyr Thr Ser Arg Asn Arg Gly Tyr Asp Gly Ala Tyr
            450                 455                 460

Glu Ser Asn Ser Ser Val Pro Ala Asp Tyr Ala Ser Ala Tyr Glu Glu
465                 470                 475                 480

Lys Ala Tyr Thr Asp Gly Arg Arg Asp Asn Pro Cys Glu Ser Asn Arg
                485                 490                 495

Gly Tyr Gly Asp Tyr Thr Pro Leu Pro Ala Gly Tyr Val Thr Lys Glu
            500                 505                 510

Leu Glu Tyr Phe Pro Glu Thr Asp Lys Val Trp Ile Glu Ile Gly Glu
            515                 520                 525

Thr Glu Gly Thr Phe Ile Val Asp Ser Val Gly Leu Leu Leu Met Glu
            530                 535                 540

Glu
545

<210> SEQ ID NO 5
<211> LENGTH: 1164
<212> TYPE: PRT
<213> ORGANISM: Artificial Sequence
<220> FEATURE:
<223> OTHER INFORMATION: DIG-109 chimeric protein

<400> SEQUENCE: 5

Met Asp Asn Asn Pro Asn Ile Asn Glu Cys Ile Pro Tyr Asn Cys Leu
1               5                   10                  15

Ser Asn Pro Glu Glu Val Leu Leu Asp Gly Glu Arg Ile Ser Thr Gly
                20                  25                  30

Asn Ser Ser Ile Asp Ile Ser Leu Ser Leu Val Gln Phe Leu Val Ser
            35                  40                  45

Asn Phe Val Pro Gly Gly Gly Phe Leu Val Gly Leu Ile Asp Phe Val
        50                  55                  60

Trp Gly Ile Val Gly Pro Ser Gln Trp Asp Ala Phe Leu Val Gln Ile
65                  70                  75                  80

Glu Gln Leu Ile Asn Glu Arg Ile Ala Glu Phe Ala Arg Asn Ala Ala
                85                  90                  95

Ile Ala Asn Leu Glu Gly Leu Gly Asn Asn Phe Asn Ile Tyr Val Glu
            100                 105                 110

Ala Phe Lys Glu Trp Glu Glu Asp Pro Lys Asn Pro Ala Thr Arg Thr
        115                 120                 125

Arg Val Ile Asp Arg Phe Arg Ile Leu Asp Gly Leu Leu Glu Arg Asp
    130                 135                 140

Ile Pro Ser Phe Arg Ile Ser Gly Phe Glu Val Pro Leu Leu Ser Val
145                 150                 155                 160

Tyr Ala Gln Ala Ala Asn Leu His Leu Ala Ile Leu Arg Asp Ser Val
```

```
            165                 170                 175
Ile Phe Gly Glu Arg Trp Gly Leu Thr Thr Ile Asn Val Asn Glu Asn
                180                 185                 190

Tyr Asn Arg Leu Ile Arg His Ile Asp Glu Tyr Ala Asp His Cys Ala
                195                 200                 205

Asn Thr Tyr Asn Arg Gly Leu Asn Asn Leu Pro Lys Ser Thr Tyr Gln
                210                 215                 220

Asp Trp Ile Thr Tyr Asn Arg Leu Arg Arg Asp Leu Thr Leu Thr Val
225                 230                 235                 240

Leu Asp Ile Ala Ala Phe Phe Pro Asn Tyr Asp Asn Arg Arg Tyr Pro
                245                 250                 255

Ile Gln Pro Val Gly Gln Leu Thr Arg Glu Val Tyr Thr Asp Pro Leu
                260                 265                 270

Ile Asn Phe Asn Pro Gln Leu Gln Ser Val Ala Gln Leu Pro Thr Phe
                275                 280                 285

Asn Val Met Glu Asn Ser Ala Ile Arg Asn Pro His Leu Phe Asp Ile
                290                 295                 300

Leu Asn Asn Leu Thr Ile Phe Thr Asp Trp Phe Ser Val Gly Arg Asn
305                 310                 315                 320

Phe Tyr Trp Gly Gly His Arg Val Ile Ser Ser Leu Ile Gly Gly Gly
                325                 330                 335

Asn Ile Thr Ser Pro Ile Tyr Gly Arg Glu Ala Asn Gln Glu Pro Pro
                340                 345                 350

Arg Ser Phe Thr Phe Asn Gly Pro Val Phe Arg Thr Leu Ser Asn Pro
                355                 360                 365

Thr Leu Arg Leu Leu Gln Gln Pro Trp Pro Ala Pro Pro Phe Asn Leu
                370                 375                 380

Arg Gly Val Glu Gly Val Glu Phe Ser Thr Pro Thr Asn Ser Phe Thr
385                 390                 395                 400

Tyr Arg Gly Arg Gly Thr Val Asp Ser Leu Thr Glu Leu Pro Pro Glu
                405                 410                 415

Asp Asn Ser Val Pro Pro Arg Glu Gly Tyr Ser His Arg Leu Cys His
                420                 425                 430

Ala Thr Phe Val Gln Arg Ser Gly Thr Pro Phe Leu Thr Thr Gly Val
                435                 440                 445

Val Phe Ser Trp Thr His Arg Ser Ala Thr Leu Thr Asn Thr Ile Asp
                450                 455                 460

Pro Glu Arg Ile Asn Gln Ile Pro Leu Val Lys Gly Phe Arg Val Trp
465                 470                 475                 480

Gly Gly Thr Ser Val Ile Thr Gly Pro Gly Phe Thr Gly Gly Asp Ile
                485                 490                 495

Leu Arg Arg Asn Thr Phe Gly Asp Phe Val Ser Leu Gln Val Asn Ile
                500                 505                 510

Asn Ser Pro Ile Thr Gln Arg Tyr Arg Leu Arg Phe Arg Tyr Ala Ser
                515                 520                 525

Ser Arg Asp Ala Arg Val Ile Val Leu Thr Gly Ala Ala Ser Thr Gly
                530                 535                 540

Val Gly Gly Gln Val Ser Val Asn Met Pro Leu Gln Lys Thr Met Glu
545                 550                 555                 560

Ile Gly Glu Asn Leu Thr Ser Arg Thr Phe Arg Tyr Thr Asp Phe Ser
                565                 570                 575

Asn Pro Phe Ser Phe Arg Ala Asn Pro Asp Ile Ile Gly Ile Ser Glu
                580                 585                 590
```

```
Gln Pro Leu Phe Gly Ala Gly Ser Ile Ser Ser Gly Glu Leu Tyr Ile
        595                 600                 605

Asp Lys Ile Glu Ile Ile Leu Ala Asp Ala Thr Leu Glu Ala Glu Ser
    610                 615                 620

Asp Leu Glu Arg Ala Gln Lys Ala Val Asn Ala Leu Phe Thr Ser Ser
625                 630                 635                 640

Asn Gln Ile Gly Leu Lys Thr Asp Val Thr Asp Tyr His Ile Asp Arg
                645                 650                 655

Val Ser Asn Leu Val Glu Cys Leu Ser Asp Glu Phe Cys Leu Asp Glu
            660                 665                 670

Lys Lys Glu Leu Ser Glu Lys Val Lys His Ala Lys Arg Leu Ser Asp
        675                 680                 685

Glu Arg Asn Leu Leu Gln Asp Pro Asn Phe Arg Gly Ile Asn Arg Gln
    690                 695                 700

Leu Asp Arg Gly Trp Arg Gly Ser Thr Asp Ile Thr Ile Gln Gly Gly
705                 710                 715                 720

Asp Asp Val Phe Lys Glu Asn Tyr Val Thr Leu Leu Gly Thr Phe Asp
                725                 730                 735

Glu Cys Tyr Pro Thr Tyr Leu Tyr Gln Lys Ile Asp Glu Ser Lys Leu
            740                 745                 750

Lys Ala Tyr Thr Arg Tyr Gln Leu Arg Gly Tyr Ile Glu Asp Ser Gln
        755                 760                 765

Asp Leu Glu Ile Tyr Leu Ile Arg Tyr Asn Ala Lys His Glu Thr Val
    770                 775                 780

Asn Val Pro Gly Thr Gly Ser Leu Trp Pro Leu Ser Ala Pro Ser Pro
785                 790                 795                 800

Ile Gly Lys Cys Ala His His Ser His His Phe Ser Leu Asp Ile Asp
                805                 810                 815

Val Gly Cys Thr Asp Leu Asn Glu Asp Leu Gly Val Trp Val Ile Phe
            820                 825                 830

Lys Ile Lys Thr Gln Asp Gly His Ala Arg Leu Gly Asn Leu Glu Phe
        835                 840                 845

Leu Glu Glu Lys Pro Leu Val Gly Glu Ala Leu Ala Arg Val Lys Arg
    850                 855                 860

Ala Glu Lys Lys Trp Arg Asp Lys Arg Glu Lys Leu Glu Trp Glu Thr
865                 870                 875                 880

Asn Ile Val Tyr Lys Glu Ala Lys Glu Ser Val Asp Ala Leu Phe Val
                885                 890                 895

Asn Ser Gln Tyr Asp Arg Leu Gln Ala Asp Thr Asn Ile Ala Met Ile
            900                 905                 910

His Ala Ala Asp Lys Arg Val His Ser Ile Arg Glu Ala Tyr Leu Pro
        915                 920                 925

Glu Leu Ser Val Ile Pro Gly Val Asn Ala Ala Ile Phe Glu Glu Leu
    930                 935                 940

Glu Gly Arg Ile Phe Thr Ala Phe Ser Leu Tyr Asp Ala Arg Asn Val
945                 950                 955                 960

Ile Lys Asn Gly Asp Phe Asn Asn Gly Leu Ser Cys Trp Asn Val Lys
                965                 970                 975

Gly His Val Asp Val Glu Glu Gln Asn Asn His Arg Ser Val Leu Val
            980                 985                 990

Val Pro Glu Trp Glu Ala Glu Val  Ser Gln Glu Val Arg Val Cys Pro
        995                1000                1005
```

Gly Arg Gly Tyr Ile Leu Arg Val Thr Ala Tyr Lys Glu Gly Tyr
    1010                1015                1020

Gly Glu Gly Cys Val Thr Ile His Glu Ile Glu Asn Asn Thr Asp
    1025                1030                1035

Glu Leu Lys Phe Ser Asn Cys Val Glu Glu Val Tyr Pro Asn
    1040                1045                1050

Asn Thr Val Thr Cys Asn Asp Tyr Thr Ala Thr Gln Glu Glu Tyr
    1055                1060                1065

Glu Gly Thr Tyr Thr Ser Arg Asn Arg Gly Tyr Asp Gly Ala Tyr
    1070                1075                1080

Glu Ser Asn Ser Ser Val Pro Ala Asp Tyr Ala Ser Ala Tyr Glu
    1085                1090                1095

Glu Lys Ala Tyr Thr Asp Gly Arg Arg Asp Asn Pro Cys Glu Ser
    1100                1105                1110

Asn Arg Gly Tyr Gly Asp Tyr Thr Pro Leu Pro Ala Gly Tyr Val
    1115                1120                1125

Thr Lys Glu Leu Glu Tyr Phe Pro Glu Thr Asp Lys Val Trp Ile
    1130                1135                1140

Glu Ile Gly Glu Thr Glu Gly Thr Phe Ile Val Asp Ser Val Glu
    1145                1150                1155

Leu Leu Leu Met Glu Glu
    1160

<210> SEQ ID NO 6
<211> LENGTH: 10
<212> TYPE: PRT
<213> ORGANISM: Artificial Sequence
<220> FEATURE:
<223> OTHER INFORMATION: immunogenic peptide

<400> SEQUENCE: 6

Val Gln Arg Ser Gly Thr Pro Phe Leu Thr
1               5                   10

<210> SEQ ID NO 7
<211> LENGTH: 10
<212> TYPE: PRT
<213> ORGANISM: Artificial Sequence
<220> FEATURE:
<223> OTHER INFORMATION: immunogenic peptide

<400> SEQUENCE: 7

Ser Glu Gln Pro Leu Phe Gly Ala Gly Ser
1               5                   10

<210> SEQ ID NO 8
<211> LENGTH: 3492
<212> TYPE: DNA
<213> ORGANISM: Artificial Sequence
<220> FEATURE:
<223> OTHER INFORMATION: DIG-109 maize-optimized coding region

<400> SEQUENCE: 8
atggataaca accccaacat taacgagtgc atcccgtaca actgcctctc gaatccagaa      60
gaagtgctct tggatggcga gaggatttcg actggcaaca gctccatcga catttccctc     120
tccttggttc agttccttgt gtctaacttc gtccctggcg gtggcttcct tgttggcctt     180
atcgacttcg tctggggaat tgtcggaccc tcccagtggg atgcgtttct ggtgcagata     240
gagcagctga tcaacgagag gatcgctgag ttcgcgagaa atgctgcaat cgccaacctt     300

```
gaagggcttg gcaacaactt caacatctac gtggaggcgt tcaaggagtg ggaagaggac    360
cctaagaatc cagcgaccag aacgagggtt atagatcggt tccgcatcct cgatggcctt    420
ttggagaggg acatcccgag cttccgcatt tcggatttga aggttcctct gctctcagtc    480
tacgctcaag ctgctaatct gcatctggcc atcttgaggg attcagtcat ctttggcgaa    540
cgctggggtc ttacgactat caacgtgaac gagaactaca atcggttgat tcggcacata    600
gacgagtatg ccgaccactg tgctaacacc tacaataggg gtctgaacaa tctgccaaag    660
tcaacgtatc aagactggat aacctacaat aggctcagac gggacctcac tctcaccgtg    720
ctggacatag ctgccttctt tccgaactac gacaaccgga gatatcctat tcaacccgtt    780
ggtcagctca ctcgcgaggt ctacaccgat cccctcatca acttcaatcc ccagctgcaa    840
tcggtcgcac agctgcccac cttcaatgtg atggaaaact cagcgatccg gaatccccat    900
ctgtttgaca tacttaacaa cctcactatc ttcaccgatt ggttttcagt tggacgcaac    960
ttctactggg gagggcacag agtgatttca gcctcattg gaggagggaa cattacatcg    1020
cctatctatg gaagggaggc caaccaagag ccaccaaggt cttcaccttt caacggtccg    1080
gtgttcagaa cacttagcaa tcccacattg cgcttgctgc aacagccgtg gccagcacca    1140
ccattcaatc tgagggagt ggagggtgtg gagttctcga cgcctacaaa ctcctttacg    1200
tacagaggca gagggacagt ggactcactg acagaactcc cacctgagga caactctgtt    1260
cctccgaggg agggctactc gcaccggctt tgccatgcca ccttcgtcca gaggtctggc    1320
acgccttttc tgaccactgg ggttgtcttt agctggactc accgctcagc gacgctgacc    1380
aacacaatcg acccagagag gatcaatcag atccctctgg tgaagggctt tcgcgtttgg    1440
ggtggcacaa gcgtgatcac cggacctggt ttcactggtg gggatatcct cagacgcaat    1500
acgtttggcg atttcgtgag ccttcaagtc aacatcaatt ccccaatcac ccagagatat    1560
cggctccgct tcagatacgc ctcatccaga gacgcaaggg tcatcgtcct tactggagca    1620
gccagcaccg gagtcggagg ccaagttagc gtcaacatgc cgttgcagaa aacgatggaa    1680
atcggtgaaa acctcaccag cagaaccttt cgctatacag atttcagcaa cccttttctcc   1740 ttcagagcca atccggacat aatcggcata tccgagcagc ccttgttcgg tgctgggtcc    1800
atctcttctg gcgagctgta catcgacaag attgagatca ttctcgcaga tgcgactctc    1860
gaggctgaat cggatcttga aagggcacag aaggcagtca acgctctctt caccagctca    1920
aatcagattg gccttaagac cgatgttact gactatcata tcgacagagt ttctaacctt    1980
gtcgagtgcc tctccgacga gttctgtctc gacgaaaaga aggaactctc cgagaaagtg    2040
aagcacgcga aacgcctctc ggatgaacgg aacttgctgc aagatccgaa cttcagaggc    2100
atcaatcgcc agttggatag aggctggagg ggatcaaccg acataaccat tcaaggtggg    2160
gatgatgtgt tcaaggaaaa ctacgtgaca ttgctgggca ccttcgacga gtgctatccc    2220
acgtatctct atcagaagat tgacgagtcc aagctcaaag cctacacacg ctatcagctc    2280
agaggctaca ttgaggactc tcaagacctc gaaatctact tgatcagata caacgccaag    2340
cacgagacgg tgaacgtccc tgggactggg tcactgtggc cactgtcggc accctcgcca    2400
atcggaaagt gcgctcacca cagccaccac ttctcccttg acatagatgt tgggtgtacg    2460
gacttgaatg aggatctggg tgtgtgggtg atctttaaga tcaagaccca agatggtcat    2520
gcgaggcttg gcaaccttga gttccttgaa gagaagcctt tggtcggaga ggcactggct    2580
cgcgtgaaga gggctgagaa gaaatggagg gacaagaggg agaaactgga gtgggagacc    2640
aacatagtgt acaaggaggc caaggagtca gtggacgcac tgtttgtcaa ttcccagtat    2700
```

```
gataggctcc aagcggacac gaacatcgcc atgatccatg cagcggacaa gagggttcac    2760
tccataaggg aggcctatct tccggagctg tcagtgattc ctggggtcaa cgcagccatc    2820
tttgaggaat tggaagggag gatcttcacc gctttctctc tgtacgacgc tcggaacgtc    2880
atcaagaatg gtgatttcaa caatggactc agctgctgga acgtgaaagg gcatgtcgat    2940
gttgaagaac agaacaatca ccgcagcgtg ctggtggttc cggagtggga agccgaggtc    3000
tcacaagaag tcagagtgtg ccctggagg ggttacatct tgcgggtcac agcctacaag    3060
gaaggttatg gcgaaggctg tgtcacgatc catgagatcg aaaacaacac agacgagctg    3120
aagttttcca actgtgttga ggaggaggtc tatcctaaca atactgttac gtgcaacgac    3180
tacacagcca ctcaagagga gtacgagggc acttacacct ctcgcaacag aggctacgac    3240
ggtgcctacg agtcaaacag ctccgtgcca gcggactacg cctcggctta cgaagagaag    3300
gcgtacaccg acggtcggag ggataacccg tgcgagagca atagaggcta tggcgactac    3360
actcctctcc cagctggcta cgtgaccaag gagttggagt actttccgga gacagacaaa    3420
gtctggattg agattggaga gacagaaggc acgttcatcg tggactctgt tgaactcttg    3480
ctgatggagg ag                                                         3492

<210> SEQ ID NO 9
<211> LENGTH: 21
<212> TYPE: DNA
<213> ORGANISM: Artificial Sequence
<220> FEATURE:
<223> OTHER INFORMATION: oligonucleotide

<400> SEQUENCE: 9
cctgctccac taccagtaca a                                                21

<210> SEQ ID NO 10
<211> LENGTH: 21
<212> TYPE: DNA
<213> ORGANISM: Artificial Sequence
<220> FEATURE:
<223> OTHER INFORMATION: oligonucleotide

<400> SEQUENCE: 10
gtccaagaag gtgaccttct c                                                21

<210> SEQ ID NO 11
<211> LENGTH: 23
<212> TYPE: DNA
<213> ORGANISM: Artificial Sequence
<220> FEATURE:
<223> OTHER INFORMATION: oligonucleotide

<400> SEQUENCE: 11
agatcaccga ctttgcgctc ttt                                              23

<210> SEQ ID NO 12
<211> LENGTH: 17
<212> TYPE: DNA
<213> ORGANISM: Artificial Sequence
<220> FEATURE:
<223> OTHER INFORMATION: oligonucleotide

<400> SEQUENCE: 12
cctccctctt tgacgcc                                                     17

<210> SEQ ID NO 13
```

```
<211> LENGTH: 19
<212> TYPE: DNA
<213> ORGANISM: Artificial Sequence
<220> FEATURE:
<223> OTHER INFORMATION: oligonucleotide

<400> SEQUENCE: 13
agccacatcc cagtaacga                                                    19

<210> SEQ ID NO 14
<211> LENGTH: 20
<212> TYPE: DNA
<213> ORGANISM: Artificial Sequence
<220> FEATURE:
<223> OTHER INFORMATION: oligonucleotide

<400> SEQUENCE: 14
cagcccaatg aggcatgagc                                                   20

<210> SEQ ID NO 15
<211> LENGTH: 18
<212> TYPE: DNA
<213> ORGANISM: Artificial Sequence
<220> FEATURE:
<223> OTHER INFORMATION: oligonucleotide

<400> SEQUENCE: 15
tgtgttgagg aggaggtc                                                     18

<210> SEQ ID NO 16
<211> LENGTH: 18
<212> TYPE: DNA
<213> ORGANISM: Artificial Sequence
<220> FEATURE:
<223> OTHER INFORMATION: oligonucleotide

<400> SEQUENCE: 16
ccttctcttc gtaagccg                                                     18

<210> SEQ ID NO 17
<211> LENGTH: 23
<212> TYPE: DNA
<213> ORGANISM: Artificial Sequence
<220> FEATURE:
<223> OTHER INFORMATION: oligonucleotide

<400> SEQUENCE: 17
tcaagaggag tacgagggca ctt                                               23

<210> SEQ ID NO 18
<211> LENGTH: 20
<212> TYPE: DNA
<213> ORGANISM: Artificial Sequence
<220> FEATURE:
<223> OTHER INFORMATION: oligonucleotide

<400> SEQUENCE: 18
tgttcggttc cctctaccaa                                                   20

<210> SEQ ID NO 19
<211> LENGTH: 22
<212> TYPE: DNA
<213> ORGANISM: Artificial Sequence
<220> FEATURE:
<223> OTHER INFORMATION: oligonucleotide

<400> SEQUENCE: 19
```

```
caacatccat caccttgact ga                                          22

<210> SEQ ID NO 20
<211> LENGTH: 24
<212> TYPE: DNA
<213> ORGANISM: Artificial Sequence
<220> FEATURE:
<223> OTHER INFORMATION: oligonucleotide

<400> SEQUENCE: 20
cacagaaccg tcgcttcagc aaca                                        24

<210> SEQ ID NO 21
<211> LENGTH: 18
<212> TYPE: DNA
<213> ORGANISM: Artificial Sequence
<220> FEATURE:
<223> OTHER INFORMATION: oligonucleotide

<400> SEQUENCE: 21
tgtgttgagg aggaggtc                                               18

<210> SEQ ID NO 22
<211> LENGTH: 18
<212> TYPE: DNA
<213> ORGANISM: Artificial Sequence
<220> FEATURE:
<223> OTHER INFORMATION: oligonucleotide

<400> SEQUENCE: 22
ccttctcttc gtaagccg                                               18

<210> SEQ ID NO 23
<211> LENGTH: 23
<212> TYPE: DNA
<213> ORGANISM: Artificial Sequence
<220> FEATURE:
<223> OTHER INFORMATION: oligonucleotide

<400> SEQUENCE: 23
tcaagaggag tacgagggca ctt                                         23

<210> SEQ ID NO 24
<211> LENGTH: 18
<212> TYPE: DNA
<213> ORGANISM: Artificial Sequence
<220> FEATURE:
<223> OTHER INFORMATION: oligonucleotide

<400> SEQUENCE: 24
tggcggacga cgacttgt                                               18

<210> SEQ ID NO 25
<211> LENGTH: 19
<212> TYPE: DNA
<213> ORGANISM: Artificial Sequence
<220> FEATURE:
<223> OTHER INFORMATION: oligonucleotide

<400> SEQUENCE: 25
aaagtttgga ggctgccgt                                              19

<210> SEQ ID NO 26
<211> LENGTH: 26
<212> TYPE: DNA
```

```
<213> ORGANISM: Artificial Sequence
<220> FEATURE:
<223> OTHER INFORMATION: oligonucleotide

<400> SEQUENCE: 26
cgagcagacc gccgtgtact tctacc                                                26

<210> SEQ ID NO 27
<211> LENGTH: 1079
<212> TYPE: PRT
<213> ORGANISM: Artificial Sequence
<220> FEATURE:
<223> OTHER INFORMATION: DIG-110 Chimeric protein

<400> SEQUENCE: 27
```

| Met | Gly | Ile | Ala | Glu | Phe | Ala | Arg | Asn | Ala | Ala | Ile | Ala | Asn | Leu | Glu |
|---|---|---|---|---|---|---|---|---|---|---|---|---|---|---|---|
| 1 | | | | 5 | | | | | 10 | | | | | 15 | |

Gly Leu Gly Asn Asn Phe Asn Ile Tyr Val Glu Ala Phe Lys Glu Trp
            20                  25                  30

Glu Glu Asp Pro Lys Asn Pro Ala Thr Arg Thr Arg Val Ile Asp Arg
         35                  40                  45

Phe Arg Ile Leu Asp Gly Leu Leu Glu Arg Asp Ile Pro Ser Phe Arg
 50                  55                  60

Ile Ser Gly Phe Glu Val Pro Leu Leu Ser Val Tyr Ala Gln Ala Ala
65                  70                  75                  80

Asn Leu His Leu Ala Ile Leu Arg Asp Ser Val Ile Phe Gly Glu Arg
             85                  90                  95

Trp Gly Leu Thr Thr Ile Asn Val Asn Glu Asn Tyr Asn Arg Leu Ile
            100                 105                 110

Arg His Ile Asp Glu Tyr Ala Asp His Cys Ala Asn Thr Tyr Asn Arg
        115                 120                 125

Gly Leu Asn Asn Leu Pro Lys Ser Thr Tyr Gln Asp Trp Ile Thr Tyr
130                 135                 140

Asn Arg Leu Arg Arg Asp Leu Thr Leu Thr Val Leu Asp Ile Ala Ala
145                 150                 155                 160

Phe Phe Pro Asn Tyr Asp Asn Arg Arg Tyr Pro Ile Gln Pro Val Gly
                165                 170                 175

Gln Leu Thr Arg Glu Val Tyr Thr Asp Pro Leu Ile Asn Phe Asn Pro
            180                 185                 190

Gln Leu Gln Ser Val Ala Gln Leu Pro Thr Phe Asn Val Met Glu Asn
        195                 200                 205

Ser Ala Ile Arg Asn Pro His Leu Phe Asp Ile Leu Asn Asn Leu Thr
210                 215                 220

Ile Phe Thr Asp Trp Phe Ser Val Gly Arg Asn Phe Tyr Trp Gly Gly
225                 230                 235                 240

His Arg Val Ile Ser Ser Leu Ile Gly Gly Gly Asn Ile Thr Ser Pro
                245                 250                 255

Ile Tyr Gly Arg Glu Ala Asn Gln Glu Pro Pro Arg Ser Phe Thr Phe
            260                 265                 270

Asn Gly Pro Val Phe Arg Thr Leu Ser Asn Pro Thr Leu Arg Leu Leu
        275                 280                 285

Gln Gln Pro Trp Pro Ala Pro Pro Phe Asn Leu Arg Gly Val Glu Gly
290                 295                 300

Val Glu Phe Ser Thr Pro Thr Asn Ser Phe Thr Tyr Arg Gly Arg Gly
305                 310                 315                 320

Thr Val Asp Ser Leu Thr Glu Leu Pro Pro Glu Asp Asn Ser Val Pro

-continued

```
            325                 330                 335
Pro Arg Glu Gly Tyr Ser His Arg Leu Cys His Ala Thr Phe Val Gln
            340
Arg Ser Gly Thr Pro Phe Leu Thr Thr Gly Val Val Phe Ser Trp Thr
        355                 360                 365
His Arg Ser Ala Thr Leu Thr Asn Thr Ile Asp Pro Glu Arg Ile Asn
    370                 375                 380
Gln Ile Pro Leu Val Lys Gly Phe Arg Val Trp Gly Gly Thr Ser Val
385                 390                 395                 400
Ile Thr Gly Pro Gly Phe Thr Gly Gly Asp Ile Leu Arg Arg Asn Thr
                405                 410                 415
Phe Gly Asp Phe Val Ser Leu Gln Val Asn Ile Asn Ser Pro Ile Thr
            420                 425                 430
Gln Arg Tyr Arg Leu Arg Phe Arg Tyr Ala Ser Ser Arg Asp Ala Arg
        435                 440                 445
Val Ile Val Leu Thr Gly Ala Ala Ser Thr Gly Val Gly Gly Gln Val
    450                 455                 460
Ser Val Asn Met Pro Leu Gln Lys Thr Met Glu Ile Gly Glu Asn Leu
465                 470                 475                 480
Thr Ser Arg Thr Phe Arg Tyr Thr Asp Phe Ser Asn Pro Phe Ser Phe
                485                 490                 495
Arg Ala Asn Pro Asp Ile Ile Gly Ile Ser Glu Gln Pro Leu Phe Gly
            500                 505                 510
Ala Gly Ser Ile Ser Ser Gly Glu Leu Tyr Ile Asp Lys Ile Glu Ile
        515                 520                 525
Ile Leu Ala Asp Ala Thr Leu Glu Ala Glu Ser Asp Leu Glu Arg Ala
    530                 535                 540
Gln Lys Ala Val Asn Ala Leu Phe Thr Ser Ser Asn Gln Ile Gly Leu
545                 550                 555                 560
Lys Thr Asp Val Thr Asp Tyr His Ile Asp Arg Val Ser Asn Leu Val
                565                 570                 575
Glu Cys Leu Ser Asp Glu Phe Cys Leu Asp Glu Lys Lys Glu Leu Ser
            580                 585                 590
Glu Lys Val Lys His Ala Lys Arg Leu Ser Asp Glu Arg Asn Leu Leu
        595                 600                 605
Gln Asp Pro Asn Phe Arg Gly Ile Asn Arg Gln Leu Asp Arg Gly Trp
    610                 615                 620
Arg Gly Ser Thr Asp Ile Thr Ile Gln Gly Gly Asp Asp Val Phe Lys
625                 630                 635                 640
Glu Asn Tyr Val Thr Leu Leu Gly Thr Phe Asp Glu Cys Tyr Pro Thr
                645                 650                 655
Tyr Leu Tyr Gln Lys Ile Asp Glu Ser Lys Leu Lys Ala Tyr Thr Arg
            660                 665                 670
Tyr Gln Leu Arg Gly Tyr Ile Glu Asp Ser Gln Asp Leu Glu Ile Tyr
        675                 680                 685
Leu Ile Arg Tyr Asn Ala Lys His Glu Thr Val Asn Val Pro Gly Thr
    690                 695                 700
Gly Ser Leu Trp Pro Leu Ser Ala Pro Ser Pro Ile Gly Lys Cys Ala
705                 710                 715                 720
His His Ser His His Phe Ser Leu Asp Ile Asp Val Gly Cys Thr Asp
                725                 730                 735
Leu Asn Glu Asp Leu Gly Val Trp Val Ile Phe Lys Ile Lys Thr Gln
            740                 745                 750
```

Asp Gly His Ala Arg Leu Gly Asn Leu Glu Phe Leu Glu Glu Lys Pro
    755                 760                 765

Leu Val Gly Glu Ala Leu Ala Arg Val Lys Arg Ala Glu Lys Lys Trp
770                 775                 780

Arg Asp Lys Arg Glu Lys Leu Glu Trp Glu Thr Asn Ile Val Tyr Lys
785                 790                 795                 800

Glu Ala Lys Glu Ser Val Asp Ala Leu Phe Val Asn Ser Gln Tyr Asp
                805                 810                 815

Arg Leu Gln Ala Asp Thr Asn Ile Ala Met Ile His Ala Ala Asp Lys
                820                 825                 830

Arg Val His Ser Ile Arg Glu Ala Tyr Leu Pro Glu Leu Ser Val Ile
                835                 840                 845

Pro Gly Val Asn Ala Ala Ile Phe Glu Glu Leu Glu Gly Arg Ile Phe
            850                 855                 860

Thr Ala Phe Ser Leu Tyr Asp Ala Arg Asn Val Ile Lys Asn Gly Asp
865                 870                 875                 880

Phe Asn Asn Gly Leu Ser Cys Trp Asn Val Lys Gly His Val Asp Val
                    885                 890                 895

Glu Glu Gln Asn Asn His Arg Ser Val Leu Val Val Pro Glu Trp Glu
                900                 905                 910

Ala Glu Val Ser Gln Glu Val Arg Val Cys Pro Gly Arg Gly Tyr Ile
                915                 920                 925

Leu Arg Val Thr Ala Tyr Lys Glu Gly Tyr Gly Glu Gly Cys Val Thr
            930                 935                 940

Ile His Glu Ile Glu Asn Asn Thr Asp Glu Leu Lys Phe Ser Asn Cys
945                 950                 955                 960

Val Glu Glu Glu Val Tyr Pro Asn Asn Thr Val Thr Cys Asn Asp Tyr
                    965                 970                 975

Thr Ala Thr Gln Glu Glu Tyr Glu Gly Thr Tyr Thr Ser Arg Asn Arg
                980                 985                 990

Gly Tyr Asp Gly Ala Tyr Glu Ser Asn Ser Ser Val Pro Ala Asp Tyr
            995                 1000                1005

Ala Ser Ala Tyr Glu Glu Lys Ala Tyr Thr Asp Gly Arg Arg Asp
    1010                1015                1020

Asn Pro Cys Glu Ser Asn Arg Gly Tyr Gly Asp Tyr Thr Pro Leu
    1025                1030                1035

Pro Ala Gly Tyr Val Thr Lys Glu Leu Glu Tyr Phe Pro Glu Thr
    1040                1045                1050

Asp Lys Val Trp Ile Glu Ile Gly Glu Thr Glu Gly Thr Phe Ile
    1055                1060                1065

Val Asp Ser Val Glu Leu Leu Leu Met Glu Glu
    1070                1075

<210> SEQ ID NO 28
<211> LENGTH: 3237
<212> TYPE: DNA
<213> ORGANISM: Artificial Sequence
<220> FEATURE:
<223> OTHER INFORMATION: DIG-110 maize-optimized coding region

<400> SEQUENCE: 28
atgggcatcg ctgagttcgc gagaaatgct gcaatcgcca accttgaagg gcttggcaac      60
aacttcaaca tctacgtgga ggcgttcaag gagtgggaag aggaccctaa gaatccagcg     120
accagaacga gggttataga tcggttccgc atcctcgatg gcctttggga gagggacatc     180

```
ccgagcttcc gcatttcggg atttgaggtt cctctgctct cagtctacgc tcaagctgct      240
aatctgcatc tggccatctt gagggattca gtcatctttg gcgaacgctg gggtcttacg      300
actatcaacg tgaacgagaa ctacaatcgg ttgattcggc acatagacga gtatgccgac      360
cactgtgcta acacctacaa tagggtctg aacaatctgc aaagtcaac gtatcaagac        420
tggataacct acaataggct cagacgggac ctcactctca ccgtgctgga catagctgcc      480
ttctttccga actacgacaa ccggagatat cctattcaac ccgttggtca gctcactcgc      540
gaggtctaca ccgatcccct catcaacttc aatccccagc tgcaatcggt cgcacagctg      600
cccaccttca atgtgatgga aaactcagcg atccggaatc cccatctgtt tgacatactt      660
aacaacctca ctatcttcac cgattggttt tcagttggac gcaacttcta ctggggaggg      720
cacagagtga tttcaagcct cattggagga gggaacatta catcgcctat ctatggaagg      780
gaggccaacc aagagccacc aaggtctttc accttcaacg gtccggtgtt cagaacactt      840
agcaatccca cattgcgctt gctgcaacag ccgtggccag caccaccatt caatctgagg      900
ggagtggagg gtgtggagtt ctcgacgcct acaaactcct ttacgtacag aggcagaggg      960
acagtggact cactgacaga actcccacct gaggacaact ctgttcctcc gagggagggc      1020
tactcgcacc ggctttgcca tgccaccttc gtccagaggt ctggcacgcc ttttctgacc      1080
actgggggttg tctttagctg gactcaccgc tcagcgacgc tgaccaacac aatcgaccca      1140
gagaggatca atcagatccc tctggtgaag ggctttcgcg tttggggtgg cacaagcgtg      1200
atcaccggac ctggtttcac tggtggggat atcctcagac gcaatacgtt tggcgatttc      1260
gtgagccttc aagtcaacat caattcccca atcacccaga gatatcggct ccgcttcaga      1320
tacgcctcat ccagagacgc aagggtcatc gtccttactg gagcagccag caccggagtc      1380
ggaggccaag ttagcgtcaa catgccgttg cagaaaacga tggaaatcgg tgaaaacctc      1440
accagcagaa cctttcgcta tacagatttc agcaacccctt tctccttcag agccaatccg      1500
gacataatcg gcatatccga gcagcccttg ttcggtgctg ggtccatctc ttctggcgag      1560
ctgtacatcg acaagattga gatcattctc gcagatgcga ctctcgaggc tgaatcggat      1620
cttgaaaggg cacagaaggc agtcaacgct ctcttcacca gctcaaatca gattggcctt      1680
aagaccgatg ttactgacta tcatatcgac agagtttcta accttgtcga gtgcctctcc      1740
gacgagttct gtctcgacga aaagaaggaa ctctccgaga agtgaagca gcgaaacgc        1800
ctctcggatg aacggaactt gctgcaagat ccgaacttca gaggcatcaa tcgccagttg      1860
gatagaggct ggaggggatc aaccgacata accattcaag gtggggatga tgtgttcaag      1920
gaaaactacg tgacattgct gggcaccttc gacgagtgct atcccacgta tctctatcag      1980
aagattgacg agtccaagct caaagcctac acacgctatc agctcagagg ctacattgag      2040
gactctcaag acctcgaaat ctacttgatc agatacaacg ccaagcacga gacggtgaac      2100
gtccctggga ctgggtcact gtggccactg tcggcaccct cgccaatcgg aaagtgcgct      2160
caccacagcc accacttctc ccttgacata gatgttgggt gtacggactt gaatgaggat      2220
ctgggtgtgt gggtgatctt taagatcaag acccaagatg gtcatgcgag gcttggcaac      2280
cttgagttcc ttgaagagaa gcctttggtc ggagaggcac tggctcgcgt gaagagggct      2340
gagaagaaat ggaggggacaa gagggagaaa ctggagtggg agaccaacat agtgtacaag      2400
gaggccaagt agtcagtgga cgcactgttt gtcaattccc agtatgatag gctccaagcg      2460
gacacgaaca tcgccatgat ccatgcagcg gacaagaggg ttcactccat aagggaggcc      2520
```

```
tatcttccgg agctgtcagt gattcctggg gtcaacgcag ccatctttga ggaattggaa    2580
gggaggatct tcaccgcttt ctctctgtac gacgctcgga acgtcatcaa gaatggtgat    2640
ttcaacaatg gactcagctg ctggaacgtg aaagggcatg tcgatgttga agaacagaac    2700
aatcaccgca gcgtgctggt ggttccggag tgggaagccg aggtctcaca agaagtcaga    2760
gtgtgccctg gaggggtta catcttgcgg gtcacagcct acaaggaagg ttatggcgaa    2820
ggctgtgtca cgatccatga gatcgaaaac aacacagacg agctgaagtt ttccaactgt    2880
gttgaggagg aggtctatcc taacaatact gttacgtgca acgactacac agccactcaa    2940
gaggagtacg agggcactta cacctctcgc aacagaggct acgacggtgc ctacgagtca    3000
aacagctccg tgccagcgga ctacgcctcg gcttacgaag agaaggcgta caccgacggt    3060
cggagggata acccgtgcga gagcaataga ggctatggcg actacactcc tctcccagct    3120
ggctacgtga ccaaggagtt ggagtacttt ccggagacag acaaagtctg gattgagatt    3180
ggagagacag aaggcacgtt catcgtggac tctgttgaac tcttgctgat ggaggag      3237
```

<210> SEQ ID NO 29
<211> LENGTH: 543
<212> TYPE: PRT
<213> ORGANISM: Artificial Sequence
<220> FEATURE:
<223> OTHER INFORMATION: DIG-111 truncated protein

<400> SEQUENCE: 29

```
Met Gly Ile Ala Glu Phe Ala Arg Asn Ala Ala Ile Ala Asn Leu Glu
1               5                   10                  15

Gly Leu Gly Asn Asn Phe Asn Ile Tyr Val Glu Ala Phe Lys Glu Trp
            20                  25                  30

Glu Glu Asp Pro Lys Asn Pro Ala Thr Arg Thr Arg Val Ile Asp Arg
        35                  40                  45

Phe Arg Ile Leu Asp Gly Leu Leu Glu Arg Asp Ile Pro Ser Phe Arg
    50                  55                  60

Ile Ser Gly Phe Glu Val Pro Leu Leu Ser Val Tyr Ala Gln Ala Ala
65                  70                  75                  80

Asn Leu His Leu Ala Ile Leu Arg Asp Ser Val Ile Phe Gly Glu Arg
                85                  90                  95

Trp Gly Leu Thr Thr Ile Asn Val Asn Glu Asn Tyr Asn Arg Leu Ile
            100                 105                 110

Arg His Ile Asp Glu Tyr Ala Asp His Cys Ala Asn Thr Tyr Asn Arg
        115                 120                 125

Gly Leu Asn Asn Leu Pro Lys Ser Thr Tyr Gln Asp Trp Ile Thr Tyr
    130                 135                 140

Asn Arg Leu Arg Arg Asp Leu Thr Leu Thr Val Leu Asp Ile Ala Ala
145                 150                 155                 160

Phe Phe Pro Asn Tyr Asp Asn Arg Arg Tyr Pro Ile Gln Pro Val Gly
                165                 170                 175

Gln Leu Thr Arg Glu Val Tyr Thr Asp Pro Leu Ile Asn Phe Asn Pro
            180                 185                 190

Gln Leu Gln Ser Val Ala Gln Leu Pro Thr Phe Asn Val Met Glu Asn
        195                 200                 205

Ser Ala Ile Arg Asn Pro His Leu Phe Asp Ile Leu Asn Asn Leu Thr
    210                 215                 220

Ile Phe Thr Asp Trp Phe Ser Val Gly Arg Asn Phe Tyr Trp Gly Gly
225                 230                 235                 240
```

His Arg Val Ile Ser Ser Leu Ile Gly Gly Asn Ile Thr Ser Pro
            245                 250                 255

Ile Tyr Gly Arg Glu Ala Asn Gln Glu Pro Pro Arg Ser Phe Thr Phe
        260                 265                 270

Asn Gly Pro Val Phe Arg Thr Leu Ser Asn Pro Thr Leu Arg Leu Leu
    275                 280                 285

Gln Gln Pro Trp Pro Ala Pro Pro Phe Asn Leu Arg Gly Val Glu Gly
290                 295                 300

Val Glu Phe Ser Thr Pro Thr Asn Ser Phe Thr Tyr Arg Gly Arg Gly
305                 310                 315                 320

Thr Val Asp Ser Leu Thr Glu Leu Pro Pro Glu Asp Asn Ser Val Pro
                325                 330                 335

Pro Arg Glu Gly Tyr Ser His Arg Leu Cys His Ala Thr Phe Val Gln
            340                 345                 350

Arg Ser Gly Thr Pro Phe Leu Thr Thr Gly Val Val Phe Ser Trp Thr
        355                 360                 365

His Arg Ser Ala Thr Leu Thr Asn Thr Ile Asp Pro Glu Arg Ile Asn
    370                 375                 380

Gln Ile Pro Leu Val Lys Gly Phe Arg Val Trp Gly Gly Thr Ser Val
385                 390                 395                 400

Ile Thr Gly Pro Gly Phe Thr Gly Gly Asp Ile Leu Arg Arg Asn Thr
                405                 410                 415

Phe Gly Asp Phe Val Ser Leu Gln Val Asn Ile Asn Ser Pro Ile Thr
            420                 425                 430

Gln Arg Tyr Arg Leu Arg Phe Arg Tyr Ala Ser Ser Arg Asp Ala Arg
        435                 440                 445

Val Ile Val Leu Thr Gly Ala Ala Ser Thr Gly Val Gly Gly Gln Val
    450                 455                 460

Ser Val Asn Met Pro Leu Gln Lys Thr Met Glu Ile Gly Glu Asn Leu
465                 470                 475                 480

Thr Ser Arg Thr Phe Arg Tyr Thr Asp Phe Ser Asn Pro Phe Ser Phe
                485                 490                 495

Arg Ala Asn Pro Asp Ile Ile Gly Ile Ser Glu Gln Pro Leu Phe Gly
            500                 505                 510

Ala Gly Ser Ile Ser Ser Gly Glu Leu Tyr Ile Asp Lys Ile Glu Ile
        515                 520                 525

Ile Leu Ala Asp Ala Thr Leu Glu Ala Glu Ser Asp Leu Glu Arg
    530                 535                 540

<210> SEQ ID NO 30
<211> LENGTH: 1629
<212> TYPE: DNA
<213> ORGANISM: Artificial Sequence
<220> FEATURE:
<223> OTHER INFORMATION: DIG-111 maize-optimized coding region

<400> SEQUENCE: 30
atgggcatcg ctgagttcgc gagaaatgct gcaatcgcca accttgaagg gcttggcaac      60
aacttcaaca tctacgtgga ggcgttcaag gagtgggaag aggaccctaa gaatccagcg     120
accagaacga gggttataga tcggttccgc atcctcgatg ccttttggaa gagggacatc     180
ccgagcttcc gcatttcggg atttgaggtt cctctgctct cagtctacgc tcaagctgct     240
aatctgcatc tggccatctt gagggattca gtcatctttg cgaacgctg gggtcttacg     300 actatcaacg tgaacgagaa ctacaatcgg ttgattcggc acatagacga gtatgccgac     360

```
cactgtgcta acacctacaa taggggtctg aacaatctgc caaagtcaac gtatcaagac    420
tggataacct acaataggct cagacgggac ctcactctca ccgtgctgga catagctgcc    480
ttctttccga actacgacaa ccggagatat cctattcaac ccgttggtca gctcactcgc    540
gaggtctaca ccgatcccct catcaacttc aatccccagc tgcaatcggt cgcacagctg    600
cccaccttca atgtgatgga aaactcagcg atccggaatc cccatctgtt tgacatactt    660
aacaacctca ctatcttcac cgattggttt tcagttggac gcaacttcta ctggggaggg    720
cacagagtga tttcaagcct cattggagga gggaacatta atcgcctat ctatggaagg     780
gaggccaacc aagagccacc aaggtctttc accttcaacg tccggtgtt cagaacactt     840
agcaatccca cattgcgctt gctgcaacag ccgtggccag caccaccatt caatctgagg    900
ggagtggagg gtgtggagtt ctcgacgcct acaaactcct ttacgtacag aggcagaggg    960
acagtggact cactgacaga actcccacct gaggacaact ctgttcctcc gagggagggc   1020
tactcgcacc ggctttgcca tgccaccttc gtccagaggt ctggcacgcc ttttctgacc   1080
actggggttg tctttagctg gactcaccgc tcagcgacgc tgaccaacac aatcgaccca   1140
gagaggatca atcagatccc tctggtgaag ggctttcgcg tttggggtgg cacaagcgtg   1200
atcaccggac ctggtttcac tggtggggat atcctcagac gcaatacgtt tggcgatttc   1260
gtgagccttc aagtcaacat caattccca atcacccaga gatatcggct ccgcttcaga   1320
tacgcctcat ccagagacgc aagggtcatc gtccttactg gagcagccag caccggagtc   1380
ggaggccaag ttagcgtcaa catgccgttg cagaaaacga tggaaatcgg tgaaaacctc   1440
accagcagaa cctttcgcta tacagatttc agcaaccctt tctccttcag agccaatccg   1500
gacataatcg gcatatccga gcagcccttg ttcggtgctg ggtccatctc ttctggcgag   1560
ctgtacatcg acaagattga gatcattctc gcagatgcga ctctcgaggc tgaatcggat   1620
cttgaaagg                                                           1629
```

<210> SEQ ID NO 31
<211> LENGTH: 1044
<212> TYPE: PRT
<213> ORGANISM: Artificial Sequence
<220> FEATURE:
<223> OTHER INFORMATION: DIG-112 chimeric protein

<400> SEQUENCE: 31

```
Met Gly Asn Pro Ala Thr Arg Thr Arg Val Ile Asp Arg Phe Arg Ile
1               5                   10                  15

Leu Asp Gly Leu Leu Glu Arg Asp Ile Pro Ser Phe Arg Ile Ser Gly
            20                  25                  30

Phe Glu Val Pro Leu Leu Ser Val Tyr Ala Gln Ala Ala Asn Leu His
        35                  40                  45

Leu Ala Ile Leu Arg Asp Ser Val Ile Phe Gly Glu Arg Trp Gly Leu
    50                  55                  60

Thr Thr Ile Asn Val Asn Glu Asn Tyr Asn Arg Leu Ile Arg His Ile
65                  70                  75                  80

Asp Glu Tyr Ala Asp His Cys Ala Asn Thr Tyr Asn Arg Gly Leu Asn
                85                  90                  95

Asn Leu Pro Lys Ser Thr Tyr Gln Asp Trp Ile Thr Tyr Asn Arg Leu
            100                 105                 110

Arg Arg Asp Leu Thr Leu Thr Val Leu Asp Ile Ala Ala Phe Phe Pro
        115                 120                 125

Asn Tyr Asp Asn Arg Arg Tyr Pro Ile Gln Pro Val Gly Gln Leu Thr
```

```
                130             135             140
Arg Glu Val Tyr Thr Asp Pro Leu Ile Asn Phe Asn Pro Gln Leu Gln
145                 150                 155                 160

Ser Val Ala Gln Leu Pro Thr Phe Asn Val Met Glu Asn Ser Ala Ile
                165                 170                 175

Arg Asn Pro His Leu Phe Asp Ile Leu Asn Asn Leu Thr Ile Phe Thr
                180                 185                 190

Asp Trp Phe Ser Val Gly Arg Asn Phe Tyr Trp Gly Gly His Arg Val
                195                 200                 205

Ile Ser Ser Leu Ile Gly Gly Asn Ile Thr Ser Pro Ile Tyr Gly
210                 215                 220

Arg Glu Ala Asn Gln Glu Pro Pro Arg Ser Phe Thr Phe Asn Gly Pro
225                 230                 235                 240

Val Phe Arg Thr Leu Ser Asn Pro Thr Leu Arg Leu Gln Gln Pro
                245                 250                 255

Trp Pro Ala Pro Pro Phe Asn Leu Arg Gly Val Glu Gly Val Glu Phe
                260                 265                 270

Ser Thr Pro Thr Asn Ser Phe Thr Tyr Arg Gly Arg Gly Thr Val Asp
                275                 280                 285

Ser Leu Thr Glu Leu Pro Pro Glu Asp Asn Ser Val Pro Pro Arg Glu
290                 295                 300

Gly Tyr Ser His Arg Leu Cys His Ala Thr Phe Val Gln Arg Ser Gly
305                 310                 315                 320

Thr Pro Phe Leu Thr Thr Gly Val Val Phe Ser Trp Thr His Arg Ser
                325                 330                 335

Ala Thr Leu Thr Asn Thr Ile Asp Pro Glu Arg Ile Asn Gln Ile Pro
                340                 345                 350

Leu Val Lys Gly Phe Arg Val Trp Gly Gly Thr Ser Val Ile Thr Gly
                355                 360                 365

Pro Gly Phe Thr Gly Gly Asp Ile Leu Arg Arg Asn Thr Phe Gly Asp
                370                 375                 380

Phe Val Ser Leu Gln Val Asn Ile Asn Ser Pro Ile Thr Gln Arg Tyr
385                 390                 395                 400

Arg Leu Arg Phe Arg Tyr Ala Ser Ser Arg Asp Ala Arg Val Ile Val
                405                 410                 415

Leu Thr Gly Ala Ala Ser Thr Gly Val Gly Gly Gln Val Ser Val Asn
                420                 425                 430

Met Pro Leu Gln Lys Thr Met Glu Ile Gly Glu Asn Leu Thr Ser Arg
                435                 440                 445

Thr Phe Arg Tyr Thr Asp Phe Ser Asn Pro Phe Ser Phe Arg Ala Asn
450                 455                 460

Pro Asp Ile Ile Gly Ile Ser Glu Gln Pro Leu Phe Gly Ala Gly Ser
465                 470                 475                 480

Ile Ser Ser Gly Glu Leu Tyr Ile Asp Lys Ile Glu Ile Ile Leu Ala
                485                 490                 495

Asp Ala Thr Leu Glu Ala Glu Ser Asp Leu Glu Arg Ala Gln Lys Ala
                500                 505                 510

Val Asn Ala Leu Phe Thr Ser Ser Asn Gln Ile Gly Leu Lys Thr Asp
                515                 520                 525

Val Thr Asp Tyr His Ile Asp Arg Val Ser Asn Leu Val Glu Cys Leu
                530                 535                 540

Ser Asp Glu Phe Cys Leu Asp Glu Lys Lys Glu Leu Ser Glu Lys Val
545                 550                 555                 560
```

```
Lys His Ala Lys Arg Leu Ser Asp Glu Arg Asn Leu Leu Gln Asp Pro
                565                 570                 575

Asn Phe Arg Gly Ile Asn Arg Gln Leu Asp Arg Gly Trp Arg Gly Ser
            580                 585                 590

Thr Asp Ile Thr Ile Gln Gly Gly Asp Asp Val Phe Lys Glu Asn Tyr
        595                 600                 605

Val Thr Leu Leu Gly Thr Phe Asp Glu Cys Tyr Pro Thr Tyr Leu Tyr
    610                 615                 620

Gln Lys Ile Asp Glu Ser Lys Leu Lys Ala Tyr Thr Arg Tyr Gln Leu
625                 630                 635                 640

Arg Gly Tyr Ile Glu Asp Ser Gln Asp Leu Glu Ile Tyr Leu Ile Arg
                645                 650                 655

Tyr Asn Ala Lys His Glu Thr Val Asn Val Pro Gly Thr Gly Ser Leu
            660                 665                 670

Trp Pro Leu Ser Ala Pro Ser Pro Ile Gly Lys Cys Ala His His Ser
        675                 680                 685

His His Phe Ser Leu Asp Ile Asp Val Gly Cys Thr Asp Leu Asn Glu
    690                 695                 700

Asp Leu Gly Val Trp Val Ile Phe Lys Ile Lys Thr Gln Asp Gly His
705                 710                 715                 720

Ala Arg Leu Gly Asn Leu Glu Phe Leu Glu Glu Lys Pro Leu Val Gly
                725                 730                 735

Glu Ala Leu Ala Arg Val Lys Arg Ala Glu Lys Lys Trp Arg Asp Lys
            740                 745                 750

Arg Glu Lys Leu Glu Trp Glu Thr Asn Ile Val Tyr Lys Glu Ala Lys
        755                 760                 765

Glu Ser Val Asp Ala Leu Phe Val Asn Ser Gln Tyr Asp Arg Leu Gln
770                 775                 780

Ala Asp Thr Asn Ile Ala Met Ile His Ala Ala Asp Lys Arg Val His
785                 790                 795                 800

Ser Ile Arg Glu Ala Tyr Leu Pro Glu Leu Ser Val Ile Pro Gly Val
                805                 810                 815

Asn Ala Ala Ile Phe Glu Glu Leu Glu Gly Arg Ile Phe Thr Ala Phe
            820                 825                 830

Ser Leu Tyr Asp Ala Arg Asn Val Ile Lys Asn Gly Asp Phe Asn Asn
        835                 840                 845

Gly Leu Ser Cys Trp Asn Val Lys Gly His Val Asp Val Glu Glu Gln
850                 855                 860

Asn Asn His Arg Ser Val Leu Val Val Pro Glu Trp Glu Ala Glu Val
865                 870                 875                 880

Ser Gln Glu Val Arg Val Cys Pro Gly Arg Gly Tyr Ile Leu Arg Val
                885                 890                 895

Thr Ala Tyr Lys Glu Gly Tyr Gly Glu Gly Cys Val Thr Ile His Glu
            900                 905                 910

Ile Glu Asn Asn Thr Asp Glu Leu Lys Phe Ser Asn Cys Val Glu Glu
        915                 920                 925

Glu Val Tyr Pro Asn Asn Thr Val Thr Cys Asn Asp Tyr Thr Ala Thr
930                 935                 940

Gln Glu Glu Tyr Glu Gly Thr Tyr Thr Ser Arg Asn Arg Gly Tyr Asp
945                 950                 955                 960

Gly Ala Tyr Glu Ser Asn Ser Ser Val Pro Ala Asp Tyr Ala Ser Ala
                965                 970                 975
```

Tyr Glu Glu Lys Ala Tyr Thr Asp Gly Arg Arg Asp Asn Pro Cys Glu
        980                 985                 990

Ser Asn Arg Gly Tyr Gly Asp Tyr  Thr Pro Leu Pro Ala  Gly Tyr Val
        995                 1000                1005

Thr Lys  Glu Leu Glu Tyr Phe  Pro Glu Thr Asp Lys  Val Trp Ile
        1010                1015                1020

Glu Ile  Gly Glu Thr Glu Gly  Thr Phe Ile Val Asp  Ser Val Glu
        1025                1030                1035

Leu Leu  Leu Met Glu Glu
        1040

<210> SEQ ID NO 32
<211> LENGTH: 3132
<212> TYPE: DNA
<213> ORGANISM: Artificial Sequence
<220> FEATURE:
<223> OTHER INFORMATION: DIG-112 maize-optimized coding region

<400> SEQUENCE: 32

```
atgggcaatc cagcgaccag aacgagggtt atagatcggt tccgcatcct cgatggcctt      60
ttggagaggg acatcccgag cttccgcatt tcgggatttg aggttcctct gctctcagtc     120
tacgctcaag ctgctaatct gcatctggcc atcttgaggg attcagtcat ctttggcgaa     180
cgctggggtc ttacgactat caacgtgaac gagaactaca atcggttgat tcggcacata     240
gacgagtatg ccgaccactg tgctaacacc tacaataggg gtctgaacaa tctgccaaag     300
tcaacgtatc aagactggat aacctacaat aggctcagac gggacctcac tctcaccgtg     360
ctggacatag ctgccttctt tccgaactac gacaaccgga gatatcctat tcaacccgtt     420
ggtcagctca ctcgcgaggt ctacaccgat cccctcatca acttcaatcc ccagctgcaa     480
tcggtcgcac agctgcccac cttcaatgtg atggaaaact cagcgatccg gaatccccat     540
ctgtttgaca tacttaacaa cctcactatc ttcaccgatt ggtttcagt tggacgcaac     600
ttctactggg gagggcacag agtgatttca gcctcattg aggagggaa cattacatcg     660
cctatctatg gaaggaggc caaccaagag ccaccaaggt cttcaccttt caacggtccg     720
gtgttcagaa cacttagcaa tcccacattg cgcttgctgc aacagccgtg gccagcacca     780
ccattcaatc tgaggggagt ggagggtgtg gagttctcga cgcctacaaa ctcctttacg     840
tacagaggca gaggacagt ggactcactg acagaactcc cacctgagga caactctgtt     900
cctccgaggg agggctactc gcaccggctt tgccatgcca ccttcgtcca gaggtctggc     960
acgccttttc tgaccactgg ggttgtcttt agctggactc accgctcagc gacgctgacc    1020
aacacaatcg acccagagag gatcaatcag atccctctgg tgaagggctt cgcgtttgg    1080
ggtggcacaa gcgtgatcac cggacctggt ttcactggtg gggatatcct cagacgcaat    1140
acgtttggcg atttcgtgag ccttcaagtc aacatcaatt ccccaatcac ccagagatat    1200
cggctccgct tcagatacgc ctcatccaga gacgcaaggg tcatcgtcct tactggagca    1260
gccagcaccg gagtcggagg ccaagttagc gtcaacatgc cgttgcagaa aacgatggaa    1320
atcggtgaaa acctcaccag cagaaccttt cgctatacag atttcagcaa ccctttctcc    1380
ttcagagcca atccggacat aatcggcata tccgagcagc ccttgttcgg tgctgggtcc    1440
atctcttctg gcgagctgta catcgacaag attgagatca ttctcgcaga tgcgactctc    1500
gaggctgaat cggatcttga aagggcacag aaggcagtca acgctctctt caccagctca    1560
aatcagattg gccttaagac cgatgttact gactatcata tcgacagagt ttctaacctt    1620
```

```
gtcgagtgcc tctccgacga gttctgtctc gacgaaaaga aggaactctc cgagaaagtg    1680
aagcacgcga aacgcctctc ggatgaacgg aacttgctgc aagatccgaa cttcagaggc    1740
atcaatcgcc agttggatag aggctggagg ggatcaaccg acataaccat tcaaggtggg    1800
gatgatgtgt tcaaggaaaa ctacgtgaca ttgctgggca ccttcgacga gtgctatccc    1860
acgtatctct atcagaagat tgacgagtcc aagctcaaag cctacacacg ctatcagctc    1920
agaggctaca ttgaggactc tcaagacctc gaaatctact tgatcagata caacgccaag    1980
cacgagacgg tgaacgtccc tgggactggg tcactgtggc cactgtcggc accctcgcca    2040
atcggaaagt gcgctcacca cagccaccac ttctcccttg acatagatgt tgggtgtacg    2100
gacttgaatg aggatctggg tgtgtgggtg atctttaaga tcaagaccca agatggtcat    2160
gcgaggcttg caaccttga gttccttgaa gagaagcctt tggtcggaga ggcactggct    2220
cgcgtgaaga gggctgagaa gaaatggagg acaagaggg agaaactgga gtgggagacc    2280
aacatagtgt acaaggaggc caaggagtca gtggacgcac tgtttgtcaa ttcccagtat    2340
gataggctcc aagcggacac gaacatcgcc atgatccatg cagcggacaa gagggttcac    2400
tccataaggg aggcctatct tccggagctg tcagtgattc ctggggtcaa cgcagccatc    2460
tttgaggaat tggaagggag gatcttcacc gctttctctc tgtacgacgc tcggaacgtc    2520
atcaagaatg gtgatttcaa caatggactc agctgctgga acgtgaaagg catgtcgat    2580 gttgaagaac agaacaatca ccgcagcgtg ctggtggttc cggagtggga agccgaggtc    2640
tcacaagaag tcagagtgtg ccctgggagg ggttacatct tgcgggtcac agcctacaag    2700
gaaggttatg gcgaaggctg tgtcacgatc catgagatcg aaaacaacac agacgagctg    2760 aagtttttcca actgtgttga ggaggaggtc tatcctaaca atactgttac gtgcaacgac    2820
tacacagcca ctcaagagga gtacgagggc acttacacct ctcgcaacag aggctacgac    2880
ggtgcctacg agtcaaacag ctccgtgcca gcggactacg cctcggctta cgaagagaag    2940
gcgtacaccg acggtcggag ggataacccg tgcgagagca atagaggcta tggcgactac    3000
actcctctcc cagctggcta cgtgaccaag gagttggagt actttccgga gacagacaaa    3060
gtctggattg agattggaga gacagaaggc acgttcatcg tggactctgt tgaactcttg    3120
ctgatggagg ag                                                       3132
```

<210> SEQ ID NO 33
<211> LENGTH: 508
<212> TYPE: PRT
<213> ORGANISM: Artificial Sequence
<220> FEATURE:
<223> OTHER INFORMATION: DIG-113 truncated protein

<400> SEQUENCE: 33

```
Met Gly Asn Pro Ala Thr Arg Thr Arg Val Ile Asp Arg Phe Arg Ile
1               5                   10                  15

Leu Asp Gly Leu Leu Glu Arg Asp Ile Pro Ser Phe Arg Ile Ser Gly
            20                  25                  30

Phe Glu Val Pro Leu Leu Ser Val Tyr Ala Gln Ala Ala Asn Leu His
        35                  40                  45

Leu Ala Ile Leu Arg Asp Ser Val Ile Phe Gly Glu Arg Trp Gly Leu
    50                  55                  60

Thr Thr Ile Asn Val Asn Glu Asn Tyr Asn Arg Leu Ile Arg His Ile
65                  70                  75                  80

Asp Glu Tyr Ala Asp His Cys Ala Asn Thr Tyr Asn Arg Gly Leu Asn
                85                  90                  95
```

```
Asn Leu Pro Lys Ser Thr Tyr Gln Asp Trp Ile Thr Tyr Asn Arg Leu
            100                 105                 110

Arg Arg Asp Leu Thr Leu Thr Val Leu Asp Ile Ala Ala Phe Phe Pro
        115                 120                 125

Asn Tyr Asp Asn Arg Arg Tyr Pro Ile Gln Pro Val Gly Gln Leu Thr
        130                 135                 140

Arg Glu Val Tyr Thr Asp Pro Leu Ile Asn Phe Asn Pro Gln Leu Gln
145                 150                 155                 160

Ser Val Ala Gln Leu Pro Thr Phe Asn Val Met Glu Asn Ser Ala Ile
            165                 170                 175

Arg Asn Pro His Leu Phe Asp Ile Leu Asn Asn Leu Thr Ile Phe Thr
            180                 185                 190

Asp Trp Phe Ser Val Gly Arg Asn Phe Tyr Trp Gly Gly His Arg Val
            195                 200                 205

Ile Ser Ser Leu Ile Gly Gly Gly Asn Ile Thr Ser Pro Ile Tyr Gly
            210                 215                 220

Arg Glu Ala Asn Gln Glu Pro Pro Arg Ser Phe Thr Phe Asn Gly Pro
225                 230                 235                 240

Val Phe Arg Thr Leu Ser Asn Pro Thr Leu Arg Leu Leu Gln Gln Pro
                245                 250                 255

Trp Pro Ala Pro Pro Phe Asn Leu Arg Gly Val Glu Gly Val Glu Phe
            260                 265                 270

Ser Thr Pro Thr Asn Ser Phe Thr Tyr Arg Gly Arg Gly Thr Val Asp
            275                 280                 285

Ser Leu Thr Glu Leu Pro Pro Glu Asp Asn Ser Val Pro Pro Arg Glu
            290                 295                 300

Gly Tyr Ser His Arg Leu Cys His Ala Thr Phe Val Gln Arg Ser Gly
305                 310                 315                 320

Thr Pro Phe Leu Thr Thr Gly Val Val Phe Ser Trp Thr His Arg Ser
                325                 330                 335

Ala Thr Leu Thr Asn Thr Ile Asp Pro Glu Arg Ile Asn Gln Ile Pro
            340                 345                 350

Leu Val Lys Gly Phe Arg Val Trp Gly Gly Thr Ser Val Ile Thr Gly
            355                 360                 365

Pro Gly Phe Thr Gly Gly Asp Ile Leu Arg Arg Asn Thr Phe Gly Asp
            370                 375                 380

Phe Val Ser Leu Gln Val Asn Ile Asn Ser Pro Ile Thr Gln Arg Tyr
385                 390                 395                 400

Arg Leu Arg Phe Arg Tyr Ala Ser Ser Arg Asp Ala Arg Val Ile Val
                405                 410                 415

Leu Thr Gly Ala Ala Ser Thr Gly Val Gly Gly Gln Val Ser Val Asn
            420                 425                 430

Met Pro Leu Gln Lys Thr Met Glu Ile Gly Glu Asn Leu Thr Ser Arg
            435                 440                 445

Thr Phe Arg Tyr Thr Asp Phe Ser Asn Pro Phe Ser Phe Arg Ala Asn
            450                 455                 460

Pro Asp Ile Ile Gly Ile Ser Glu Gln Pro Leu Phe Gly Ala Gly Ser
465                 470                 475                 480

Ile Ser Ser Gly Glu Leu Tyr Ile Asp Lys Ile Glu Ile Ile Leu Ala
                485                 490                 495

Asp Ala Thr Leu Glu Ala Glu Ser Asp Leu Glu Arg
            500                 505
```

<210> SEQ ID NO 34
<211> LENGTH: 1524
<212> TYPE: DNA
<213> ORGANISM: Artificial Sequence
<220> FEATURE:
<223> OTHER INFORMATION: DIG-113 maize-optimized coding region

<400> SEQUENCE: 34

```
atgggcaatc cagcgaccag aacgagggtt atagatcggt tccgcatcct cgatggcctt      60
ttggagaggg acatcccgag cttccgcatt tcgggatttg aggttcctct gctctcagtc     120
tacgctcaag ctgctaatct gcatctggcc atcttgaggg attcagtcat ctttggcgaa     180
cgctggggtc ttacgactat caacgtgaac gagaactaca atcggttgat tcggcacata     240
gacgagtatg ccgaccactg tgctaacacc tacaataggg gtctgaacaa tctgccaaag     300
tcaacgtatc aagactggat aacctacaat aggctcagac gggacctcac tctcaccgtg     360
ctggacatag ctgccttctt tccgaactac gacaaccgga gatatcctat tcaacccgtt     420
ggtcagctca ctcgcgaggt ctacaccgat cccctcatca acttcaatcc ccagctgcaa     480
tcggtcgcac agctgcccac cttcaatgtg atggaaaact cagcgatccg gaatccccat     540
ctgttttgaca tacttaacaa cctcactatc ttcaccgatt ggttttcagt tggacgcaac     600
ttctactggg gagggcacag agtgatttca gcctcattg gaggagggaa cattacatcg     660
cctatctatg aagggaggc caaccaagag ccaccaaggt cttthcacctt caacggtccg     720
gtgttcagaa cacttagcaa tcccacattg cgcttgctgc aacagccgtg gccagcacca     780
ccattcaatc tgaggggagt ggagggtgtg gagttctcga cgcctacaaa ctcctttacg     840
tacagaggca gaggacagt ggactcactg acagaactcc cacctgagga caactctgtt     900
cctccgaggg agggctactc gcaccggctt tgccatgcca cttcgtcca gaggtctggc     960
acgccttttc tgaccactgg ggttgtcttt agctggactc accgctcagc gacgctgacc    1020
aacacaatcg acccagagag gatcaatcag atccctctgg tgaagggctt tcgcgtttgg    1080
ggtggcacaa gcgtgatcac cggacctggt ttcactggtg gggatatcct cagacgcaat    1140
acgtttggcg atttcgtgag ccttcaagtc aacatcaatt ccccaatcac ccagagatat    1200
cggctccgct tcagatacgc ctcatccaga gacgcaaggg tcatcgtcct tactggagca    1260
gccagcaccg gagtcggagg ccaagttagc gtcaacatgc cgttgcagaa acgatggaa    1320
atcggtgaaa acctcaccag cagaaccttt cgctatacag atttcagcaa ccctttctcc    1380
ttcagagcca atccggacat aatcggcata tccgagcagc ccttgttcgg tgctgggtcc    1440
atctcttctg gcgagctgta catcgacaag attgagatca ttctcgcaga tgcgactctc    1500
gaggctgaat cggatcttga aagg                                           1524
```

<210> SEQ ID NO 35
<211> LENGTH: 582
<212> TYPE: PRT
<213> ORGANISM: Artificial Sequence
<220> FEATURE:
<223> OTHER INFORMATION: DIG-114 truncated protein

<400> SEQUENCE: 35

```
Met Asp Asn Asn Pro Asn Ile Asn Glu Cys Ile Pro Tyr Asn Cys Leu
1               5                   10                  15

Ser Asn Pro Glu Glu Val Leu Leu Asp Gly Glu Arg Ile Ser Thr Gly
            20                  25                  30

Asn Ser Ser Ile Asp Ile Ser Leu Ser Leu Val Gln Phe Leu Val Ser
```

```
            35                  40                  45
Asn Phe Val Pro Gly Gly Phe Leu Val Gly Leu Ile Asp Phe Val
 50                  55                  60

Trp Gly Ile Val Gly Pro Ser Gln Trp Asp Ala Phe Leu Val Gln Ile
 65                  70                  75                  80

Glu Gln Leu Ile Asn Glu Arg Ile Ala Glu Phe Ala Arg Asn Ala Ala
                 85                  90                  95

Ile Ala Asn Leu Glu Gly Leu Gly Asn Asn Phe Asn Ile Tyr Val Glu
                100                 105                 110

Ala Phe Lys Glu Trp Glu Glu Asp Pro Lys Asn Pro Ala Thr Arg Thr
            115                 120                 125

Arg Val Ile Asp Arg Phe Arg Ile Leu Asp Gly Leu Leu Glu Arg Asp
        130                 135                 140

Ile Pro Ser Phe Arg Ile Ser Gly Phe Glu Val Pro Leu Leu Ser Val
145                 150                 155                 160

Tyr Ala Gln Ala Ala Asn Leu His Leu Ala Ile Leu Arg Asp Ser Val
                165                 170                 175

Ile Phe Gly Glu Arg Trp Gly Leu Thr Thr Ile Asn Val Asn Glu Asn
            180                 185                 190

Tyr Asn Arg Leu Ile Arg His Ile Asp Glu Tyr Ala Asp His Cys Ala
        195                 200                 205

Asn Thr Tyr Asn Arg Gly Leu Asn Asn Leu Pro Lys Ser Thr Tyr Gln
210                 215                 220

Asp Trp Ile Thr Tyr Asn Arg Leu Arg Arg Asp Leu Thr Leu Thr Val
225                 230                 235                 240

Leu Asp Ile Ala Ala Phe Phe Pro Asn Tyr Asp Asn Arg Arg Tyr Pro
                245                 250                 255

Ile Gln Pro Val Gly Gln Leu Thr Arg Glu Val Tyr Thr Asp Pro Leu
            260                 265                 270

Ile Asn Phe Asn Pro Gln Leu Gln Ser Val Ala Gln Leu Pro Thr Phe
        275                 280                 285

Asn Val Met Glu Asn Ser Ala Ile Arg Asn Pro His Leu Phe Asp Ile
290                 295                 300

Leu Asn Asn Leu Thr Ile Phe Thr Asp Trp Phe Ser Val Gly Arg Asn
305                 310                 315                 320

Phe Tyr Trp Gly Gly His Arg Val Ile Ser Ser Leu Ile Gly Gly Gly
                325                 330                 335

Asn Ile Thr Ser Pro Ile Tyr Gly Arg Glu Ala Asn Gln Glu Pro Pro
            340                 345                 350

Arg Ser Phe Thr Phe Asn Gly Pro Val Phe Arg Thr Leu Ser Asn Pro
        355                 360                 365

Thr Leu Arg Leu Leu Gln Gln Pro Trp Pro Ala Pro Pro Phe Asn Leu
370                 375                 380

Arg Gly Val Glu Gly Val Glu Phe Ser Thr Pro Thr Asn Ser Phe Thr
385                 390                 395                 400

Tyr Arg Gly Arg Gly Thr Val Asp Ser Leu Thr Glu Leu Pro Pro Glu
                405                 410                 415

Asp Asn Ser Val Pro Pro Arg Glu Gly Tyr Ser His Arg Leu Cys His
            420                 425                 430

Ala Thr Phe Val Gln Arg Ser Gly Thr Pro Phe Leu Thr Thr Gly Val
        435                 440                 445

Val Phe Ser Trp Thr His Arg Ser Ala Thr Leu Thr Asn Thr Ile Asp
450                 455                 460
```

```
Pro Glu Arg Ile Asn Gln Ile Pro Leu Val Lys Gly Phe Arg Val Trp
465                 470                 475                 480

Gly Gly Thr Ser Val Ile Thr Gly Pro Gly Phe Thr Gly Gly Asp Ile
            485                 490                 495

Leu Arg Arg Asn Thr Phe Gly Asp Phe Val Ser Leu Gln Val Asn Ile
        500                 505                 510

Asn Ser Pro Ile Thr Gln Arg Tyr Arg Leu Arg Phe Arg Tyr Ala Ser
    515                 520                 525

Ser Arg Asp Ala Arg Val Ile Val Leu Thr Gly Ala Ala Ser Thr Gly
    530                 535                 540

Val Gly Gly Gln Val Ser Val Asn Met Pro Leu Gln Lys Thr Met Glu
545                 550                 555                 560

Ile Gly Glu Asn Leu Thr Ser Arg Thr Phe Arg Tyr Thr Asp Phe Ser
                565                 570                 575

Asn Pro Phe Ser Phe Arg
            580
```

<210> SEQ ID NO 36
<211> LENGTH: 1746
<212> TYPE: DNA
<213> ORGANISM: Artificial Sequence
<220> FEATURE:
<223> OTHER INFORMATION: DIG-114 maize-optimized coding region

<400> SEQUENCE: 36

| | |
|---|---:|
| atggataaca accccaacat taacgagtgc atcccgtaca actgcctctc gaatccagaa | 60 |
| gaagtgctct tggatggcga gaggatttcg actggcaaca gctccatcga catttccctc | 120 |
| tccttggttc agttccttgt gtctaacttc gtccctggcg gtggcttcct tgttggcctt | 180 |
| atcgacttcg tctggggaat tgtcggaccc tcccagtggg atgcgtttct ggtgcagata | 240 |
| gagcagctga tcaacgagag gatcgctgag ttcgcgagaa atgctgcaat cgccaacctt | 300 |
| gaagggcttg gcaacaactt caacatctac gtggaggcgt tcaaggagtg ggaagaggac | 360 |
| cctaagaatc agcgaccag aacgagggtt atagatcggt tccgcatcct cgatggcctt | 420 |
| ttggagaggg acatcccgag cttccgcatt tcgggatttg aggttcctct gctctcagtc | 480 |
| tacgctcaag ctgctaatct gcatctggcc atcttgaggg attcagtcat ctttggcgaa | 540 |
| cgctggggtc ttacgactat caacgtgaac gagaactaca tcggttgat tcggcacata | 600 |
| gacgagtatg ccgaccactg tgctaacacc tacaataggg gtctgaacaa tctgccaaag | 660 |
| tcaacgtatc aagactggat aacctacaat aggctcagac gggacctcac tctcaccgtg | 720 |
| ctggacatag ctgccttctt tccgaactac gacaaccgga gatatcctat tcaacccgtt | 780 |
| ggtcagctca ctcgcgaggt ctacaccgat cccctcatca acttcaatcc ccagctgcaa | 840 |
| tcggtcgcac agctgcccac cttcaatgtg atggaaaact cagcgatccg gaatccccat | 900 |
| ctgtttgaca tacttaacaa cctcactatc ttcaccgatt ggttttcagt tggacgcaac | 960 |
| ttctactggg gagggcacag agtgatttca gcctcattg gaggagggaa cattacatcg | 1020 |
| cctatctatg aagggaggc caaccaagag ccaccaaggt ctttcacctt caacggtccg | 1080 |
| gtgttcagaa cacttagcaa tcccacattg cgcttgctgc aacagccgtg ccagcacca | 1140 |
| ccattcaatc tgagggagt ggagggtgtg gagttctcga cgcctacaaa ctcctttacg | 1200 |
| tacagaggca gagggacagt ggactcactg acagaactcc cacctgagga caactctgtt | 1260 |
| cctccgaggg agggctactc gcaccggctt tgccatgcca ccttcgtcca gaggtctggc | 1320 |

| | | | | | |
|---|---|---|---|---|---|
| acgccttttc | tgaccactgg | ggttgtcttt | agctggactc | accgctcagc | gacgctgacc | 1380 |
| aacacaatcg | acccagagag | gatcaatcag | atccctctgg | tgaagggctt | tcgcgtttgg | 1440 |
| ggtggcacaa | gcgtgatcac | cggacctggt | ttcactggtg | gggatatcct | cagacgcaat | 1500 |
| acgtttggcg | atttcgtgag | ccttcaagtc | aacatcaatt | ccccaatcac | ccagagatat | 1560 |
| cggctccgct | tcagatacgc | ctcatccaga | gacgcaaggg | tcatcgtcct | tactggagca | 1620 |
| gccagcaccg | gagtcggagg | ccaagttagc | gtcaacatgc | cgttgcagaa | aacgatggaa | 1680 |
| atcggtgaaa | acctcaccag | cagaaccttt | cgctatacag | atttcagcaa | ccctttctcc | 1740 |
| ttcaga | | | | | | 1746 |

MODIFIED CRY1CA INSECTICIAL CRY PROTEINS

CROSS-REFERENCE TO RELATED APPLICATIONS

This is a national phase application, filed pursuant to 35 U.S.C. §371, of PCT application No. PCT/US10/60826 filed on Dec. 16, 2010, which claims the benefit of U.S. provisional application No. 61/284,275, filed on Dec. 16, 2009. The prior applications are incorporated herein by reference in their entirety.

FIELD OF THE INVENTION

This invention concerns new insecticidal Cry proteins and their use to control insect pests.

BACKGROUND OF THE INVENTION

Fall armyworm (FAW; *Spodoptera frugiperda*) causes significant damage to corn and other crops such as soybeans and cotton.

*Bacillus thuringiensis* (B.t.) is a soil-borne bacterium that produces pesticidal crystal proteins known as delta endotoxins or Cry proteins. Cry proteins are oral intoxicants that function by acting on midgut cells of susceptible insects. An extensive list of delta endotoxins is maintained and regularly updated at the website: lifesci.sussex.ac.uk/home/Neil_Crickmore/Bt/intro.html.

Transgenic corn expressing genes encoding Cry proteins, most notably Cry1F, provide commercial levels of efficacy against FAW.

Despite the success of FAW-resistant transgenic corn, the possibility of the development of resistant insect populations threatens the long-term durability of Cry proteins in FAW control and creates the need to discover and develop new Cry proteins to control-FAW and other pests. Insect resistance to B.t. Cry proteins can develop through several mechanisms (Heckel et al., 2007, Pigott and Ellar, 2007). Multiple receptor protein classes for Cry proteins have been identified within insects, and multiple examples exist within each receptor class. Resistance to a particular Cry protein may develop, for example, by means of a mutation within the toxin-binding portion of a cadherin domain of a receptor protein. A further means of resistance may be mediated through a protoxin-processing protease. Thus, resistance to Cry toxins in species of Lepidoptera has a complex genetic basis, with at least four distinct, major resistance genes. Lepidopteran insects resistant to Cry proteins have developed in the field for *Plutella xylostella* (Tabashnik, et al., 1994), *Trichoplusia ni* (Janmaat and Myers 2003, 2005), and *Helicoverpa zeae* (Tabashnik et al., 2008). Development of new high potency Cry proteins would provide additional tools for management of FAW and other insect pests. Cry proteins with different modes of action produced in combination in transgenic corn would prevent the development FAW insect resistance and protect the long term utility of B.t. technology for insect pest control.

BRIEF SUMMARY OF THE INVENTION

The present invention provides insecticidal B.t. Cry proteins, including the proteins designated herein as DIG-109 and DIG-152, as well as variants of DIG-109 and DIG-152, nucleic acids encoding these proteins, methods of controlling pests using the proteins, methods of producing the proteins in transgenic host cells, and transgenic plants that produce the proteins.

As described in Example 1, the DIG-109 and DIG-152 proteins comprise chimeric peptides composed of a core toxin segment of B.t. Cry1Ca and a Cry1Ab protoxin segment. Insecticidally active variants of the DIG-109 and DIG-152 proteins are also described.

A surprising finding reported herein is that DIG-109 and DIG-152 proteins are active against populations of fall armyworm larvae and sugarcane borer larvae that are resistant to Cry1F. Accordingly, DIG-109 and DIG-152 proteins are ideal candidates for use to control of Lepidopteran pests. The proteins can be used alone or in combination with other Cry proteins, such as Cry1F, Cry1Ab, and Cry1Ac, to control development of resistant insect populations. For a discussion of such pests, see e.g. Tabashnik, PNAS (2008), vol. 105 no. 49, 19029-19030.

Insecticidally active fragments of DIG-109 and DIG-152, and nucleotides encoding such fragments, are another aspect of the invention.

In one embodiment the invention provides an isolated DIG-109 protein polypeptide comprising a core toxin segment selected from the group consisting of
   (a) a polypeptide comprising the amino acid sequence of residues 28 to 619 of SEQ ID NO:1;
   (b) a polypeptide comprising an amino acid sequence having at least 90% sequence identity to the amino acid sequence of residues 28 to 619 of SEQ ID NO:1;
   (c) a polypeptide comprising an amino acid sequence of residues 28 to 619 of SEQ ID NO:1 with up to 20 amino acid substitutions, deletions, or modifications that do not adversely affect expression or activity of the protein encoded by SEQ ID NO:1.

In another embodiment the invention provides an isolated DIG-109 toxin polypeptide comprising a DIG-109 core toxin segment selected from the group consisting of
   (a) a polypeptide comprising the amino acid sequence of residues 1 to 619 of SEQ ID NO:1;
   (b) a polypeptide comprising an amino acid sequence having at least 90% sequence identity to the amino acid sequence of residues 1 to 619 of SEQ ID NO:1;
   (c) a polypeptide comprising an amino acid sequence of residues 1 to 619 of SEQ ID NO:1 with up to 20 amino acid substitutions, deletions, or modifications that do not adversely affect expression or activity of the protein encoded by SEQ ID NO:1.

In another embodiment the invention provides a plant comprising a DIG-109 protein.

In another embodiment the invention provides a method for controlling a pest population comprising contacting said population with a pesticidally effective amount of a DIG-109 protein.

In another embodiment the invention provides an isolated nucleic acid that encodes a DIG-109 protein.

In another embodiment the invention provides a DNA construct comprising a nucleotide sequence that encodes a DIG-109 protein operably linked to a promoter that is not derived from *Bacillus thuringiensis* and is capable of driving expression in a plant. The invention also provides a transgenic plant that comprises the DNA construct stably incorporated into its genome and a method for protecting a plant from a pest comprising introducing the construct into said plant.

BRIEF DESCRIPTION OF THE SEQUENCES

SEQ ID NO:1 Cry1Ca core toxin segment; 619 aa
SEQ ID NO:2 first Cry1Ab protoxin segment; 545 aa SEQ ID NO:3 DIG-152 chimeric protein; 1164 aa (Pf version)
SEQ ID NO:4 second Cry1Ab protoxin segment; 545 aa
SEQ ID NO:5 DIG-109 chimeric protein; 1164 aa (maize version)
SEQ ID NO:6 Cry1Ca436 peptide; 10 aa
SEQ ID NO:7 Cry1Ca591 peptide; 10 aa
SEQ ID NO:8 maize-optimized CDS encoding DIG-109; 3492 bp
SEQ ID NO:9 ZGP3S oligonucleotide; 21 nt
SEQ ID NO:10 ZGP3A oligonucleotide; 21 nt
SEQ ID NO:11 TQZGP3 oligonucleotide; 23 nt
SEQ ID NO:12 DSM2S oligonucleotide; 17 nt
SEQ ID NO:13 DSM2A oligonucleotide; 19 nt
SEQ ID NO:14 DSM2FQ oligonucleotide; 20 nt
SEQ ID NO:15 CRY1CaS oligonucleotide; 18 nt
SEQ ID NO:16 CRY1CaA oligonucleotide; 18 nt
SEQ ID NO:17 Cry1Ca oligonucleotide; 23 nt
SEQ ID NO:18 AAD1S oligonucleotide; 20 nt
SEQ ID NO:19 AAD1A oligonucleotide; 22 nt
SEQ ID NO:20 AAD1 oligonucleotide; 24 nt
SEQ ID NO:21 Y1CAS oligonucleotide; 18 nt
SEQ ID NO:22 Y1CAR oligonucleotide; 18 nt
SEQ ID NO:23 F6Y1CA oligonucleotide; 23 nt
SEQ ID NO:24 IVF-Taq oligonucleotide; 18 nt
SEQ ID NO:25 IVR-TAQ oligonucleotide; 19 nt
SEQ ID NO:26 IV-Probe oligonucleotide; 26 nt
SEQ ID NO:27 DIG-110; 1079 aa
SEQ ID NO:28 Maize-optimized coding region for DIG-110; 3237 bp
SEQ ID NO:29 DIG-111; 543 aa
SEQ ID NO:30 Maize-optimized coding region for DIG-111; 1629 bp
SEQ ID NO:31 DIG-112; 1044 aa
SEQ ID NO:32 Maize-optimized coding region for DIG-112; 3132 bp
SEQ ID NO:33 DIG-113; 508 aa
SEQ ID NO:34 Maize-optimized coding region for DIG-113; 1524 bp
SEQ ID NO:35 DIG-114; 582 aa
SEQ ID NO:36 Maize-optimized coding region for DIG-114; 1746 bp

DETAILED DESCRIPTION OF THE INVENTION

DIG-109 and DIG-152 Proteins, and Insecticidally Active Variants.

In addition to the full length DIG-109 protein of SEQ ID NO:5 and the DIG-152 protein of SEQ ID NO:3, the invention encompasses insecticidally active variants. By the term "variant", applicants intend to include fragments, certain deletion and insertion mutants, and certain fusion proteins. The Cry1Ca core toxin segment of DIG-109 and DIG-152 is a classic three-domain Cry protein. As a preface to describing variants of the DIG-109 and DIG-152 proteins that are included in the invention, it will be useful to briefly review the architecture of three-domain Cry proteins in general and of the DIG-109 and DIG-152 protein toxins in particular.

A majority of Bacillus thuringiensis delta-endotoxin crystal protein molecules are composed of two functional segments. The protease-resistant core toxin is the first segment and corresponds to about the first half of the protein molecule. The full ~130 kDa protoxin molecule is rapidly processed to the resistant core segment by proteases in the insect gut. The segment that is deleted by this processing will be referred to herein as the "protoxin segment." The protoxin segment is believed to participate in toxin crystal formation (Arvidson et al., (1989). The protoxin segment may thus convey a partial insect specificity for the toxin by limiting the accessibility of the core to the insect by reducing the protease processing of the toxin molecule (Haider et al., (1986) or by reducing toxin solubility (Aronson et al., (1991). B.t. toxins, even within a certain class, vary to some extent in length and in the precise location of the transition from the core toxin segment to protoxin segment. The transition from core toxin segment to protoxin segment will typically occur at between about 50% to about 60% of the full length toxin. SEQ ID NO:3 discloses the 1164 amino acid sequence of the full-length DIG-152 polypeptide, of which the N-terminal 619 amino acids comprise the Cry1Ca core toxin disclosed as SEQ ID NO:1. SEQ ID NO:5 discloses the 1164 amino acid sequence of the full-length DIG-109 polypeptide, of which the N-terminal 619 amino acids comprise the Cry1Ca core toxin.

Three dimensional crystal structures have been determined for Cry1Aa1, Cry2Aa1, Cry3Aa1, Cry3Bb1, Cry4Aa, Cry4Ba and Cry8Ea1. These structures for the core toxins are remarkably similar and are comprised of three distinct domains with the features described below (reviewed in de Maagd et al., 2003).

Domain I is a bundle of seven alpha helices where helix five is surrounded by six amphipathic helices. This domain has been implicated in pore formation and shares homology with other pore forming proteins including hemolysins and colicins. Domain I of the Cry1Ca core toxin protein comprises amino acid residues 36 to 254 of SEQ ID NO:1. [It is to be understood that the DIG-109 and DIG-152 chimeric proteins comprise the Cry1Ca core toxin segment, and therefore co-ordinates assigned to the amino acid sequence of the Cry1Ca core toxin segment as disclosed in SEQ ID NO:1 apply as well to the amino acid sequence of the DIG-109 chimeric protein disclosed in SEQ ID NO:5 and the amino acid sequence of the DIG-152 chimeric protein disclosed in SEQ ID NO:3.]

Domain II is formed by three anti-parallel beta sheets packed together in a beta prism. The loops of this domain play important roles in binding insect midgut receptors. In Cry1A proteins, surface exposed loops at the apices of Domain II beta sheets are involved in binding to Lepidopteran cadherin receptors. Cry3Aa Domain II loops bind a membrane-associated metalloprotease of Leptinotarsa decemlineata (Say) (Colorado potato beetle) in a similar fashion (Ochoa-Campuzano et al., 2007). Domain II shares homology with certain carbohydrate-binding proteins including vitelline and jacaline. Domain II of the Cry1Ca core toxin protein comprises amino acid residues 262 to 458 of SEQ ID NO:1.

Domain III is a beta sandwich of two anti-parallel beta sheets. Structurally this domain is related to carbohydrate-binding domains of proteins such as glucanases, galactose oxidase, sialidase and others. Domain III binds certain classes of receptor proteins and perhaps participates in insertion of an oligomeric toxin pre-pore that interacts with a second class of receptors, examples of which are aminopeptidase and alkaline phosphatase in the case of Cry1A proteins (Pigott and Ellar, 2007). Analogous Cry Domain III receptors have yet to be identified in Coleoptera. Conserved B.t. sequence blocks 2 and 3 map near the N-terminus and C-terminus of Domain 2, respectively. Hence, these conserved sequence blocks 2 and 3 are approximate boundary regions between the three functional domains. These regions of conserved DNA and protein homology have been exploited for engineering recombinant B.t. toxins (U.S. Pat. No. 6,090,931, WO 1991/01087, WO 1995/06730, WO 1998/022595). Domain III of the Cry1Ca protein comprises amino acid residues 468 to 617 of SEQ ID NO:1.

It has been reported that α-helix 1 of Domain I is removed following receptor binding. Aronson et al. (1999) demonstrated that Cry1Ac bound to BBMV was protected from proteinase K cleavage beginning at residue 59, just after α-helix 1; similar results were cited for Cry1Ab. Gomez et al., (2002) found that Cry1Ab oligomers formed upon BBMV receptor binding lacked the α-helix 1 portion of Domain I. Also, Soberon et al., (2007) have shown that N-terminal deletion mutants of Cry1Ab and Cry1Ac which lack approximately 60 amino acids encompassing α-helix 1 on the three dimensional Cry structure are capable of assembling monomers of molecular weight about 60 kDa into pre-pores in the absence of cadherin binding. These N-terminal deletion mutants were reported to be active on Cry-resistant insect larvae. Furthermore, Diaz-Mendoza et al., (2007) described Cry1Ab fragments of 43 kDa and 46 kDa that retained activity on Mediterranean corn borer (*Sesamia nonagrioides*). These fragments were demonstrated to include amino acid residues 116 to 423; however the precise amino acid sequences were not elucidated and the mechanism of activity of these proteolytic fragments is unknown. The results of Gomez et al., (2002), Soberon et al., 2007 and Diaz-Mendoza et al., (2007) contrast with those of Hofte et al., (1986), who reported that deletion of 36 amino acids from the N-terminus of Cry1Ab resulted in loss of insecticidal activity.

We have deduced the beginning and end of helices 1, 2A, 2B, 3, and 4, and the location of the spacer regions between them in Domain 1 of the Cry1Ca core toxin by comparing the Cry1Ca amino acid sequence with the amino acid sequence for Cry8Ea1, for which the structure is known. These locations are described in Table 1.

dicted α-helix 2A start, and may terminate after the α-helix 2B end, but preferably do not extend into α-helix 3.

In designing coding sequences for the N-terminal deletion variants, an ATG start codon, encoding methionine, is inserted at the 5' end of the nucleotide sequence designed to express the deletion variant. For sequences designed for use in transgenic plants, it may be of benefit to adhere to the "N-end rule" of Varshaysky (1997). It is taught that some amino acids may contribute to protein instability and degradation in eukaryotic cells when displayed as the N-terminal residue of a protein. For example, data collected from observations in yeast and mammalian cells indicate that the N-terminal destabilizing amino acids are F, L, W, Y, R, K, H, I, N, Q, D, E and possibly P. While the specifics of protein degradation mechanisms may differ somewhat between organisms, the conservation of identity of N-terminal destabilizing amino acids seen above suggests that similar mechanisms may function in plant cells. For instance, Worley et al., (1998) found that in plants, the N-end rule includes basic and aromatic residues. It is a possibility that proteolytic cleavage by plant proteases near the start of α-helix 3 of subject B.t. insecticidal proteins may expose a destabilizing N-terminal amino acid. Such processing may target the cleaved proteins for rapid decay and limit the accumulation of the B.t. insecticidal proteins to levels insufficient for effective insect control. Accordingly, for N-terminal deletion variants that begin with one of the destabilizing amino acids, applicants prefer to add a codon that specifies a G (glycine) amino acid between the translational initiation methionine and the destabilizing amino acid.

TABLE 1

Amino acid coordinates of projected α-helices of Cry1Ca core toxin protein.

| | Helix1 | spacer | Helix2A | spacer | Helix2B | spacer | Helix3 | spacer | Helix4 |
|---|---|---|---|---|---|---|---|---|---|
| Residues of SEQ ID NO: 1 | 35-49 | 50-54 | 55-62 | 63-70 | 71-84 | 85-90 | 91-119 | 120-123 | 124-145 |

Amino Terminal Deletion Variants of DIG-109 and DIG-152.

In one of its aspects the invention provides DIG-109 and DIG-152 variants in which all or part of alpha helices 1, 2A, and 2B are deleted to improve insecticidal activity and avoid development of resistance by insects. These modifications are made to provide DIG-109 and DIG-152 variants with improved attributes, such as improved target pest spectrum, potency, and insect resistance management. In some embodiments of the subject invention, the subject modifications may affect the efficiency of protoxin activation and pore formation, leading to insect intoxication. More specifically, to provide DIG-109 and DIG-152 variants with improved attributes, step-wise deletions are described that remove part of the gene encoding the N-terminus. The deletions remove all of α-helix 1 and all or part of α-helix 2 in Domain I, while maintaining the structural integrity of the α-helices 3 through 7. The subject invention therefore relates in part to improvements to Cry protein efficacy made by engineering the α-helical components of Domain 1 for more efficient pore formation. More specifically, the subject invention relates in part to improved DIG-109 and DIG-152 proteins designed to have N-terminal deletions in regions with putative secondary structure homology to α-helices 1 and 2 in Domain I of Cry1 proteins.

Deletions to improve the insecticidal properties of the DIG-109 and DIG-152 toxins may initiate before the predicted α-helix 2A start, and may terminate after the α-helix 2B end, but preferably do not extend into α-helix 3.

Examples 13 and 14 give specific examples of amino-terminal deletion variants of DIG-109 and DIG-152 in accordance with the invention. Additional useful fragments can be identified by insect bioassay of fragments generated by trypsin or chymotrypsin digestion of the full length solubilized crystal protein to determine which fragments retain toxicity, or may be identified by determining the sequence of a toxic protein fragment encoded by DNA fragments of the Cry protein coding region. This protein will mostly have a short N-terminal and a long C-terminal truncation compared to the protoxin. The N-terminal end of the smallest toxic fragment is conveniently determined by N-terminal amino acid sequence determination of trypsin- or chymotrypsin-treated soluble crystal protein by techniques routinely available in the art.

Chimeric Toxins.

Chimeric proteins utilizing the core toxin domain of one Cry toxin fused to the protoxin segment of another Cry toxin have previously been reported. DIG-109 and DIG-152 variants include toxins comprising an N-terminal toxin core segment of a Cry1Ca toxin (which may be full length or have the N-terminal deletions described above) fused to a heterologous protoxin segment at some point past the end of the core toxin segment. The transition to the heterologous protoxin segment can occur at approximately the core toxin/protoxin junction or, in the alternative, a portion of the native protoxin (extending past the core toxin segment) can be retained with the transition to the heterologous protoxin occurring downstream. As an example, a chimeric toxin of the subject invention has the full core toxin segment of Cry1Ca (amino acids 1-619) and a heterologous protoxin (amino acids 620 to the C-terminus). In preferred embodiments, the heterologous segment of the protoxin is derived from a Cry1Ab delta-endotoxin, as illustrated in SEQ ID NO:2 and SEQ ID NO:4.

Protease Sensitivity Variants.

Insect gut proteases typically function in aiding the insect in obtaining needed amino acids from dietary protein. The best understood insect digestive proteases are serine proteases, which appear to be the most common type (Englemann and Geraerts, 1980), particularly in Lepidopteran species. Coleopteran insects have guts that are more neutral to acidic than are Lepidopteran guts. The majority of Coleopteran larvae and adults, for example Colorado potato beetle, have slightly acidic midguts, and cysteine proteases provide the major proteolytic activity (Wolfson and Murdock, 1990). More precisely, Thie and Houseman (1990) identified and characterized the cysteine proteases, cathepsin B-like and cathepsin H-like, and the aspartyl protease, cathepsin D-like, in Colorado potato beetle. Gillikin et al., (1992) characterized the proteolytic activity in the guts of western corn rootworm larvae and found primarily cysteine proteases. U.S. Pat. No. 7,230,167 disclosed that the serine protease, cathepsin G, exists in western corn rootworm. The diversity and different activity levels of the insect gut proteases may influence an insect's sensitivity to a particular B.t. toxin.

In another embodiment of the invention, protease cleavage sites may be engineered at desired locations to affect protein processing within the midgut of susceptible larvae of certain insect pests (Walters et al., 2008). These protease cleavage sites may be introduced by methods such as chemical gene synthesis or splice overlap PCR (Horton et al., 1989). Serine protease recognition sequences, for example, can optionally be inserted at specific sites in the Cry protein structure to effect protein processing at desired deletion points within the midgut of susceptible larvae. Serine proteases that can be exploited in such fashion include Lepidopteran midgut serine proteases such as trypsin or trypsin-like enzymes, chymotrypsin, elastase, etc. (Christeller et al., 1992). Further, deletion sites identified empirically by sequencing Cry protein digestion products generated with unfractionated larval midgut protease preparations or by binding to brush border membrane vesicles can be engineered to effect protein activation. Modified Cry proteins generated either by gene deletion or by introduction of protease cleavage sites have improved activity on Lepidopteran pests including *Ostrinia nubilalis, Diatraea grandiosella, Helicoverpa zea, Agrotis ipsilon, Spodoptera frugiperda, Spodoptera exigua, Diatraea saccharalis, Loxagrotis albicosta*, and other target pests.

Coleopteran serine proteases such as trypsin, chymotrypsin and cathepsin G-like protease, Coleopteran cysteine proteases such as cathepsins (B-like, L-like, O-like, and K-like proteases) (Koiwa et al., (2000) and Bown et al., (2004), Coleopteran metal loproteases such as ADAM10 (Ochoa-Campuzano et al., (2007)), and Coleopteran aspartic acid proteases such as cathepsins D-like and E-like, pepsin, plasmepsin, and chymosin may further be exploited by engineering appropriate recognition sequences at desired processing sites to affect Cry protein processing within the midgut of susceptible larvae of certain insect pests.

A preferred location for the introduction of such protease cleavage sites may be within the "spacer" region between α-helix2B and α-helix 3, for example within amino acids 85 to 90 of the Cry1Ca core toxin protein (SEQ ID NO:1 and Table 1). Modified Cry proteins generated either by gene deletion or by introduction of protease cleavage sites have improved activity on insect pests including but not limited to fall armyworm, sugarcane borer, and the like.

Various technologies exist to enable determination of the sequence of the amino acids which comprise the N-terminal or C-terminal residues of polypeptides. For example, automated Edman degradation methodology can be used in sequential fashion to determine the N-terminal amino acid sequence of up to 30 amino acid residues with 98% accuracy per residue. Further, determination of the sequence of the amino acids comprising the carboxy end of polypeptides is also possible (Bailey et al., (1992); U.S. Pat. No. 6,046,053). Thus, in some embodiments, B.t. Cry proteins which have been activated by means of proteolytic processing, for example, by proteases prepared from the gut of an insect, may be characterized and the N-terminal or C-terminal amino acids of the activated toxin fragment identified. DIG-109 and DIG-152 variants produced by introduction or elimination of protease processing sites at appropriate positions in the coding sequence to allow, or eliminate, proteolytic cleavage of a larger variant protein by insect, plant or microorganism proteases are within the scope of the invention. The end result of such manipulation is understood to be the generation of toxin fragment molecules having the same or better activity as the intact (full length) toxin protein.

Domains of the DIG-109 and DIG-152 Toxins.

The separate domains of the Cry1Ca core toxin segment as exemplified in the DIG-109 and DIG-152 toxins, (and variants that are 90%, 95%, or 97% identical to such domains) are expected to be useful in forming combinations with domains from other Cry toxins to provide new toxins with increased spectrum of pest toxicity, improved potency, or increased protein stability. Domain I of the Cry1Ca core toxin protein consists of amino acid residues 36 to 254 of SEQ ID NO:1. Domain II of the Cry1Ca core toxin protein consists of amino acid residues 262 to 458 of SEQ ID NO:1. Domain III of the Cry1Ca core toxin protein consists of amino acid residues 468 to 617 of SEQ ID NO:1. Domain swapping or shuffling is a mechanism for generating altered delta-endotoxin proteins. Domains II and III may be swapped between delta-endotoxin proteins, resulting in hybrid or chimeric toxins with improved pesticidal activity or target spectrum. Domain II is involved in receptor binding. Domain III binds certain classes of receptor proteins and perhaps participates in insertion of an oligomeric toxin pre-pore. Some Domain III substitutions in other toxins have been shown to produce superior toxicity against *Spodoptera exigua* (de Maagd et al., (1996) and guidance exists on the design of the Cry toxin domain swaps (Knight et al., (2004).

Methods for generating recombinant proteins and testing them for pesticidal activity are well known in the art (see, for example, Naimov et al., (2001), de Maagd et al., (1996), Ge et al., (1991), Schnepf et al., (1990), Rang et al., (1999)). Domain I from Cry1A and Cry3A proteins has been studied for the ability to insert and form pores in membranes. Alpha-helices 4 and 5 of Domain I play key roles in membrane insertion and pore formation (Walters et al., 1993, Gazit et al., 1998; Nunez-Valdez et al., 2001), while the other helices are proposed to contact the membrane surface like the ribs of an umbrella (Bravo et al., (2007); Gazit et al., (1998)).

DIG-109 and DIG-152 Variants Created by Making a Limited Number of Amino Acid Deletions, Substitutions, or Additions.

Amino acid deletions, substitutions, and additions to the amino acid sequence of the Cry1Ca core toxin segment of SEQ ID NO:1 can readily be made in a sequential manner and the effects of such variations on insecticidal activity can be tested by bioassay. Provided the number of changes is limited in number, such testing does not involve unreasonable experimentation. The invention includes insecticidally active variants of the core toxin (amino acids 1-619 of SEQ ID NO:1) in which up to 10, up to 15, or up to 20 independent amino acid additions, deletions, or substitutions have been made.

The invention includes DIG-109 and DIG-152 variants having a core toxin segment that is 90%, 95% or 97% identical to amino acids 1-619 of SEQ ID NO:1. Variants may be made by making random mutations or the variants may be designed. In the case of designed mutants, there is a high probability of generating variants with similar activity to the native toxin when amino acid identity is maintained in important regions of the toxin that account for biological activity or are involved in the determination of three-dimensional configuration which ultimately is responsible for the biological activity. A high probability of retaining activity will also occur if substitutions are conservative. Amino acids may be placed in the following classes: non-polar, uncharged polar, basic, and acidic. Conservative substitutions whereby an amino acid of one class is replaced with another amino acid of the same type are least likely to materially alter the biological activity of the variant. Table 2 provides a listing of examples of amino acids belonging to each class.

TABLE 2

| Class of Amino Acid | Examples of Amino Acids |
|---|---|
| Nonpolar Side Chains | Ala, Val, Leu, Ile, Pro, Met, Phe, Trp |
| Uncharged Polar Side Chains | Gly, Ser, Thr, Cys, Tyr, Asn, Gln |
| Acidic Side Chains | Asp, Glu |
| Basic Side Chains | Lys, Arg, His |
| Beta-branched Side Chains | Thr, Val, Ile |
| Aromatic Side Chains | Tyr, Phe, Trp, His |

In some instances, non-conservative substitutions can also be made. An important factor is that these substitutions should not significantly detract from the biological activity of the toxin. Variants include polypeptides that differ in amino acid sequence due to mutagenesis. Variant proteins encompassed by the present invention are biologically active, that is they continue to possess the desired biological activity of the native protein, that is, retaining pesticidal activity.

Variant proteins can also be designed that differ at the sequence level but that retain the same or similar overall essential three-dimensional structure, surface charge distribution, and the like. See e.g. U.S. Pat. No. 7,058,515; Larson et al., (2002); Stemmer (1994a, 1994b, 1995); and Crameri et al., (1996a, 1996b, 1997).

Nucleic Acids.

Isolated nucleic acids encoding the DIG-109 toxin or encoding the DIG-152 toxin are one aspect of the present invention. This includes nucleic acids encoding SEQ ID NO:1, SEQ ID NO:3 and SEQ ID NO:5, and complements thereof, as well as other nucleic acids that encode insecticidal variants of SEQ ID NO:1, SEQ ID NO:3, and SEQ ID NO:5. By "isolated" applicants mean that the nucleic acid molecules have been removed from their native environment and have been placed in a different environment by the hand of man. Because of the redundancy of the genetic code, a variety of different DNA sequences can encode the amino acid sequences disclosed herein. It is well within the skill of a person trained in the art to create these alternative DNA sequences encoding the same, or essentially the same, toxins.

Gene Synthesis.

Genes encoding the improved Cry proteins described herein can be made by a variety of methods well-known in the art. For example, synthetic gene segments and synthetic genes can be made by phosphite tri-ester and phosphoramidite chemistry (Caruthers et al, 1987), and commercial vendors are available to perform gene synthesis on demand. Full-length genes can be assembled in a variety of ways including, for example, by ligation of restriction fragments or polymerase chain reaction assembly of overlapping oligonucleotides (Stewart and Burgin, 2005). Further, terminal gene deletions can be made by PCR amplification using site-specific terminal oligonucleotides.

Nucleic acids encoding DIG-109 toxin or DIG-152 toxin can be made for example, by synthetic construction by methods currently practiced by any of several commercial suppliers. (See for example, U.S. Pat. No. 7,482,119B2). These genes, or portions or variants thereof, may also be constructed synthetically, for example, by use of a gene synthesizer and the design methods of, for example, U.S. Pat. No. 5,380,831. Alternatively, variations of synthetic or naturally occurring genes may be readily constructed using standard molecular biological techniques for making point mutations. Fragments of these genes can also be made using commercially available exonucleases or endonucleases according to standard procedures. For example, enzymes such as Bal31 or site-directed mutagenesis can be used to systematically cut off nucleotides from the ends of these genes. Also, gene fragments which encode active toxin fragments may be obtained using a variety of restriction enzymes.

Given the amino acid sequence for a DIG-109 toxin or a DIG-152 toxin, a coding sequence can be designed by reverse translating the protein sequence using codons preferred by the intended host, and then refining the sequence using alternative (redundant) codons to remove sequences that might cause problems. Further, periodic stop codons may be engineered into the non-coding reading frames to eliminate long, inadvertent open reading frames.

Quantifying Sequence Identity.

To determine the percent identity of two amino acid sequences or of two nucleic acid sequences, the sequences are aligned for optimal comparison purposes. The percent identity between the two sequences is a function of the number of identical positions shared by the sequences (i.e. percent identity=number of identical positions/total number of positions (e.g. overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A nonlimiting example of such an algorithm is BLAST (Altschul et al., 1990, and Karlin and Altschul, 1990), modified as in Karlin and Altschul (1993), and incorporated into the BLASTN and BLASTX programs. BLAST searches may be conveniently used to identify sequences homologous (similar) to a query sequence in nucleic acid or protein databases. BLASTN searches can be performed, (score=100, word length=12) to identify nucleotide sequences having homology to claimed nucleic acid molecules of the invention. BLASTX searches can be performed (score=50, word length=3) to identify amino acid sequences having homology to claimed insecticidal protein molecules of the invention.

Gapped BLAST Altschul et al., (1997) can be utilized to obtain gapped alignments for comparison purposes, Alternatively, PSI-Blast can be used to perform an iterated search that detects distant relationships between molecules Altschul et al., (ibid.). When utilizing BLAST, Gapped BLAST, and PSI-Blast programs, the default parameters of the respective programs can be used. See www.ncbi.nlm.nih.gov.

A non-limiting example of a mathematical algorithm utilized for the comparison of sequences is the ClustalW algorithm (Thompson et al., 1994). ClustalW compares sequences and aligns the entirety of the amino acid or DNA sequence, and thus can provide data about the sequence conservation of the entire amino acid sequence or nucleotide sequence. The ClustalW algorithm is used in several commercially available DNA/amino acid analysis software packages, such as the ALIGNX module of the Vector NTI Program Suite (Invitrogen, Inc., Carlsbad, Calif.). When aligning amino acid sequences with ALIGNX, one may conveniently use the default settings with a Gap open penalty of 10, a Gap extend penalty of 0.1 and the blosum63mt2 comparison matrix to assess the percent amino acid similarity (consensus) or identity between the two sequences. When aligning DNA sequences with ALIGNX, one may conveniently use the default settings with a Gap open penalty of 15, a Gap extend penalty of 6.6 and the swgapdnamt comparison matrix to assess the percent identity between the two sequences.

Another non-limiting example of a mathematical algorithm utilized for the comparison of sequences is that of Myers and Miller (1988). Such an algorithm is incorporated into the wSTRETCHER program, which is part of the wEMBOSS sequence alignment software package (available at http://emboss.sourceforge.net/). wSTRETCHER calculates an optimal global alignment of two sequences using a modification of the classic dynamic programming algorithm which uses linear space. The substitution matrix, gap insertion penalty and gap extension penalties used to calculate the alignment may be specified. When utilizing the wSTRETCHER program for comparing nucleotide sequences, a Gap open penalty of 16 and a Gap extend penalty of 4 can be used with the scoring matrix file EDNAFULL. When used for comparing amino acid sequences, a Gap open penalty of 12 and a Gap extend penalty of 2 can be used with the EBLOSUM62 scoring matrix file.

A further non-limiting example of a mathematical algorithm utilized for the comparison of sequences is that of Needleman and Wunsch (1970), which is incorporated in the sequence alignment software packages GAP Version 10 and wNEEDLE (http://emboss.sourceforge.net/). GAP Version 10 may be used to determine sequence identity or similarity using the following parameters: for a nucleotide sequence, % identity and % similarity are found using GAP Weight of 50 and Length Weight of 3, and the nwsgapdna.cmp scoring matrix. For amino acid sequence comparison, % identity or % similarity are determined using GAP weight of 8 and length weight of 2, and the BLOSUM62 scoring program.

wNEEDLE reads two input sequences, finds the optimum alignment (including gaps) along their entire length, and writes their optimal global sequence alignment to file. The algorithm explores all possible alignments and chooses the best, using a scoring matrix that contains values for every possible residue or nucleotide match. wNEEDLE finds the alignment with the maximum possible score, where the score of an alignment is equal to the sum of the matches taken from the scoring matrix, minus penalties arising from opening and extending gaps in the aligned sequences. The substitution matrix and gap opening and extension penalties are user-specified. When amino acid sequences are compared, a default Gap open penalty of 10, a Gap extend penalty of 0.5, and the EBLOSUM62 comparison matrix are used. When DNA sequences are compared using wNEEDLE, a Gap open penalty of 10, a Gap extend penalty of 0.5, and the EDNAFULL comparison matrix are used.

Equivalent programs may also be used. By "equivalent program" is intended any sequence comparison program that, for any two sequences in question, generates an alignment having identical nucleotide or amino acid residue matches and an identical percent sequence identity when compared to the corresponding alignment generated by ALIGNX, wNEEDLE, or wSTRETCHER. The % identity is the percentage of identical matches between the two sequences over the reported aligned region (including any gaps in the length) and the % similarity is the percentage of matches between the two sequences over the reported aligned region (including any gaps in the length).

Alignment may also be performed manually by inspection.

Recombinant Hosts.

The toxin-encoding genes of the subject invention can be introduced into a wide variety of microbial or plant hosts. Expression of the toxin gene results, directly or indirectly, in the intracellular production and maintenance of the pesticidal protein. With suitable microbial hosts, e.g. *Pseudomonas*, the microbes can be applied to the environment of the pest, where they will proliferate and be ingested. The result is a control of the pest. Alternatively, the microbe hosting the toxin gene can be treated under conditions that prolong the activity of the toxin and stabilize the cell. The treated cell, which retains the toxic activity, then can be applied to the environment of the target pest.

Where the B.t. toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type indigenous microorganisms, provide for stable maintenance and expression of the gene encoding the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g. genera *Pseudomonas, Erwinia, Serratia, Klebsiella, Xanthomonas, Streptomyces, Rhizobium, Sinorhizobium, Rhodopseudomonas, Methylophilius, Agrobacterium, Acetobacter, Lactobacillus, Arthrobacter, Azotobacter, Leuconostoc*, and *Alcaligenes*; fungi, particularly yeast, e.g. genera *Saccharomyces, Cryptococcus, Kluyveromyces, Sporobolomyces, Rhodotorula*, and *Aureobasidium*. Of particular interest are such phytosphere bacterial species as *Pseudomonas syringae, Pseudomonas fluorescens, Serratia marcescens, Acetobacter xylinum, Agrobacterium tumefaciens, Agrobacterium radiobacter, Rhodopseudomonas spheroides, Xanthomonas campestris, Sinorhizobium meliloti* (formerly *Rhizobium meliloti*), *Alcaligenes eutrophus*, and *Azotobacter vinelandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae*, and *Aureobasidium pollulans*. Of particular interest are the pigmented microorganisms.

Methods of Controlling Insect Pests When an insect comes into contact with an effective amount of toxin delivered via transgenic plant expression, formulated protein compositions(s), sprayable protein composition(s), a bait matrix or other delivery system, the results are typically death of the insect, or the insects do not feed upon the source which makes the toxins available to the insects.

The subject protein toxins can be "applied" or provided to contact the target insects in a variety of ways. For example, transgenic plants (wherein the protein is produced by and present in the plant) can be used and are well-known in the art. Expression of the toxin genes can also be achieved selectively in specific tissues of the plants, such as the roots, leaves, etc. This can be accomplished via the use of tissue-specific promoters, for example. Spray-on applications are another example and are also known in the art. The subject proteins can be appropriately formulated for the desired end use, and then sprayed (or otherwise applied) onto the plant and/or around the plant/to the vicinity of the plant to be protected—before an infestation is discovered, after target insects are discovered, both before and after, and the like. Bait granules, for example, can also be used and are known in the art.

Transgenic Plants

The subject proteins can be used to protect practically any type of plant from damage by a Lepidopteran insect. Examples of such plants include maize, sunflower, soybean, cotton, canola, rice, sorghum, tobacco, wheat, barley, vegetables, ornamentals, peppers (including hot peppers), sugar beets, fruit, and turf, to name but a few. Methods for transforming plants are well known in the art, and illustrative transformation methods are described in the Examples.

A preferred embodiment of the subject invention is the transformation of plants with genes encoding the subject insecticidal protein or its variants. The transformed plants are resistant to attack by an insect target pest by virtue of the presence of controlling amounts of the subject insecticidal protein or its variants in the cells of the transformed plant. By incorporating genetic material that encodes the insecticidal properties of the B.t. insecticidal toxins into the genome of a plant eaten by a particular insect pest, the adult or larvae would die after consuming the food plant. Numerous members of the monocotyledonous and dicotyledonous classifications have been transformed. Transgenic agronomic crops as well as fruits and vegetables are of commercial interest. Such crops include but are not limited to maize, rice, soybeans, canola, sunflower, alfalfa, sorghum, wheat, cotton, peanuts, tomatoes, potatoes, and the like. Several techniques exist for introducing foreign genetic material into plant cells, and for obtaining plants that stably maintain and express the introduced gene. Such techniques include acceleration of genetic material coated onto microparticles directly into cells (U.S. Pat. No. 4,945,050 and U.S. Pat. No. 5,141,131). Plants may be transformed using *Agrobacterium* technology, see U.S. Pat. No. 5,177,010, U.S. Pat. No. 5,104,310, European Patent Application No. 0131624B1, European Patent Application No. 120516, European Patent Application No. 159418B1, European Patent Application No. 176112, U.S. Pat. No. 5,149,645, U.S. Pat. No. 5,469,976, U.S. Pat. No. 5,464,763, U.S. Pat. No. 4,940,838, U.S. Pat. No. 4,693,976, European Patent Application No. 116718, European Patent Application No. 290799, European Patent Application No. 320500, European Patent Application No. 604662, European Patent Application No. 627752, European Patent Application No. 0267159, European Patent Application No. 0292435, U.S. Pat. No. 5,231,019, U.S. Pat. No. 5,463,174, U.S. Pat. No. 4,762,785, U.S. Pat. No. 5,004,863, and U.S. Pat. No. 5,159,135. Other transformation technology includes WHISKERS™ technology, see U.S. Pat. No. 5,302,523 and U.S. Pat. No. 5,464,765. Electroporation technology has also been used to transform plants, see WO 1987/06614, U.S. Pat. No. 5,472,869, U.S. Pat. No. 5,384,253, WO 1992/09696, and WO 1993/21335. All of these transformation patents and publications are incorporated herein by reference. In addition to numerous technologies for transforming plants, the type of tissue which is contacted with the foreign genes may vary as well. Such tissue would include but would not be limited to embryogenic tissue, callus tissue type I and II, hypocotyl, meristem, and the like. Almost all plant tissues may be transformed during dedifferentiation using appropriate techniques within the skill of an artisan.

Genes encoding DIG-109 or DIG-152 toxins or variants thereof can be inserted into plant cells using a variety of techniques which are well known in the art as disclosed above. For example, a large number of cloning vectors comprising a marker that permits selection of the transformed microbial cells and a replication system functional in *Escherichia coli* are available for preparation and modification of foreign genes for insertion into higher plants. Such manipulations may include, for example, the insertion of mutations, truncations, additions, or substitutions as desired for the intended use. The vectors comprise, for example, pBR322, pUC series, M13mp series, pACYC184, etc. Accordingly, the sequence encoding the Cry protein or variants can be inserted into the vector at a suitable restriction site. The resulting plasmid is used for transformation of *E. coli*, the cells of which are cultivated in a suitable nutrient medium, then harvested and lysed so that workable quantities of the plasmid are recovered. Sequence analysis, restriction fragment analysis, electrophoresis, and other biochemical-molecular biological methods are generally carried out as methods of analysis. After each manipulation, the DNA sequence used can be cleaved and joined to the next DNA sequence. Each manipulated DNA sequence can be cloned in the same or other plasmids.

The use of T-DNA-containing vectors for the transformation of plant cells has been intensively researched and sufficiently described in European Patent Application No. 120516; Lee and Gelvin (2008), Fraley et al., (1986), and An et al., (1985), and is well established in the field.

Once the inserted DNA has been integrated into the plant genome, it is relatively stable throughout subsequent generations. The vector used to transform the plant cell normally contains a selectable marker gene encoding a protein that confers on the transformed plant cells resistance to a herbicide or an antibiotic, such as bialaphos, kanamycin, G418, bleomycin, or hygromycin, inter alia. The individually employed selectable marker gene should accordingly permit the selection of transformed cells while the growth of cells that do not contain the inserted DNA is suppressed by the selective compound.

A large number of techniques are available for inserting DNA into a host plant cell. Those techniques include transformation with T-DNA delivered by *Agrobacterium tumefaciens* or *Agrobacterium rhizogenes* as the transformation agent. Additionally, fusion of plant protoplasts with liposomes containing the DNA to be delivered, direct injection of the DNA, biolistics transformation (microparticle bombardment), or electroporation, as well as other possible methods, may be employed.

In a preferred embodiment of the subject invention, plants will be transformed with genes wherein the codon usage of the protein coding region has been optimized for plants. See, for example, U.S. Pat. No. 5,380,831, which is hereby incorporated by reference. Also, advantageously, plants encoding a truncated toxin will be used. The truncated toxin typically will encode about 55% to about 80% of the full length toxin. Methods for creating synthetic B.t. genes for use in plants are known in the art (Stewart 2007).

Regardless of transformation technique, the gene is preferably incorporated into a gene transfer vector adapted to express the B.t. insecticidal toxin genes and variants in the plant cell by including in the vector a plant promoter. In addition to plant promoters, promoters from a variety of sources can be used efficiently in plant cells to express foreign genes. For example, promoters of bacterial origin, such as the octopine synthase promoter, the nopaline synthase promoter, the mannopine synthase promoter; promoters of plant viral origin, such as the 35S and 19S promoters of cauliflower mosaic virus, and the like may be used. Plant promoters include, but are not limited to ribulose-1,6-bisphosphate (RUBP) carboxylase small subunit (ssu), beta-conglycinin promoter, phaseolin promoter, ADH (alcohol dehydrogenase) promoter, heat-shock promoters, ADF (actin depolymerization factor) promoter, and tissue specific promoters. Promoters may also contain certain enhancer sequence elements that may improve the transcription efficiency. Typical enhancers include but are not limited to ADH1-intron 1 and ADH1-intron 6. Constitutive promoters may be used. Constitutive promoters direct continuous gene expression in nearly all cells types and at nearly all times (e.g. actin, ubiquitin, CaMV 35S). Tissue specific promoters are responsible for gene expression in specific cell or tissue types, such as the leaves or seeds (e.g., zein, oleosin, napin, ACP (Acyl Carrier Protein)), and these promoters may also be used. Promoters may also be used that are active during a certain stage of the plants' development as well as active in specific plant tissues and organs. Examples of such promoters include but are not limited to promoters that are root specific, pollen-specific, embryo specific, corn silk specific, cotton fiber specific, seed endosperm specific, phloem specific, and the like.

Under certain circumstances it may be desirable to use an inducible promoter. An inducible promoter is responsible for expression of genes in response to a specific signal, such as: physical stimulus (e.g. heat shock genes); light (e.g. RUBP carboxylase); hormone (e.g. glucocorticoid); antibiotic (e.g. tetracycline); metabolites; and stress (e.g. drought). Other desirable transcription and translation elements that function in plants may be used, such as 5' untranslated leader sequences, RNA transcription termination sequences and poly-adenylate addition signal sequences. Numerous plant-specific gene transfer vectors are known to the art.

Transgenic crops containing insect resistance (IR) traits are prevalent in corn and cotton plants throughout North America, and usage of these traits is expanding globally. Commercial transgenic crops combining IR and herbicide tolerance (HT) traits have been developed by multiple seed companies. These include combinations of IR traits conferred by B.t. insecticidal proteins and HT traits such as tolerance to Acetolactate Synthase (ALS) inhibitors such as sulfonylureas, imidazolinones, triazolopyrimidine, sulfonanilides, and the like, Glutamine Synthetase (GS) inhibitors such as bialaphos, glufosinate, and the like, 4-HydroxyPhenylPyruvate Dioxygenase (HPPD) inhibitors such as mesotrione, isoxaflutole, and the like, 5-EnolPyruvylShikimate-3-Phosphate Synthase (EPSPS) inhibitors such as glyphosate and the like, and Acetyl-Coenzyme A Carboxylase (ACCase) inhibitors such as haloxyfop, quizalofop, diclofop, and the like. Other examples are known in which transgenically provided proteins provide plant tolerance to herbicide chemical classes such as phenoxy acids herbicides and pyridyloxyacetates auxin herbicides (see WO 2007/053482 A2), or phenoxy acids herbicides and aryloxyphenoxypropionates herbicides (see WO 2005107437 A2, A3). The ability to control multiple pest problems through IR traits is a valuable commercial product concept, and the convenience of this product concept is enhanced if insect control traits and weed control traits are combined in the same plant. Further, improved value may be obtained via single plant combinations of IR traits conferred by a B.t. insecticidal protein such as that of the subject invention with one or more additional HT traits such as those mentioned above, plus one or more additional input traits (e.g. other insect resistance conferred by B.t.-derived or other insecticidal proteins, insect resistance conferred by mechanisms such as RNAi and the like, nematode resistance conferred by B.t.-derived or other nematicidal proteins, nematode resistance conferred by mechanisms such as RNAi and the like, disease resistance, stress tolerance, improved nitrogen utilization, and the like), or output traits (e.g. high oils content, healthy oil composition, nutritional improvement, and the like). Such combinations may be obtained either through conventional breeding (breeding stack) or jointly as a novel transformation event involving the simultaneous introduction of multiple genes (molecular stack). Benefits include the ability to manage insect pests and improved weed control in a crop plant that provides secondary benefits to the producer and/or the consumer. Thus, the subject invention can be used in combination with other traits to provide a complete agronomic package of improved crop quality with the ability to flexibly and cost effectively control any number of agronomic issues.

Target Pests

The DIG-109 toxin and the DIG-152 toxin of the invention are particularly suitable for use in control of Lepidopteran insects. Lepidopterans are an important group of agricultural, horticultural, and household pests which cause a very large amount of damage each year. This insect order encompasses foliar- and root-feeding larvae and adults. Lepidopteran insect pests include, but are not limited to: *Achoroia grisella, Acleris gloverana, Acleris variana, Adoxophyes orana, Agrotis ipsilon* (black cutworm), *Alabama argillacea, Alsophila pometaria, Amyelois transitella, Anagasta kuehniella, Anarsia lineatella, Anisota senatoria, Antheraea pernyi, Anticarsia gemmatalis, Archips* sp., *Argyrotaenia* sp., *Athetis mindara, Bombyx mori, Bucculatrix thurberiella, Cadra cautella, Choristoneura* sp., *Cochylls hospes, Colias eurytheme, Corcyra cephalonica, Cydia latiferreanus, Cydia pomonella, Datana integerrima, Dendrolimus sibericus, Desmia feneralis, Diaphania hyalinata, Diaphania nitidalis, Diatraea grandiosella* (southwestern corn borer), *Diatraea saccharalis* (sugarcane borer), *Ennomos subsignaria, Eoreuma loftini, Esphestia elutella, Erannis tilaria, Estigmene acrea, Eulia salubricola, Eupocoellia ambiguella, Eupoecilia ambiguella, Euproctis chrysorrhoea, Euxoa messoria, Galleria mellonella, Grapholita molesta, Harrisina americana, Helicoverpa subflexa, Helicoverpa zea* (corn earworm), *Heliothis virescens, Hemileuca oliviae, Homoeosoma electellum, Hyphantia cunea, Keiferia lycopersicella, Lambdina fiscellaria fiscellaria, Lambdina fiscellaria lugubrosa, Leucoma salicis, Lobesia botrana, Loxagrotis albicosta* (western bean cutworm), *Loxostege sticticalis, Lymantria dispar, Macalla thyrisalis, Malacosoma* sp., *Mamestra brassicae, Mamestra configurata, Manduca quinquemaculata, Manduca sexta, Maruca testulalis, Melanchra pitta, Operophtera brumata, Orgyia* sp., *Ostrinia nubilalis* (European corn borer), *Paleacrita vernata, Papiapema nebris* (common stalk borer), *Papilio cresphontes, Pectinophora gossypiella, Phryganidia californica, Phyllonorycter blancardella, Pieris napi, Pieris*

*rapae, Plathypena scabra, Platynota flouendana, Platynota stultana, Platyptilia carduidactyla, Plodia interpunctella, Plutella xylostella* (diamondback moth), *Pontia protodice, Pseudaletia unipuncta* (armyworm), *Pseudoplasia includens, Sabulodes aegrotata, Schizura concinna, Sitotroga cerealella, Spilonta ocellana, Spodoptera frugiperda* (fall armyworm), *Spodoptera exigua* (beet armyworm), *Thaurnstopoea pityocampa, Ensola bisselliella, Trichoplusia ni, Udea rubigalis, Xylomyges curiails,* and *Yponomeuta padella.*

Use of the DIG-109 toxin and the DIG-152 toxin, and variants thereof, to control Coleopteran pests of crop plants is also contemplated. In some embodiments, Cry proteins may be economically deployed for control of insect pests that include but are not limited to, for example, rootworms such as *Diabrotica undecimpunctata howardi* (southern corn rootworm), *Diabrotica longicornis barberi* (northern corn rootworm), and *Diabrotica virgifera* (western corn rootworm), and grubs such as the larvae of *Cyclocephala borealis* (northern masked chafer) *Cyclocephala immaculate* (southern masked chafer), and *Popillia japonica* (Japanese beetle).

Antibody Detection of DIG-109 and DIG-152 Toxins

Anti-Toxin Antibodies.

Antibodies to the B.t. toxins disclosed herein, or to equivalent toxins, or fragments of these toxins, can readily be prepared using standard procedures in this art, as taught, for example by Coligan et al., 2007 and updates thereof. Such antibodies are useful to detect the presence of the DIG-109 toxin, the DIG-152 toxin, and variants thereof.

Once the B.t. insecticidal toxin has been isolated, antibodies specific for the toxin may be raised by conventional methods that are well known in the art. Repeated injections into a host of choice over a period of weeks or months will elicit an immune response and result in significant anti-B.t. toxin serum titers. Preferred hosts are mammalian species and more highly preferred species are rabbits, goats, sheep and mice. Blood drawn from such immunized animals may be processed by established methods to obtain antiserum (polyclonal antibodies) reactive with the B.t. insecticidal toxin. The antiserum may then be affinity purified by adsorption to the toxin according to techniques known in the art. Affinity purified antiserum may be further purified by isolating the immunoglobulin fraction within the antiserum using procedures known in the art. The resulting material will be a heterogeneous population of immunoglobulins reactive with the B.t. insecticidal toxin.

Anti-B.t. toxin antibodies may also be generated by preparing a semi-synthetic immunogen consisting of a synthetic peptide fragment of the B.t. insecticidal toxin conjugated to an immunogenic carrier. Numerous schemes and instruments useful for making peptide fragments are well known in the art. Many suitable immunogenic carriers such as bovine serum albumin or Keyhole Limpet Hemocyanin are also well known in the art, as are techniques for coupling the immunogen and carrier proteins. Once the semi-synthetic immunogen has been constructed, the procedure for making antibodies specific for the B.t. insecticidal toxin fragment is identical to those used for making antibodies reactive with natural B.t. toxin.

Anti-B.t. toxin monoclonal antibodies (MAbs) are readily prepared using purified B.t. insecticidal toxin. Methods for producing MAbs have been practiced for over 15 years and are well known to those of ordinary skill in the art. Repeated intraperitoneal or subcutaneous injections of purified B.t. insecticidal toxin in adjuvant will elicit an immune response in most animals. Hyperimmunized B-lymphocytes are removed from the animal and fused with a suitable fusion partner cell line capable of being cultured indefinitely. Preferred animals whose B-lymphocytes may be hyperimmunized and used in the production of MAbs are mammals. More preferred animals are rats and mice and most preferred is the BALB/c mouse strain.

Numerous mammalian cell lines are suitable fusion partners for the production of hybridomas. Many such lines are available from the American Type Culture Collection (ATCC, Manassas, Va.) and commercial suppliers. Preferred fusion partner cell lines are derived from mouse myelomas and the HL-1® Friendly myeloma-653 cell line (Ventrex, Portland, Me.) is most preferred. Once fused, the resulting hybridomas are cultured in a selective growth medium for one to two weeks. Two well known selection systems are available for eliminating unfused myeloma cells, or fusions between myeloma cells, from the mixed hybridoma culture. The choice of selection system depends on the strain of mouse immunized and myeloma fusion partner used. The aaT selection system, described by Taggart and Samloff, (1983), may be used; however, the HAT (hypoxanthine, aminopterin, thymidine) selection system, described by Littlefield (1964), is preferred because of its compatibility with the preferred mouse strain and fusion partner mentioned above. Spent growth medium is then screened for immunospecific MAb secretion. Enzyme linked immunosorbent assay (ELISA) procedures are best suited for this purpose; though, radioimmunoassays adapted for large volume screening are also acceptable. Multiple screens designed to consecutively pare down the considerable number of irrelevant or less desired cultures may be performed. Cultures that secrete MAbs reactive with the B.t. insecticidal toxin may be screened for cross-reactivity with known B.t. insecticidal toxins. MAbs that preferentially bind to the preferred B.t. insecticidal toxin may be isotyped using commercially available assays. Preferred MAbs are of the IgG class, and more highly preferred MAbs are of the $IgG_1$ and $IgG_{2a}$ subisotypes.

Hybridoma cultures that secrete the preferred MAbs may be sub-cloned several times to establish monoclonality and stability. Well known methods for sub-cloning eukaryotic, non-adherent cell cultures include limiting dilution, soft agarose and fluorescence activated cell sorting techniques. After each subcloning, the resultant cultures preferably are re-assayed for antibody secretion and isotype to ensure that a stable preferred MAb-secreting culture has been established.

The anti-B.t. toxin antibodies are useful in various methods of detecting the claimed B.t. insecticidal toxin of the instant invention, and variants or fragments thereof. It is well known that antibodies labeled with a reporting group can be used to identify the presence of antigens in a variety of milieus. Antibodies labeled with radioisotopes have been used for decades in radioimmunoassays to identify, with great precision and sensitivity, the presence of antigens in a variety of biological fluids. More recently, enzyme labeled antibodies have been used as a substitute for radiolabeled antibodies in the ELISA assay. Further, antibodies immunoreactive to the B.t. insecticidal toxin of the present invention can be bound to an immobilizing substance such as a polystyrene well or particle and used in immunoassays to determine whether the B.t. toxin is present in a test sample.

Detection Using Probes

A further method for identifying the toxins and genes of the subject invention is through the use of oligonucleotide probes. These probes are detectable nucleotide sequences. These sequences may be rendered detectable by virtue of an appropriate radioactive label or may be made inherently fluorescent as described in U.S. Pat. No. 6,268,132. As is well known in the art, if the probe molecule and nucleic acid sample hybridize by forming strong base-pairing bonds between the two molecules, it can be reasonably assumed that the probe and sample have substantial sequence homology. Preferably, hybridization is conducted under stringent conditions by techniques well-known in the art, as described, for example, in Keller and Manak (1993). Detection of the probe provides a means for determining in a known manner whether hybridization has occurred. Such a probe analysis provides a rapid method for identifying toxin-encoding genes of the subject invention. The nucleotide segments which are used as probes according to the invention can be synthesized using a DNA synthesizer and standard procedures. These nucleotide sequences can also be used as PCR primers to amplify genes of the subject invention.

Hybridization

As is well known to those skilled in molecular biology, similarity of two nucleic acids can be characterized by their tendency to hybridize. As used herein the terms "stringent conditions" or "stringent hybridization conditions" are intended to refer to conditions under which a probe will hybridize (anneal) to its target sequence to a detectably greater degree than to other sequences (e.g. at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to pH 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide. Exemplary low stringency conditions include hybridization with a buffer solution of 30% to 35% formamide, 1 M NaCl, 1% SDS (sodium dodecyl sulfate) at 37° C. and a wash in 1× to 2×SSC (20×SSC=3.0 M NaCl/0.3 M trisodium citrate) at 50° C. to 55° C. Exemplary moderate stringency conditions include hybridization in 40% to 45% formamide, 1.0 M NaCl, 1% SDS at 37° C. and a wash in 0.5× to 1×SSC at 55° C. to 60° C. Exemplary high stringency conditions include hybridization in 50% formamide, 1 M NaCl, 1% SDS at 37° C. and a wash in 0.1×SSC at 60° C. to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the most important factors being the ionic strength and temperature of the final wash solution. For DNA/DNA hybrids, the thermal melting point ($T_m$) is the temperature (under defined ionic strength and pH) at which 50% of a complementary target sequence hybridizes to a perfectly matched probe. $T_m$ is reduced by about 1° C. for each 1% of mismatching; thus, $T_m$, hybridization conditions, and/or wash conditions can be adjusted to facilitate annealing of sequences of the desired identity. For example, if sequences with >90% identity are sought, the T. can be decreased 10° C. Generally, stringent conditions are selected to be about 5° C. lower than the T. for the specific sequence and its complement at a defined ionic strength and pH. However, highly stringent conditions can utilize a hybridization and/or wash at 1° C., 2° C., 3° C., or 4° C. lower than the $T_m$; moderately stringent conditions can utilize a hybridization and/or wash at 6° C., 7° C., 8° C., 9° C., or 10° C. lower than the $T_m$, and low stringency conditions can utilize a hybridization and/or wash at 11° C., 12° C., 13° C., 14° C., 15° C., or 20° C. lower than the $T_m$.

$T_m$ (in ° C.) may be experimentally determined or may be approximated by calculation. For DNA-DNA hybrids, the T. can be approximated from the equation of Meinkoth and Wahl (1984):

$$T_m(° C.)=81.5° C.+16.6(\log M)+0.41(\% GC)-0.61(\% \text{formamide})-500/L;$$

where M is the molarity of monovalent cations, % GC is the percentage of guanosine and cytosine nucleotides in the DNA, % formamide is the percentage of formamide in the hybridization solution, and L is the length of the hybrid in base pairs Alternatively, the T. is described by the following formula (Beltz et al., 1983).

$$T_m(° C.)=81.5° C.+16.6(\log [Na+])+0.41(\% GC)-0.61(\% \text{formamide})-600/L$$

where [Na+] is the molarity of sodium ions, % GC is the percentage of guanosine and cytosine nucleotides in the DNA, % formamide is the percentage of formamide in the hybridization solution, and L is the length of the hybrid in base pairs Using the equations, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) and Ausubel et al., 1995 and updates thereof). Also see Sambrook et al., (1989) and updates thereof.

Hybridization of immobilized DNA on Southern blots with radioactively labeled gene-specific probes may be performed by standard methods Sambrook et al., supra.). Radioactive isotopes used for labeling polynucleotide probes may include 32P, 33P, 14C, or 3H. Incorporation of radioactive isotopes into polynucleotide probe molecules may be done by any of several methods well known to those skilled in the field of molecular biology. (See, e.g. Sambrook et al., supra.) In general, hybridization and subsequent washes may be carried out under stringent conditions that allow for detection of target sequences with homology to the claimed toxin encoding genes. For double-stranded DNA gene probes, hybridization may be carried out overnight at 20-25° C. below the $T_m$ of the DNA hybrid in 6×SSPE, 5×Denhardt's Solution, 0.1% SDS, 0.1 mg/mL denatured DNA [20×SSPE is 3M NaCl, 0.2 M NaHPO$_4$, and 0.02M EDTA (ethylenediamine tetra-acetic acid sodium salt); 100×Denhardt's Solution is 20 gm/L Polyvinylpyrollidone, 20 gm/L Ficoll type 400 and 20 gm/L Bovine Serum Albumin (fraction V)].

Washes may typically be carried out as follows:
 Twice at room temperature for 15 minutes in 1×SSPE, 0.1% SDS (lower stringency wash).
 Once at $T_m$−20° C. for 15 minutes in 0.2×SSPE, 0.1% SDS (higher stringency wash).

For oligonucleotide probes, hybridization may be carried out overnight at 10-20° C. below the $T_m$ of the hybrid in 6×SSPE, 5×Denhardt's solution, 0.1% SDS, 0.1 mg/mL denatured DNA. $T_m$ for oligonucleotide probes may be determined by the following formula (Suggs et al., 1981).

$$T_m(°C.)=2(\text{number of } T/A \text{ base pairs})+4(\text{number of } G/C \text{ base pairs})$$

Washes may typically be carried out as follows:
Twice at room temperature for 15 minutes 1×SSPE, 0.1% SDS (lower stringency wash).
Once at the hybridization temperature for 15 minutes in 1×SSPE, 0.1% SDS (higher stringency wash).
Some examples of salt concentrations and temperature combinations are as follows (in order of increasing stringency): 2×SSPE or SSC at room temperature; 1×SSPE or SSC at 42° C.; 0.1×SSPE or SSC at 42° C.; 0.1×SSPE or SSC at 65° C.

Probe molecules for hybridization and hybrid molecules formed between probe and target molecules may be rendered detectable by means other than radioactive labeling. Such alternate methods are intended to be within the scope of this invention.

It should be understood that the examples and embodiments described herein are for illustrative purposes only and that various modifications or changes in light thereof will be suggested to persons skilled in the art and are to be included within the spirit and purview of this application and the scope of the appended claims.

Unless specifically indicated or implied, the terms "a", "an", and "the" signify "at least one" as used herein.

Following are examples that illustrate procedures for practicing the invention. These examples should not be construed as limiting. All percentages are by weight and all solvent mixture proportions are by volume unless otherwise noted. All temperatures are in degrees Celsius.

EXAMPLE 1

Design of Chimeric Cry1Ca Core Toxins and Cry1Ab Protoxins

Chimeric Toxins.

Chimeric proteins utilizing the core toxin domain of one Cry toxin fused to the protoxin segment of another Cry toxin have previously been reported, for example, in U.S. Pat. No. 5,593,881 and U.S. Pat. No. 5,932,209. A Cry1Ca3 delta endotoxin protein sequence is deposited as GenBank Accession Number AAA22343 under an obsolete terminology of Cry1C(b).

Cry1Ca chimeric protein variants of this invention include toxins comprising an N-terminal core toxin segment derived from a Cry1Ca3 insecticidal toxin fused to a heterologous delta endotoxin protoxin segment at some point past the end of the core toxin segment. The transition from the core toxin to the heterologous protoxin segment can occur at approximately the native core toxin/protoxin junction or, in the alternative, a portion of the native protoxin (extending past the core toxin segment) can be retained, with the transition to the heterologous protoxin occurring downstream. In variant fashion, the core toxin and protoxin segments may comprise exactly the amino acid sequence of the native toxins from which they are derived, or may include amino acid additions, deletions, or substitutions that do not diminish, and may enhance, the biological function of the segments when fused to one another.

For example, a chimeric toxin of the subject invention comprises a core toxin segment derived from Cry1Ca3 and a heterologous protoxin. In a preferred embodiment of the invention, the core toxin segment derived from Cry1Ca3, and disclosed as the Cry1Ca core toxin segment in SEQ ID NO:1 (619 amino acids), is fused to a heterologous segment comprising a protoxin segment derived from a Cry1Ab delta-endotoxin. SEQ ID NO:2 discloses the 545 amino acid sequence of one protoxin segment derived from Cry1Ab and useful in Cry1Ca variants of the invention. Attention is drawn to the last about 100 to 150 amino acids of this protoxin segment of SEQ ID NO:2, which is important to include in the chimeric toxin of the subject invention. Accordingly, a preferred embodiment of the invention comprises a chimeric protein in which the Cry1Ca core toxin segment disclosed as SEQ ID NO:1 is joined to the protoxin segment derived from Cry1Ab as disclosed in SEQ ID NO:2. The 1164 amino acid sequence of the chimeric protein, herein referred to as DIG-152, is disclosed as SEQ ID NO:3 (pMYC2547 version). A second preferred embodiment of the invention comprises a chimeric protein in which the Cry1Ca core toxin segment disclosed as SEQ ID NO:1 is joined to a second 545 amino acid protoxin segment derived from Cry1Ab as presented in SEQ ID NO:4. Attention is drawn to the last about 100 to 150 amino acids of this protoxin segment, which is important to include in the chimeric toxin of the subject invention. The 1164 amino acid sequence of the second chimeric protein, referred to as DIG-109, is disclosed as SEQ ID NO:5 (maize optimized version). It is to be understood that other chimeric fusions comprising Cry1Ca core toxin variants and protoxins derived from Cry1Ab are within the scope of this invention.

It is noted that the protoxin segments derived from Cry1Ab as presented in SEQ ID NO:2 and SEQ ID NO:4 are essentially functional equivalents of one another, differing in sequence only at a single (the first) position.

EXAMPLE 2

Construction of Expression Plasmids Encoding Chimeric Cry1Ca Core/Cry1Ab Protoxin Proteins and Expression in *Pseudomonas*

Standard cloning methods [as described in, for example, Sambrook et al., (1989) and Ausubel et al., (1995), and updates thereof] were used in the construction of *Pseudomonas fluorescens* (PD expression construct pMYC2547 engineered to produce a full-length chimeric protein comprised of a Cry1Ca core fused to a Cry1Ab protoxin (DIG-152; SEQ ID NO:3). Protein production was performed in *Pseudomonas fluorescens* strain MB214 (a derivative of strain MB101; *P. fluorescens* biovar I), having an insertion of a modified lac operon as disclosed in U.S. Pat. No. 5,169,760. The basic cloning strategy entailed subcloning a DNA fragment encoding DIG-152 into plasmid vectors, whereby it is placed under the expression control of the Ptac promoter and the rrnBT1T2 terminator from plasmid pKK223-3 (PL Pharmacia, Milwaukee, Wis.). One such plasmid was named pMYC2547, and the MB214 isolate harboring this plasmid is named Dpf108.

Growth and Expression Analysis in Shake Flasks

Production of DIG-152 protein for characterization and insect bioassay was accomplished by shake-flask-grown *P. fluorescens* strain Dpf108. DIG-152 protein production driven by the Ptac promoter was conducted as described previously in U.S. Pat. No. 5,527,883. Expression was induced by addition of isopropyl-β-D-1-thiogalactopyranoside (IPTG) after an initial incubation of 24 hours at 30° with shaking. Cultures were sampled at the time of induction and at various times post-induction. Cell density was measured by optical density at 600 nm ($OD_{600}$).

Cell Fractionation and SDS-PAGE Analysis of Shake Flask Samples

At each sampling time, the cell density of samples was adjusted to $OD_{600}=20$ and 1 mL aliquots were centrifuged at 14000×g for five minutes. The cell pellets were frozen at −80°. Soluble and insoluble fractions from frozen shake flask cell pellet samples were generated using EasyLyse™ Bacterial Protein Extraction Solution (EPICENTRE® Biotechnologies, Madison, Wis.). Each cell pellet was resuspended in 1 mL EasyLyse™ solution and further diluted 1:4 in lysis buffer and incubated with shaking at room temperature for 30 minutes. The lysate was centrifuged at 14,000 rpm for 20 minutes at 4° and the supernatant was recovered as the soluble fraction. The pellet (insoluble fraction) was then resuspended in an equal volume of phosphate buffered saline (PBS; 11.9 mM $Na_2HPO_4$, 137 mM NaCl, 2.7 mM KCl, pH7.4).

Samples were mixed 1:1 with 2× Laemmli sample buffer containing (3-mercaptoethanol (Sambrook et al., supra.) and boiled for 5 minutes prior to loading onto Criterion XT Bis-Tris 12% gels (Bio-Rad Inc., Hercules, Calif.). Electrophoresis was performed in the recommended XT MOPS buffer. Gels were stained with Bio-Safe Coomassie Stain according to the manufacturer's (Bio-Rad) protocol and imaged using the Alpha Innotech Imaging system (San Leandro, Calif.).

Inclusion Body Preparation.

DIG-152 protein inclusion body (IB) preparations were performed on cells from *P. fluorescens* fermentations that produced insoluble B.t. insecticidal protein, as demonstrated by SDS-PAGE and MALDI-MS (Matrix Assisted Laser Desorption/Ionization Mass Spectrometry). *P. fluorescens* fermentation pellets were thawed in a 37° water bath. The cells were resuspended to 25% w/v in lysis buffer [50 mM Tris, pH 7.5, 200 mM NaCl, 20 mM EDTA disodium salt (Ethylenediaminetetraacetic acid), 1% Triton X-100, and 5 mM Dithiothreitol (DTT); 5 mL/L of bacterial protease inhibitor cocktail (Catalog #P8465; Sigma-Aldrich, St. Louis, Mo.) were added just prior to use]. The cells were suspended using a hand-held homogenizer at lowest setting (Tissue Tearor, BioSpec Products, Inc., Bartlesville, Okla.). Lysozyme (25 mg of Sigma L7651, from chicken egg white) was added to the cell suspension by mixing with a metal spatula, and the suspension was incubated at room temperature for one hour. The suspension was cooled on ice for 15 minutes, then sonicated using a Branson Sonifier 250 (two 1-minute sessions, at 50% duty cycle, 30% output). Cell lysis was checked by microscopy. An additional 25 mg of lysozyme were added if necessary, and the incubation and sonication were repeated. Following confirmation of cell lysis via microscopy, the lysate was centrifuged at 11,500×g for 25 minutes (4°) to form the IB pellet, and the supernatant was discarded. The IB pellet was resuspended with 100 mL lysis buffer, homogenized with the hand-held mixer and centrifuged as above. The IB pellet was repeatedly washed by resuspension (in 50 mL lysis buffer), homogenization, sonication, and centrifugation until the supernatant became colorless and the IB pellet became firm and off-white in color. For the final wash, the IB pellet was resuspended in sterile-filtered (0.22 μm) distilled water containing 2 mM EDTA, and centrifuged. The final pellet was resuspended in sterile-filtered distilled water containing 2 mM EDTA, and stored in 1 mL aliquots at −80°.

SDS-PAGE analysis and quantitation of protein in IB preparations was done by thawing a 1 mL aliquot of IB pellet and diluting 1:20 with sterile-filtered distilled water. The diluted sample was then boiled with 4× reducing sample buffer [250 mM Tris, pH6.8, 40% glycerol (v/v), 0.4% Bromophenol Blue (w/v), 8% SDS (w/v) and 8% β-mercaptoethanol (v/v)] and loaded onto a Novex® 4-20% Tris-Glycine, 12+2 well gel (Invitrogen) run with 1× Tris/Glycine/SDS buffer (BioRad). The gel was run for 60 min at 200 volts then stained with Coomassie Blue (50% G-250/50% R-250 in 45% methanol, 10% acetic acid), and destained with 7% acetic acid, 5% methanol in distilled water. Quantification of target bands was done by comparing densitometric values for the bands against Bovine Serum Albumin (BSA) standard samples run on the same gel to generate a standard curve.

Solubilization of Inclusion Bodies. Six mL of DIG-152 inclusion body suspension from Pf clone DPf108 were centrifuged on the highest setting of an Eppendorf model 5415C microfuge (approximately 14,000×g) to pellet the inclusions. The storage buffer supernatant was removed and replaced with 25 mL of 100 mM sodium carbonate buffer, pH 11, in a 50 mL conical tube. Inclusions were resuspended using a pipette and vortexed to mix thoroughly. The tube was placed on a gently rocking platform at 4° overnight to extract the target protein. The extract was centrifuged at 30,000×g for 30 min at 4°, and the resulting supernatant was concentrated 5-fold using an Amicon Ultra-15 regenerated cellulose centrifugal filter device (30,000 Molecular Weight Cutoff; Millipore). The sample buffer was then changed to 10 mM CAPS [3-(cyclohexamino) 1-propanesulfonic acid] pH 10 using disposable PD-10 columns (GE Healthcare, Piscataway, N.J.).

Solubilization and Trypsin Activation of Inclusion Body Protein.

In some instances, DIG-152 inclusion body suspension from Pf clone DPf108 was centrifuged on the highest setting of an Eppendorf model 5415C microfuge (approximately 14,000×g) to pellet the inclusions. The storage buffer supernatant was removed and replaced with 100 mM CAPS, pH 11 to provide a protein concentration of approximately 50 mg/mL. The tube was rocked at room temperature for three hours to completely solubilize the protein. Trypsin was added at an amount equal to 5% to 10% (w:w, based on the initial weight of IB powder) and digestion was accomplished by incubation while rocking overnight at 4° or by rocking 90-120 minutes at room temperature. Insoluble material was removed by centrifugation at 10,000×g for 15 minutes, and the supernatant was applied to a MonoQ anion exchange column (10 mm by 10 cm). Activated DIG-152 protein was eluted (as determined by SDS-PAGE, see below) by a 0% to 100% 1 M NaCl gradient over 25 column volumes. Fractions containing the activated protein were pooled and, when necessary, concentrated to less than 10 mL using an Amicon Ultra-15 regenerated cellulose centrifugal filter device as above. The material was then passed through a Superdex 200 column (16 mm by 60 cm) in buffer containing 100 mM NaCl. 10% glycerol, 0.5% Tween-20 and 1 mM EDTA. It was determined by SDS-PAGE analysis that the activated (enzymatically truncated) protein elutes at 65 to 70 mL. Fractions containing the activated protein were pooled and concentrated using the centrifugal concentrator as above.

Gel Electrophoresis.

The concentrated protein preparations were prepared for electrophoresis by diluting 1:50 in NuPAGE® LDS sample buffer (Invitrogen) containing 5 mM DTT as a reducing agent and heated at 95° for 4 minutes. The sample was loaded in duplicate lanes of a 4-12% NuPAGE® gel alongside five BSA standards ranging from 0.2 μg to 2 μg/lane (for standard curve generation). Voltage was applied at 200 V using MOPS SDS running buffer (Invitrogen) until the tracking dye reached the bottom of the gel. The gel was stained with 0.2% Coomassie Blue G-250 in 45% methanol, 10% acetic acid, and destained, first briefly with 45% methanol, 10% acetic acid, and then at length with 7% acetic acid, 5% methanol until the background cleared. Following destaining, the gel was scanned with a BioRad Fluor-S MultiImager. The instrument's Quantity One Software v.4.5.2 was used to obtain background-subtracted volumes of the stained protein bands and to generate the BSA standard curve that was used to calculate the concentration of chimeric DIG-152 protein in the stock solution.

EXAMPLE 3

Insecticidal Activity of DIG-152 Protein Produced in *Pseudomonas fluorescens*

Insecticidal activity of the DIG-152 protein was demonstrated on Lepidopteran species including the European corn borer (ECB; *Ostrinia nubilalis* (Hübner)), cry1F-resistant ECB (rECB), corn earworm (CEW; *Helicoverpa zea* (Boddie)), black cutworm (BCW; *Agrotis Ipsilon* (Hufnagel)), fall armyworm (FAW, *Spodoptera frugiperda* (J. E. Smith)), Cry1F-resistant FAW (rFAW), and southwestern corn borer (SWCB, *Diatraea grandiosella*).

Sample Preparation and Bioassays.

Inclusion body preparations (native full length protein or trypsin activated protein) were transferred to 10 mM CAPS pH 10 buffer by exchange methods such as dialysis or PD-10 columns. The samples were then diluted appropriately in 10 mM CAPS pH 10, and all bioassays contained a control treatment consisting of this buffer, which served as a background check for mortality or growth inhibition.

Protein concentrations in bioassay buffer were estimated by gel electrophoresis using BSA to create a standard curve for gel densitometry, which was measured using a BioRad imaging system as above. Proteins in the gel matrix were stained with Coomassie Blue-based stain and destained before reading.

Purified proteins were tested for insecticidal activity in bioassays conducted with neonate Lepidopteran larvae on artificial insect diet. Larvae of ECB, CEW, BCW, FAW, and SWCB were hatched from eggs obtained from a colony maintained by a commercial insectary (Benzon Research Inc., Carlisle, Pa.). Larvae of rECB and rFAW were hatched from eggs harvested from proprietary colonies (Dow AgroSciences, Indianapolis, Ind.).

The bioassays were conducted in 128-well plastic trays specifically designed for insect bioassays (C-D International, Pitman, N.J.). Each well contained 1.0 mL of multi-species Lepidoptera diet (Southland Products, Lake Village, Ark.). A 40 μL aliquot of protein sample was delivered by pipette onto the 1.5 cm² diet surface of each well (i.e. 26.7 μL/cm²). Diet concentrations were calculated as the amount (ng) of DIG-152 protein per square centimeter of surface area in the well. The treated trays were held in a fume hood until the liquid on the diet surface had evaporated or was absorbed into the diet.

Within a few hours of eclosion, individual larvae were picked up with a moistened camel hair brush and deposited on the treated diet, one larva per well. The infested wells were then sealed with adhesive sheets of clear plastic, vented to allow gas exchange (C-D International). Bioassay trays were held under controlled environmental conditions [28°, approximately 40% Relative Humidity (RH), 16 hr:8 hr (light:dark)] for 5 days, after which time the total number of insects exposed to each protein sample, the number of dead insects, and the weight of surviving insects were recorded. Percent mortality and percent growth inhibition were calculated for each treatment. Percent growth inhibition (GI) was calculated as follows:

% $GI=[1-(TWIT/TNIT)/(TWIBC/TNIBC)] \times 100$ where

TWIT is the Total Weight of Insects in the Treatment,

TNIT is the Total Number of Insects in the Treatment

TWIBC is the Total Weight of Insects in the Background Check (Buffer control), and TNIBC is the Total Number of Insects in the Background Check (Buffer control).

The $GI_{50}$ was determined to be the concentration of chimeric DIG-152 protein in the diet at which the % GI value was 50. The $LC_{50}$ (50% Lethal Concentration) was recorded as the concentration of DIG-152 protein in the diet at which 50% of test insects were killed. Statistical analysis (One-way ANOVA) was done using JMP software (SAS, Cary, N.C.).

Table 3 presents the results of ingestion bioassays of DIG-152 protein on seven types of test insect larvae.

TABLE 3

| $GI_{50}$ and $LC_{50}$ values (in ng/cm²) calculated from insect diet top loaded with DIG-152 protein. | | | | | | | | | | | | | |
|---|---|---|---|---|---|---|---|---|---|---|---|---|---|
| FAW | | rFAW | | SWCB | | ECB | | rECB | | CEW | | BCW | |
| $GI_{50}$ | $LC_{50}$ | $GI_{50}$ | $LC_{50}$ | $GI_{50}$ | $LC_{50}$ | $GI_{50}$ | $LC_{50}$ | $GI_{50}$ | $LC_{50}$ | $GI_{50}$ | $LC_{50}$ | $GI_{50}$ | $LC_{50}$ |
| 38.1 | 2828.7 | 78.9 | 2210.9 | <47 | >3000 | 1069.0 | >3000 | | >3000 | 2689.4 | >3000 | inactive | |

It is a feature of the DIG-152 protein of the subject invention that the growth of neonate larvae of fall armyworm (*Spodoptera frugiperda*) and southwestern corn borer (*Diatraea grandiosella*) is inhibited following ingestion of the DIG-152 protein. Further, fall armyworm larvae that are resistant to intoxication by Cry1F are as susceptible to DIG-152 activity as are wild-type fall armyworm larvae.

EXAMPLE 4

Further Insecticidal Activity of DIG-152 Protein Produced in *Pseudomonas fluorescens*

Lepidopteran insecticidal activity of the DIG-152 protein (not trypsin activated) was further demonstrated on neonate larvae of sugarcane borer (SCB; *Diatraea saccharalis*) and Cry1Ab-resistant SCB (rSCB) in dose-response experiments utilizing diet incorporation procedures. DIG-152 inclusion bodies were solubilized by rocking gently at 4° for 4 hrs in 7.5 mL of 100 mM CAPS pH11, 1 mM EDTA, to which had been added 200 μL of bacterial protease inhibitor (Sigma P4865; prepared per supplier's instructions). Following centrifugation to pellet the insoluble material, the stock protein concentration was adjusted to 4.0 mg/mL in 100 mM CAPS, pH11. For insect bioassay, DIG-152 protein concentrations in the range of 0.030 μg to 102 μg/gm diet were prepared by mixing appropriate volumes with a meridic diet (Bio-Serv, Frenchtown, N.J.) just prior to dispensing approximately 0.7 mL of the diet into individual cells of 128-cell trays (Bio-Ba-128, C-D International).

Trypsin-activated Cry1Ab protein (used as a positive control for insecticidal activity) was tested in the range of 0.03125 μg to 32 μg/gm diet (prepared by mixing lyophilized powder with appropriate amounts of distilled water before diet preparation).

Diets prepared with distilled water (Blank Control, for Cry1Ab tests) or Buffer Only (100 mM CAPS pH11, for DIG-152 tests) were used as control treatments. One neonate larva of *D. saccharalis* (<24 hr after eclosion) was released on the diet surface in each cell. After larval inoculation, cells were covered with vented lids (C-D International) and the bioassay trays were placed in an environmental chamber maintained at 28°, 50% RH, and a 16 hr:8 hr (light:dark) photoperiod. Larval mortality, larval weight, and number of surviving larvae that did not demonstrate weight gains (<0.1 mg per larva) were recorded on the seventh day after inoculation. Each combination of insect strain/Cry protein concentration was replicated four times, with 16 to 32 larvae in each replicate.

Larval mortality criteria were measured as "practical" mortality, which considered both the Dead (morbid) larvae and the surviving (Stunted, non-feeding) larvae that did not show a significant gain in body weight (i.e. <0.1 mg per larva). The practical mortality of larvae in a treatment was calculated using the equation:

Practical Mortality (%)=[TDS/TNIT]×100 where
TDS is the Total number of Dead larvae plus the number of Stunted larvae,
and TNIT is the Total Number of Insects in the Treatment The "practical" mortality (hereafter simplified as Mortality) of each *D. saccharalis* strain was corrected for larval mortality observed on water Blank Control diet for analyzing results following Cry1Ab treatment, or the Buffer Only-treated diet for the DIG-152 treatment.

The results of the dose response experiments were further analyzed to establish a $GI_{50}$ value, [i.e. the concentration of B.t. protein in the diet at which the larval growth inhibition (% GI) value was 50]. The % GI value of larvae on diet containing Cry1Ab-protein was calculated using the formula:

% GI=[TWC−TWT]/TWC×100 where
TWC is the Total body Weight of larvae feeding on water Control diet, and
TWT is the Total body Weight of larvae feeding on Cry1Ab Treated diet
whereas, for analyzing larval % GI as a result of DIG-152 protein ingestion, it was calculated using the formula:

% GI=[TWB−TWT]/TWB×100 where
TWB is the Total body Weight of larvae feeding on Buffer-Only control treated diet, and
TWT is the Total body Weight of larvae feeding on DIG-152 Treated diet A larval growth inhibition of 100% was assigned to a replication if there were no larvae that had significant weight gain (<0.1 mg per larva). The growth inhibition data were analyzed using a two-way ANOVA with insect strain and Cry protein concentration as the two main factors. LSMEANS tests were used to determine treatment differences at the α=0.05 level.

The results of the diet-incorporation bioassays on *Diatraea saccharalis* larvae are given in Table 4.

TABLE 4

Dose response larval mortality and growth inhibition (% mean ± sem) of Cry1Ab - susceptible (SCB) and Cry1Ab-resistant (rSCB) *Diatraea saccharalis* feeding on diet containing Cry1Ab or DIG-152 protein[a]

| | Cry1Ab protein | | | | DIG-152 | | | |
|---|---|---|---|---|---|---|---|---|
| Insect | protein conc'n[b] | # larvae | Mortality[c] | % GI[d] | protein conc'n[b] | # larvae | Mortality[c] | % GI[e] |
| SCB | Blank | 126 | 3.2 ± 1.3 a | — | Blank | 124 | 10.4 ± 3.2 b | 5.9 ± 4.8 a |
| rSCB | Blank | 128 | 4.7 ± 2.0 a | — | Blank | 125 | 4.1 ± 2.5 a | 3.1 ± 5.5 a |
| SCB | Buffer | NT[f] | | | Buffer | 121 | 10.9 ± 3.9 b | — |
| rSCB | Buffer | NT | | | Buffer | 127 | 1.6 ± 0.9 a | — |
| SCB | 0.03125 | 124 | 38.6 ± 4.8 c | 90.7 ± 1.6 ef | 0.03 | 126 | 53.1 ± 2.3 c | 69.5 ± 6.5 c |
| rSCB | 0.03125 | 123 | 8.3 ± 3.2 ab | −15.9 ± 4.6 a | 0.03 | 127 | 3.2 ± 0.0 a | 8.0 ± 5.1 a |
| SCB | 0.125 | 128 | 34.3 ± 7.9 c | 87.4 ± 2.5 e | 0.1 | 127 | 88.2 ± 3.5 d | 100 ± 0.0 d |
| rSCB | 0.125 | 126 | 8.6 ± 2.3 ab | 10.0 ± 5.3 b | 0.1 | 127 | 11.8 ± 0.8 b | 49.0 ± 3.5 b |
| SCB | 0.5 | 119 | 75.6 ± 2.9 e | 94.3 ± 1.0 fg | 0.4 | 130 | 96.2 ± 1.9 e | 100 ± 0.0 d |
| rSCB | 0.5 | 128 | 5.5 ± 1.5 a | 26.7 ± 3.1 c | 0.4 | 125 | 91.2 ± 2.0 d | 100 ± 0.0 d |
| SCB | 2 | 125 | 93.6 ± 2.2 f | 100 ± 0.0 g | 1.6 | 122 | 100 ± 0.0 f | 100 ± 0.0 d |
| rSCB | 2 | 128 | 14.8 ± 2.7 b | 67.5 ± 1.5 d | 1.6 | 127 | 100 ± 0.0 f | 100 ± 0.0 d |
| SCB | 8 | 122 | 95.9 ± 1.6 fg | 100 ± 0.0 g | 6.4 | 125 | 100 ± 0.0 f | 100 ± 0.0 d |
| rSCB | 8 | 120 | 40.6 ± 5.1 c | 85.2 ± 1.9 e | 6.4 | 128 | 100 ± 0.0 f | 100 ± 0.0 d |
| SCB | 32 | 126 | 99.2 ± 0.8 g | 100 ± 0.0 g | 25.6 | 78 | 100 ± 0.0 f | 100 ± 0.0 d |
| rSCB | 32 | 128 | 60.9 ± 5.8 d | 90.3 ± 2.2 ef | 25.6 | 119 | 100 ± 0.0 f | 100 ± 0.0 d |
| SCB | | | | | 102 | 60 | 100 ± 0.0 f | 100 ± 0.0 d |
| rSCB | | | | | 102 | 126 | 100 ± 0.0 f | 100 ± 0.0 d |

[a]Mean values within a column across all treatments followed by a same letter are not significantly different (P < 0.05; LSMEANS test). sem = standard error of the mean
[b]μg protein/gm diet
[c]The measure of larval mortality was as defined in the text.
[d]These percent values were calculated using the formula described in the text.
[e]These percent values were calculated using the formula described in the text.
[f]NT = Not Tested Data Analysis Corrected dose/mortality data then were subjected to probit analysis for determining treatment protein concentrations that caused a 50% mortality ($LC_{50}$) value and the corresponding 95% confidence intervals (CI). The treatments used in the probit analysis included the highest concentration that produced zero mortality, the lowest concentration that resulted in 100% mortality, and all results between those extremes. Resistance ratios were calculated by dividing the $LC_{50}$ value of the rSCB strain by that of the SCB insects. A lethal dose ratio test was used to determine if the resistance ratios were significant at α=0.05 level. A two-way ANOVA also was used to analyze the mortality data, followed by the LSMEANS test at the α=0.05 level to determine treatment differences. The results of the analyses are presented in Table 5.

TABLE 5

Summary of bioassay tests on larvae of SCB and rSCB using insect diet into which DIG-152 protein or Cry1Ab protein was incorporated.

|  | Insect | # larvae tested | $LC_{50}$ (95% CI) (μg/gm)[a] | RR[b] |
|---|---|---|---|---|
| DIG-152 | SCB | 505 | 0.03 (0.02-0.03) | 6.0 NS |
|  | rSCB | 506 | 0.18 (0.15-0.24) |  |
| Cry1Ab | SCB | 744 | 0.13 (0.08-0.20 | 142 S |
|  | rSCB | 440 | 18.46 (13.93-26.29 |  |

[a]The measure of larval mortality was defined as described in the text.
[b]Resistance ratios with a letter 'S" are Significant, while those with letters 'NS" are Not Significant at the 5% level based on lethal dose tests.

It is a feature of the DIG-152 protein of the subject invention that the growth of neonate sugarcane borer (*Diatraea saccharalis*) larvae is inhibited, or the larvae are killed, following ingestion of DIG-152 protein at levels similar to those of activated Cry1Ab protein which give the same biological response. It is a further feature of the DIG-152 protein that *Diatraea saccharalis* larvae that are resistant to the toxic effects of Cry1Ab protein are nonetheless susceptible to the toxic action of the DIG-152 protein.

EXAMPLE 5

Production of Rabbit Polyclonal and Mouse Monoclonal Antibodies Immunoreactive Against Chimeric Cry1Ca Proteins Antibodies were developed for the detection and quantitation of chimeric Cry1Ca proteins and variants of chimeric Cry1Ca proteins, for example, in extracts prepared from transgenic plants producing the proteins of the subject invention. Standard immunoblot preparation/analysis methods and ELISA methods were used to characterize the antibodies and for B.t. protein detection (for example, as taught in Coligan et al., 2007 and updates thereof).

Polyclonal Antibody Production.

The protein antigen used for polyclonal immunizations was a trypsin truncated core toxin prepared from DIG-152 protein produced in *P. fluorescens* cells as taught in Example 2. In addition, two peptides specific for the Cry1Ca core toxin segment were conjugated to Keyhole Limpet Hemocyanin and used as immunogens. The subject peptides correspond to amino acids 436-445 (VQRSGTPFLT; Cry1Ca436; SEQ ID NO:6) and amino acids 591-600 (SEQPLFGAGS; Cry1Ca591; SEQ ID NO:7) of SEQ ID NO:1. These peptide sequences were identified as being unique to Cry1Ca when the protein sequence of Cry1Ca was compared to sequences of several other class Cry1 B.t. proteins. Further, the peptides are expected be exposed on the surface of the native Cry1Ca protein.

Immunizations and serum collections were performed by standard procedures by contracted vendors. Polyclonal antibodies were obtained through Covance (Princeton, N.J.). New Zealand white rabbits were used to produce polyclonal antibodies against the trypsin activated DIG-152 protein. A 14 day cycle time was utilized between immunizations and serum collections. The dosing was started with Freund's complete adjuvant containing 0.5 mg of protein or conjugated peptide. Subsequent injections were prepared with incomplete Freund's adjuvant.

Sera from the two rabbits were combined to produce a single lot of protein A-purified antibody (termed DIG152RPC1) reactive with the Cry1Ca core toxin protein. As is well known to one skilled in the art of antibody characterization, polyclonal antibodies generated to an intact protein are generally not extremely specific and often will detect many epitopes on the immunizing protein as well as other, related proteins. Accordingly, immunoblot analysis revealed that DIG152RPC1 detects other Cry1-class B.t. toxins, specifically, trypsin activated Cry1Ab, Cry1Da, and Cry1Fa, and chymotrypsin activated Cry1Be and Cry1Ea. It is noted that in commercial settings, crop plants may produce other Cry1-class proteins, and thus DIG152RPC1 represents a useful reagent for detecting these proteins, including truncations and other forms of the proteins.

Two conjugated-peptide-specific lots of rabbit polyclonal antibody were developed for Cry1Ca. Two New Zealand White rabbits were used for each peptide and the sera were pooled for each peptide; resulting in one lot of peptide antibody for each of the two peptides. The immunizations and serum collections were performed by standard procedures, with 14 day cycle time between immunizations and serum collections. The final lot of serum was affinity purified with the corresponding peptide. Direct ELISA evaluation of both peptide-specific antibodies revealed that antibody against peptide Cry1Ca591 appears to specifically detect Cry1Ca when compared to reaction with other Cry1 class proteins, while the antibody against peptide Cry1Ca436 is not as specific (Table 6).

TABLE 6

Direct ELISA Optical Density readings obtained with two Cry1Ca peptide-specific antibodies after reaction with various Cry1 B.t. protein antigens when presented at 1 μg/mL.

|  | Cry1Ca | Cry1Ad | Cry1Fa | Cry1Be | Cry1Da | Cry2Aa | Cry1Ab | Cry1Ea |
|---|---|---|---|---|---|---|---|---|
| Anti-Cry1Ca591 | 1.36 | 0.32 | 0.27 | 0.27 | 0.3 | 0.2 | 0.51 | 0.23 |
| Anti-Cry1Ca436 | 0.39 | 0.32 | 0.41 | 0.42 | 0.54 | 0.32 | 0.81 | 0.38 |

Monoclonal Antibody Production.

Monoclonal antibodies were prepared by Open BioSystems/Thermo Fisher Scientific (Huntsville, Ala.). Mouse anti-Cry1Ca monoclonal antibody development used the trypsin truncated core toxin prepared from DIG-152 protein produced in *P. fluorescens* cells as described in Example 2. Immunization and cell line development were performed by standard antibody development methods in cell culture and not by ascites production methods. The monoclonal cell lines were developed per standard procedures by fusing the immunized mouse spleen cells with a compatible ND4 mouse myeloma cell line.

Direct binding ELISA screening identified mouse M4 sera as having significant specificity to the Cry1Ca protein (Table 7).

TABLE 7

End point titers of direct binding ELISA reaction of mouse M4 sera (immunized with trypsin-activated Cry1Ca) to several Cry1 class proteins.

| Antigen | Cry1Ca | Cry1Da | Cry1Ac | Cry1F | Cry1Be | Cry1Ab |
|---|---|---|---|---|---|---|
| End point titer | 312500 | 62500 | 500 | 12500 | <100 | 500 |

All M4 derived monoclonal lines were tested by direct binding ELISA for binding to Cry1Ca, Cry1Da, Cry1Ac, Cry1Fa, Cry1Be, and Cry1Ab. Lines M4-34 and M4-23, which demonstrated the ability to detect Cry1Ca [i.e. gave a high optical density (OD) reading], and did not detect the other Cry1 class proteins [i.e. gave zero or very low OD readings], are of particular interest (Table 8). Monoclonal antibodies from preferred Line M4-34 are referred to as antibody DIG152MabM4-34.

TABLE 8

Direct binding ELISA Optical Density readings of M4-derived monoclonal cell lines reacted with the target trypsin-activated Cry1Ca protein and non-target Cry1 class proteins.

| Antigen | Cry1Ca | Cry1Be | Cry1Ac | Cry1F | Cry1Ab | Cry1Da |
|---|---|---|---|---|---|---|
| Line M4-34 | 2.024 | 0.029 | 0.105 | −0.013 | −0.008 | 0.03 |
| Line M4-23 | 1.799 | 0.07 | 0.095 | 0.061 | 0.043 | 0.064 |

It is thus a subject of the present invention that monoclonal antibodies are provided that specifically recognize the truncated Cry1Ca B.t. protein.

EXAMPLE 6

Design of a Maize-Codon-Optimized Sequence Encoding the DIG-109 Protein

One skilled in the art of plant molecular biology will understand that multiple DNA sequences may be designed to encode a single amino acid sequence. A common means of increasing the expression of a coding region for a protein of interest is to tailor the coding region in such a manner that its codon composition resembles the overall codon composition of the host in which the gene is destined to be expressed. Guidance regarding the design and production of synthetic genes can be found in, for example, WO 1997/13402 and U.S. Pat. No. 5,380,831.

A DNA sequence having a maize codon bias was designed and synthesized to produce the DIG-109 chimeric insecticidal protein in transgenic monocot plants. A codon usage table for maize (*Zea mays* L.) was calculated from 706 protein coding sequences obtained from sequences deposited in GenBank (www.ncbi.nlm.nih.gov). A weighted-average maize codon set was calculated after omitting any redundant codon used less than about 10% of total codon uses for that amino acid. The Weighted Average representation for each codon was calculated using the formula:

$$\text{Weighted Average \% of } C1=1/(\%\ C1+\%\ C2+\%\ C3+\text{etc.})\times\%\ C1\times 100$$

where C1 is the codon in question and % C2, % C3, etc. represent the average % usage values of the remaining synonymous codons.

To derive a maize-codon-optimized DNA sequence encoding the 1164 amino acid DIG-109 protein of SEQ ID NO:5, codon substitutions to the native cry1Ca DNA sequence encoding the Cry1Ca core toxin segment were made such that the resulting DNA sequence had the overall codon composition of the maize-optimized codon bias table. In similar fashion, codon substitutions to the native cry1Ab DNA sequence encoding the Cry1Ab protoxin segment of SEQ ID NO:4 were made such that the resulting DNA sequence had the overall codon composition of the maize-optimized codon bias table. Further refinements to the sequences were made to eliminate undesirable restriction enzyme recognition sites, potential plant intron splice sites, long runs of A/T or C/G residues, and other motifs that might interfere with RNA stability, transcription, or translation of the coding region in plant cells. Other changes were made to introduce desired restriction enzyme recognition sites, and to eliminate long internal Open Reading Frames (frames other than +1). These changes were all made within the constraints of retaining approximately the maize-biased codon composition. A complete maize-codon-optimized sequence encoding the DIG-109 protein is disclosed as SEQ ID NO:8. Synthesis of a DNA fragment corresponding to SEQ ID NO:8 was performed by a commercial vendor (DNA2.0, Menlo Park, Calif.).

EXAMPLE 7

Construction of Plant Transformatin Vectors Containing Plant-Expressible Genes Encoding DIG-109 Proteins The *Agrobacterium* superbinary system (Japan Tobacco, Tokyo, JP) is conveniently used for transformation of monocot plant hosts. The superbinary system employs the pSB11 shuttle vector plasmid which contains the sequences for the Right T-DNA border repeat (RB) and Left T-DNA border repeat (LB) separated by multiple cloning sites. A derivative of pSB11 (called pDAB7691) was prepared by standard DNA cloning methods. Plasmid pDAB7691 contains the maize-optimized DIG-109 coding sequence (CDS; i.e., SEQ ID NO:8) under the transcriptional control of the maize ubiquitin) promoter with associated intron1 (U.S. Pat. No. 5,510,474) and the maize Per5 3' Untranslated Region (3' UTR) (U.S. Pat. No. 7,179,902). Further, pDAB7691 contains a plant selectable marker gene comprising the Dow AgroSciences DSM2 CDS (WO 2008/070845 A2) under the transcriptional control of the rice actin1 promoter with associated intron1 (U.S. Pat. No. 5,641,876) and the maize Lipase 3' UTR (U.S. Pat. No. 7,179,902). The physical arrangement of the components of the pDAB7691 T-region is conveniently illustrated as:

RB>maize Ubi1 promoter:DIG-109 CDS:maize Per5 YUTR>rice Act1 promoter:DSM2CDS:maize Lip 3'UTR>LB A second derivative of pSB11 (called pDAB100276) was prepared by standard DNA cloning methods. Plasmid pDAB100276 contains the maize-optimized DIG-109 coding sequence (CDS; i.e., SEQ ID NO:8) under the transcriptional control of the maize ubiquitin1 promoter with associated intron1 and the maize Per5 3' UTR. Further, pDAB100276 contains a plant selectable marker gene comprising the Dow AgroSciences AAD1 CDS (US Patent Application No. 20090093366), under the transcriptional control of the maize ubiquitin1 promoter with associated intron1 and the maize Lipase 3' UTR. The physical arrangement of the components of the pDAB100276 T-region is conveniently illustrated as:

RB>maize Ubi1 promoter:DIG-109 CDS: maize Per5 3' UTR>maize Ubi1 promoter:AA D-1 CDS:maize Lip 3' UTR>LB To prepare for *Agrobacterium* transformation, cells of *Escherichia coli* cloning strain DH5a harboring plasmid pDAB7691 or plasmid pDAB100276 were grown at 37° overnight on LB agar medium (g/L: Bacto Tryptone, 10; Bacto Yeast Extract, 5; NaCl, 10; agar, 15) in containing Spectinomycin (100 µg/mL). Strain DH5a cells containing the conjugal mobilizing plasmid pRK2013 were grown on LB agar containing Kanamycin (50 µg/mL). After incubation the plates were placed at 4° to await the availability of the *Agrobacterium tumefaciens* strain LBA4404 containing plasmid pSB1.

EXAMPLE 8

*Agrobacterium* Transformation for Generation of Superbinary Vectors

The *Agrobacterium* superbinary system, which employs *Agrobacterium tumefaciens* strain LBA4404 containing plasmid pSB1, is conveniently used for transformation of monocot plant hosts. Methodologies for constructing and validating superbinary vectors are well established as provided in the Operating Manual for pSB1 (Japan Tobacco). Standard microbiological and molecular biological methods were used to generate and validate the superbinary plasmid pDAS5162, which is a cointegrant plasmid comprising plasmids pSB1 and pDAB7691, and superbinary plasmid pDAS5848, which is a cointegrant plasmid comprising plasmids pSB1 and pDAB100276.

EXAMPLE 9

Production of DIG-109 Protein in Maize Plants

*Agrobacterium*-Mediated Transformation of Maize Seeds from a Hi-II F1 cross (Armstrong et al., 1991) were planted into 5-gallon-pots containing a mixture of 95% Metro-Mix 360 soilless growing medium (Sun Gro Horticulture, Bellevue, Wash.) and 5% clay/loam soil. The plants were grown in a greenhouse using a combination of high pressure sodium and metal halide lamps with a 16 hr light:8 hr dark photoperiod. Controlled sib-pollinations were performed to obtain immature F2 embryos for transformation. Maize ears were harvested at approximately 8-10 days post-pollination when immature embryos were between 1.0 mm and 2.0 mm in size.

Infection and Co-Cultivation.

Maize ears were dehusked and surface sterilized by scrubbing with liquid soap, immersing in 20% commercial bleach (containing 5% sodium hypochlorite) for about 20 minutes, then rinsing three times with sterile water. A suspension of *Agrobacterium tumefaciens* cells containing pDAS5162, a superbinary vector harboring a gene encoding the DIG-109 protein and containing the DSM2 plant selectable marker gene, was prepared by transferring 1 or 2 loops of bacteria [grown for 2-3 days at 28° on YEP solid medium (g/L: Bacto Yeast Extract, 10; Bacto Peptone, 10; NaCl, 5; agar, 15) containing 100 mg/L Spectinomycin, 10 mg/L Tetracycline, and 250 mg/L Streptomycin] into 5 mL of liquid infection medium [LS Basal Medium (Linsmaier and Skoog, 1965), N6 vitamins (Chu et al., 1975), 1.5 mg/L 2,4-Dichlorophenoxyacetic acid (2,4-D), 68.5 g/L sucrose, 36.0 g/L glucose, 6 mM L-proline, pH 5.2] containing 100 µM acetosyringone.

Alternatively, a suspension of *Agrobacterium tumefaciens* cells containing pDAS5848, a superbinary vector harboring a gene encoding the DIG-109 protein and containing the AAD-1 plant selectable marker gene, was prepared by transferring 1 or 2 loops of bacteria grown as above into 5 mL of liquid infection medium containing 100 to 200 µM acetosyringone.

In both cases, the solution was vortexed until a uniform suspension was achieved, and the concentration was adjusted to a final density of 200 Klett units using a Klett-Summerson colorimeter with a purple filter (for pDAS5162 transformations), or to an optical density of 1.2 at 550 nm (for pDAS5848 transformations). Immature embryos were isolated directly into a microcentrifuge tube containing 2 mL of the infection medium. The medium was removed and replaced with 1 mL of the *Agrobacterium* solution and the *Agrobacterium*/embryo solution was incubated for 5 to 10 minutes at room temperature. Embryos were then transferred to cocultivation medium [LS Basal Medium, N6 vitamins, 1.5 mg/L 2,4-D, 30.0 g/L sucrose, 6 mM L-proline, 0.85 mg/L AgNO3, 2.8 g/L Gellan gum (PhytoTechnology Laboratories, Lenexa, Kans.), pH 5.8] containing 100 µM acetosyringone (for pDAS5162 transformants) or containing 100 to 200 µM acetosyringone (for pDAS5848 transformants), and cocultivated for 3-4 days at 20° in the dark.

After cocultivation, the embryos were transferred to resting medium containing MS salts and vitamins, 6 mM L-proline, 100 mg/L myo-inositol, 500 mg/L MES, 30 g/L sucrose, 1.5 mg/L 2,4-D, 0.85 mg/L AgNO$_3$, 250 mg/L Cefotaxime, 2.8 g/L Gellan gum, pH 5.8. Approximately 7 days later, embryos were transferred to the same medium supplemented with 3 mg/L Bialaphos (for pDAS5162 transformants) or supplemented with 100 nM haloxyfop (for pDAS5848 transformants) (selection medium). Transformed isolates were identified after approximately 8 weeks and were bulked up by transferring to fresh selection medium at 2-week intervals for regeneration and analysis.

Regeneration and Seed Production.

For regeneration, the cultures were transferred to "28" induction medium (MS salts and vitamins, 30 g/L sucrose, 5 mg/L Benzylaminopurine, 0.25 mg/L 2,4-D, 250 mg/L Cefotaxime, 2.5 g/L Gellan gum, pH 5.7) supplemented with 3 mg/L Bialaphos (for pDAS5162 transformants) or supplemented with 100 nM haloxyfop (for pDAS5848 transformants). Incubation was for 1 week under low-light conditions (14 µm$^{-2}$ s$^{-1}$), then 1 week under high-light conditions (approximately 89 µEm$^{-2}$ s$^{-1}$). Tissues were subsequently transferred to "36" regeneration medium (same as induction medium except lacking plant growth regulators). When plantlets were 3-5 cm in length, they were transferred to glass culture tubes containing SHGA medium [(Schenk and Hildebrandt (1972) salts and vitamins; PhytoTechnologies Labr.), 1.0 g/L myo-inositol, 10 g/L sucrose and 2.0 g/L Gellan gum, pH 5.8] to allow for further growth and development of the shoot and roots. Plants were transplanted to the same soil mixture as described earlier and grown to flowering in the greenhouse. Controlled pollinations for seed production were conducted.

Those skilled in the art of maize transformation will understand that other methods are available for maize transformation and for selection of transformed plants when other plant expressible selectable marker genes (e.g. herbicide tolerance genes) are used.

EXAMPLE 10

Biochemical Analysis and Insect Bioassays of Maize Plants Producing DIG-109 Protein The production of DIG-109 protein in transgenic maize plants was examined in proteins extracted from leaves of young plants (TO generation). Two 6 mm diameter maize leaf disks were placed in a sample tube from a deep well 96 cluster tube box (Costar Cat#3957) and frozen at −80° until day of analysis. At that time, two 4.5 mm zinc-coated Daisy™ BB's were added to each (frozen) tube, along with 200µ of extraction buffer comprised of PBS (Phosphate Buffered Saline; Fisher Cat# BP665-1) plus 0.05% Tween 20. Each tube was capped and the box was placed in a bead mill (Kleco™ 4-96 Pulverizer; Garcia Manufacturing, Visalia, Calif.) at maximum setting for three minutes. The pulverized samples were centrifuged for 5 minutes at 2,500×g and the supernatant containing soluble proteins was used in the immunoassays.

Immunoblot analyses of extracted maize leaf proteins revealed that the DIG152RPC1 polyclonal antibody doe's not cross react with proteins extracted from leaves of nontransgenic plants. In extracts of plants transformed with pDAS5162, several protein species were detected by the DIG152PRC1 antibody. At least four major immunoreactive bands were usually detected. In many cases, an abundant protein species was seen that migrated with a mobility corresponding to a protein of approximately 70 kDa. The other major protein species had molecular sizes estimated to be 65 kDa, the same as that of the trypsin limit peptide of DIG-152 prepared from Dpf108 in Example 2), 60 kDa, and 55 kDa. When pDAS5162 transgenic maize leaf extracts were examined by immunoblot using a DIG-152 polyclonal antibody, in some plants the 60 kDa and 55 kDa species were the most abundant. With either antibody, only a few plants were found to have the full length DIG-109 (130 kDa) protein, and, when found, it was present as a minor species.

It is apparent that, although the transgene introduced into maize via transformation with pDAS5162 encodes the full-length DIG-109 protein, proteolytic activity within the maize cells processes the nascent protein to an abundance of stable smaller molecular weight species.

The insect toxicity of leaves harvested from independently isolated transgenic maize plants transformed with the pDAS5162 construct was tested in vitro using neonate larvae of fall armyworm (FAW, *Spodoptera frugiperda* (J. E. Smith)) and Cry1F-resistant FAW (rFAW) larvae. FAW eggs were obtained from a commercial insectary (Benzon), and rFAW eggs came from a proprietary population (Dow AgroSciences). Leaf segment samples were taken for insect bioassays from greenhouse-grown TO plants approximately 2 weeks after the plants were transplanted from the laboratory into the greenhouse. Two leaf pieces from each plant (each approximately 1 square inch) were placed into separate wells of a 32-well tray (CD International) on top of about 3 mL of solidified 2% agar. Eggs were hatched onto multi-species Lepidopteran diet (Southland Products) and neonate larvae were selected when less than 24 hours old. Approximately 10 larvae per leaf segment were carefully placed into each well using a camel hair paintbrush. Infested trays were sealed with the perforated lids supplied with the trays, then held at 28°, 40% RH, 16 hr light:8 hr dark for three days. Percent damage (% DAM) for each leaf piece was recorded at the conclusion of the test. Damage ratings were averaged and used to determine which plants had the least damage from each type of test insect. Tests were replicated several times for all insects.

Data were analyzed using JMP statistical software (SAS, Cary, N.C.), averaging the % DAM scores for each plant, for each insect type. The "Fit Y by X" model was used for one way ANOVA analyses. Tukey-Kramer means separation was used as needed to analyze for significant differences amongst the mean % DAM scores for each treatment. Comparisons were made to the % DAM scores obtained from control plants of similar age. Positive control plants were grown from seeds of the commercial Herculex I™ hybrid, which produces the Cry1Fa B.t. toxin. Negative controls (i.e. nontransformed plants) were represented by the Hi II and B104 lines, and a Herculex I™ Isoline (a non-Cry containing parent of the Herculex I™ hybrid).

FIG. 1 summarizes the results obtained in such insect bioassay tests. It is a surprising finding that there is a positive correlation between the production of DIG-109 in the transgenic leaves and the % DAM rating. For FAW, F=35.3; d.f.=1, 33; P<0.0001; $r^2$=0.52, and for rFAW, F=25.3; d.f.=1, 33; P<0.0001; $r^2$=0.43. It is a further surprising and novel finding that fall armyworm larvae that are resistant to intoxication by the Cry1Fa B.t. toxin are yet inhibited from feeding by the DIG-109 B.t. toxin.

It is understood that other insect pests of maize may be tested in similar fashion. These pests include, but are not limited to: *Agromyza parvicornis* (corn blot leafminer), *Agrotis ipsilon* (black cutworm), *Anticarsia gemmatalis* (velvetbean caterpillar), *Diatraea grandiosella* (southwestern corn borer), *Diatraea saccharalis* (sugarcane borer), *Elasmopalpus lignosellus* (lesser cornstalk borer), *Helicoverpa zea* (corn earworm), *Heliothis virescens*, (tobacco budworm), *Ostrinia nubilalis* (European corn borer), Cry1F-resistant *O. nubilalis*, *Plutella xylostella* (diamondback moth), Cry1-resistant *P. xylostella*, *Spodoptera exigua* (beet armyworm), and *Trichoplusia ni* (cabbage looper).

Transgenic maize plants transformed with pDAS5848 (TO generation) were also examined by insect bioassay and by immunoanalyses. The amount of DIG-109 protein in leaf extracts was quantitated using a commercially available Cry1C ELISA detection kit (Envirologix™, Portland, Mass.; Cat#AP007), and the level of DIG-109 protein detected was expressed as parts per million (ppm; 1 ppm represents 1 ng of DIG-109 protein per mg of total soluble protein in the extract). Feeding damage by FAW and rFAW was codified as follows: 0=no damage or a few pinhole feeding marks, 1=25% to 50% of leaf eaten, and 2=most all of leaf consumed or no leaf left. A protected plant is one whose damage score is 0.67 or lower.

The data in Table 9 show that there is a positive correlation between the presence of DIG-109 protein species detected by ELISA in the TO plants and control of feeding damage done by fall armyworm larvae in in vitro bioassays. The plant with the highest detected level of DIG-109 protein (plant 5848-005.4) had the lowest leaf feeding damage score. Leaves from plants with lower levels of detectable DIG-109 protein in the range of 190 to 230 ppm also suffered less feeding damage than was seen with leaves from the negative control plants (i.e. nontransformed controls B104 and Hi II), which had mean damage scores of 1.7 and 1.8. In all pDAS5848 leaves examined, the predominant DIG-109 protein species detected comprised a doublet of peptides of approximate size 60 kDa and 55 kDa.

TABLE 9

Levels of DIG-109 protein in pDAS5848-transformed transgenic maize leaf extracts and reduction of fall armyworm feeding damage.

| Plant Identifier | DIG-109 ppm | FAW Damage |
|---|---|---|
| 5848-005.4 | 680 | 0 |
| 5848-008.4 | 230 | 0.67 |
| 5848-001.3 | 220 | 1 |
| 5848-001.1 | 210 | 1 |
| 5848-001.2 | 190 | 0.33 |
| 5848-003.1 | 190 | 1 |
| 5848-003.2 | 190 | 0.67 |
| 5848-003.3 | 190 | 0.67 |
| Control Plants (Number Tested) | DIG-109 ppm | FAW Damage (SD[b]) |
| B104 (19) | NA[a] | 1.8 (0.5) |
| Hi II (20) | NA | 1.7 (0.5) |
| Herculex I ™ (20) | NA | 0.5 (0.6) |

[a]NA = Not Applicable;
[b]SD = Standard Deviation of the mean

It is thus a feature of the subject invention that the DIG-109 protein, when produced in maize plants, renders the plants resistant to feeding damage by fall armyworm larvae and Cry1F-resistant fall armyworm larvae.

EXAMPLE 11

Molecular Analysis of Maize Plants Producing DIG-109 Protein

Tissue Extraction.

Genomic DNA was isolated from leaves of pDAS5162- and pDAS5848-transformed T0 transgenic maize plants. Tissue samples were collected in 96-well collection plates (Qiagen, Cat. #19560) and lyophilized for 2 days. Tissue disruption was performed with a Klecko™ tissue pulverizer and tungsten beads essentially as disclosed in Example 10. For Hydrolysis Probe (HP) assays, genomic DNA was isolated in high throughput format using the DNeasy™ 96 Plant kit (Qiagen) according to manufacturer's suggested protocol. For Southern blot analysis, genomic DNA was isolated in high throughput format using the modifications of the CTAB DNA extraction protocol of Murray and Thompson (1980). Murray, M. G., Thompson, W. F. (1980) Rapid isolation of high molecular weight plant DNA. Nucl. Acids Res. 8:4321-4325.

Extracted DNA from either protocol was quantified with the Quant-IT Pico Green DNA assay kit (Molecular Probes, Invitrogen Catalog #P7589). In this procedure, 88 samples of unknowns were assayed in a 96 well format with the first column containing 2-fold serially diluted standards ranging from 20 ng/μL to 1.25 ng/μL, plus a buffer blank, a water blank and an empty well. Test DNA samples, 5 μL of 1:5 to 1:40 dilutions (depending on expected initial concentration), were then mixed with the appropriately diluted, buffered intercalating dye and incubated in a 105 μL reaction for ten minutes in the dark. Following incubation, the fluorescence was recorded using a Synergy2 plate reader (BioTek, Winooski, Vt.). Genomic DNA concentration was estimated from the standard curve calculated after background fluorescence corrections.

Southern Blot Preparation

Ten μg of genomic DNA from ten pDAS5848-transformed maize lines were digested with the restriction enzyme Bsm I overnight at 37°. Fragments of the digested DNA samples were separated via gel electrophoresis through a(SAS, Cary, N.C.) 1% agarose gels and transferred to nylon membrane (INYC00OI0 IMMOBILON-NY+, Millipore). The Southern blot was hybridized with a digoxigenin-labeled (DIG PCR Probe Synthesis Kit; Roche Applied Science, Indianapolis, Ind.) PCR-amplified probe corresponding to bases 251 to 630 of SEQ ID NO:8. The hybridization and detection were carried out according to the supplier's protocols. DNA from pDAS5848-transformed lines confirmed by Southern blot analysis to harbor a single copy of the DIG-109-encoding gene were used as reference controls for quantitative PCR copy number assays.

Hydrolysis Probe Assays

Transgene copy number determinations by Hydrolysis Probe (HP) assays were performed by real-time PCR using the LightCycler®480 system (Roche Applied Science). LightCycler® Probe Design Software v 2.0 was used to design assays to detect the DSM2 and AAD-1 selectable marker genes, the GLP1 (maize germin-like protein1; GenBank Accession AY394010) and INV (maize invertase; GenBank Accession U16123) reference genes, and the DIG-109-encoding gene. For amplification, LightCycler®480 Probes Master Mix was prepared at 1× final concentration in a 10 μL volume multiplex reaction containing 0.4 μM of each primer and 0.2 μM of each probe (sequences of the oligonucleotides and fluorescent labels are listed in Table 10). A two step amplification reaction was performed with an extension at 56° for 40 seconds with fluorescence acquisition. All samples were run in triplicate and the averaged Ct values were used for categorization of each sample.

TABLE 10

Oligonucleotides used in Hydrolysis Probe (HP) PCR assays.

| Name | Sequence | Function | SEQ ID NO: |
|---|---|---|---|
| ZGP3S | CCTGCTCCACTACCAGTACAA | HP PCR | SEQ ID NO: 9 |
| ZGP3A | GTCCAAGAAGGTGACCTTCTC | HP PCR | SEQ ID NO: 10 |
| TQZGP3 | 6FAM-AGATCACCGACTTTGCGCTCTTT-BHQ1 | Probe 6Fam | SEQ ID NO: 11 |
| DSM2S | CCTCCCTCTTTGACGCC | HP PCR | SEQ ID NO: 12 |
| DSM2A | AGCCACATCCCAGTAACGA | HP PCR | SEQ ID NO: 13 |
| DSM2FQ | CY5-CAGCCCAATGAGGCATGAGC-BHQ2 | Probe CY5 | SEQ ID NO: 14 |

TABLE 10-continued

Oligonucleotides used in Hydrolysis Probe (HP) PCR assays.

| Name | Sequence | Function | SEQ ID NO: |
|---|---|---|---|
| CRY1CaS | TGTGTTGAGGAGGAGGTC | HP PCR | SEQ ID NO: 15 |
| CRY1CaA | CCTTCTCTTCGTAAGCCG | HP PCR | SEQ ID NO: 16 |
| Cry1Ca | 6FAM-TCAAGAGGAGTACGAGGGCACTT-BHQ1 | Probe-6FAM | SEQ ID NO: 17 |
| AAD1S | TGTTCGGTTCCCTCTACCAA | HP PCR | SEQ ID NO: 18 |
| AAD1A | CAACATCCATCACCTTGACTGA | HP PCR | SEQ ID NO: 19 |
| AAD1[a] | CACAGAACCGTCGCTTCAGCAACA | Probe | SEQ ID NO: 20 |
| Y1CAS | TGTGTTGAGGAGGAGGTC | HP PCR | SEQ ID NO: 21 |
| Y1CAR | CCTTCTCTTCGTAAGCCG | HP PCR | SEQ ID NO: 22 |
| F6Y1CA | 6FAM-TCAAGAGGAGTACGAGGGCACTT-BHQ1 | Probe 6FAM | SEQ ID NO: 23 |
| IVF-Taq | TGGCGGACGACGACTTGT | HP PCR | SEQ ID NO: 24 |
| IVR-Taq | AAAGTTTGGAGGCTGCCGT | HP PCR | SEQ ID NO: 25 |
| IV-Probe | CY5-CGAGCAGACCGCCGTGTACTTCTACC-BHQ2 | Probe CY5 | SEQ ID NO: 26 |

[a]The AAD1 probe is a TaqMan® MGB probe supplied by ABI (Invitrogen)

The HP analysis for DSM2 was completed on 36 pDAS5162-transformed lines. A simple integration event, defined as 1-2 copies of the gene, was detected in 95% (34 events) of the samples.

The HP analysis for AAD-1 and DIG-109 was completed on 13 pDAS5848-transformed lines. A simple integration event was detected in 93% (12 lines) of the samples for AAD-1 and 54% (7 lines) for DIG-109. 54% of the lines (7 lines) contained simple integration events for both genes.

EXAMPLE 12

Biochemical Characterization of Maize DIG-109 Truncation Species

A more detailed analysis was performed on proteins extracted from leaves of a T0 maize plant transformed with pDAS5162. An immunoblot of the protein extract probed with the DIG152RPC1 polyclonal antibody revealed the presence of five DIG-109 protein species. Based on the relative mobilities of these peptides, the following identities were assigned: Species 1 corresponds to the full length DIG-109 (130 kDa) protein as designated in SEQ ID NO:5; Species 2 corresponds to a 70 kDa DIG-109 product. A peptide of the same mobility is found in extracts of bacterial cells expressing a gene encoding the full-length DIG-152 protein. The generation of these approximately 70 kDa fragments indicates the presence of predominant cleavage sites on the full length protein that are exposed to proteases found in both maize and bacteria. Species 3 corresponds in size to a trypsin limit peptide of DIG-152, as prepared in Example 2, with size of approximately 65 kDa; Species 4 corresponds to an approximately 60 kDa truncated DIG-109 product; Species 5 corresponds to an approximately 55 kDa truncated DIG-109 product. The peptides of approximately 70 kDa, 60 kDa and 55 kDa are further characterized in Example 14.

EXAMPLE 13

Design of Genes Encoding Variants of DIG-109 and Deletion of Domain I α-Helices

To improve the insecticidal properties of the DIG-109 protein, serial, step-wise deletions are made, each of which removes part of the N-terminus of the DIG-109 protein as disclosed in SEQ ID NO:5. The deletions remove part or all of α-helix 1 and part or all of α-helix 2 in Domain I, while maintaining the structural integrity of α-helix 3 through α-helix 7. We have deduced the beginnings and ends of α-helix 1, α-helix 2A, α-helix 2B, α-helix 3, and α-helix 4, and the locations of the spacer regions between them in Domain I of the Cry1Ca core toxin by comparing the Cry1Ca core toxin amino acid sequence with the amino acid sequence of the Cry1Aa protein (GenBank Accession No. AAA22353), for which the structure is known [RCBS Protein Structure Database Number: CRYIA(A); Grochulski et al., (1995)]. These locations are described in Table 1.

In designing coding sequences for the N-terminal deletion variants, an ATG start codon, encoding methionine, is inserted at the 5' end of the nucleotide sequence designed to express the deletion variant. For sequences designed for use in transgenic plants, it may be of benefit to adhere to the "N-end rule" of Varshaysky (1997). It is taught that some amino acids may contribute to protein instability and degradation in eukaryotic cells when displayed as the N-terminal residue of a protein. For example, data collected from observations in yeast and mammalian cells indicate that the N-terminal destabilizing amino acids are F, L, W, Y, R, K, H, I, N, Q, D, E and possibly P. While the specifics of protein degradation mechanisms may differ somewhat between organisms, the conservation of identity of N-terminal destabilizing amino acids seen above suggests that similar mechanisms may function in plant cells. For instance, Worley et al., (1998) found that in plants, the N-end rule includes basic and aromatic residues. It is a possibility that proteolytic cleavage by plant proteases near the start of α-helix 3 of subject B.t.

insecticidal proteins may expose a destabilizing N-terminal amino acid. Such processing may target the cleaved proteins for rapid decay and limit the accumulation of the B.t. insecticidal proteins to levels insufficient for effective insect control. Accordingly, for N-terminal deletion variants that begin with one of the destabilizing amino acids, applicants prefer to add a codon that specifies a G (glycine) amino acid between the translational initiation methionine and the destabilizing amino acid.

Deletions are designed as follows. This example utilizes the maize-codon-optimized full length 3492 bp DNA sequence (i.e. SEQ ID NO:8) encoding the full-length 1164 amino acid chimeric DIG-109 protein (i.e. SEQ ID NO:5) to illustrate the design principles with 65 specific variants. One skilled in the art will realize that other DNA sequences encoding all or an N-terminal portion of the Cry1Ca core toxin segment may be similarly manipulated to achieve the desired result. To devise the first deleted variant coding sequence, all of the bases that encode α-helix 1 including the codon for the valine residue near the beginning of α-helix 2A (i.e. V51 of the full length DIG-109 protein of SEQ ID NO:5), are removed. Thus, elimination of bases 1 through 153 of SEQ ID NO:8 removes the coding sequence for amino acids 1 through 51 of SEQ ID NO:5. Reintroduction of a translation initiating ATG (methionine) codon at the beginning (i.e. in front of the codon corresponding to amino acid 52 of the full length protein) provides for the deleted variant coding sequence comprising an open reading frame of 3342 bases which encodes a deleted variant DIG-109 protein comprising 1114 amino acids (i.e. methionine plus amino acids 52 to 1164 of the full-length DIG-109 protein). Serial, stepwise deletions that remove additional codons for a single amino acid corresponding to residues 52 through 91 of the full-length DIG-109 protein of SEQ ID NO:5 provide variants missing part or all of α-helix 2A and α-helix 2B. Thus a second designed deleted variant coding sequence requires elimination of bases 1 to 156 of SEQ ID NO:8, thereby removing the coding sequence for amino acids 1 through 52. Restoration of a functional open reading frame is again accomplished by reintroduction of a translation initiation methionine codon at the beginning of the remaining coding sequence, thus providing for a second deleted variant coding sequence having an open reading frame of 3339 bases encoding a deleted variant DIG-109 protein comprising 1113 amino acids (i.e. methionine plus amino acids 53 through 1164 of the full-length DIG-109 protein). The last designed deleted variant coding sequence requires removal of bases 1 through 273 of SEQ ID NO:8, thus eliminating the coding sequence for amino acids 1 through 91, and, after reintroduction of a translation initiation methionine codon, providing a deletion variant coding sequence having an open reading frame of 3222 bases which encodes a deletion variant DIG-109 protein of 1074 amino acids (i.e. methionine plus amino acids 92 through 1164 of the full-length DIG-109 protein). As exemplified, after elimination of the deletion sequence, an initiator methionine codon is added to the beginning of the remaining coding sequence to restore a functional open reading frame. Also as described, an additional glycine codon is to be added between the methionine codon and the codon for the instability-determining amino acid in the instance that removal of the deleted sequence leaves exposed at the N-terminus of the remaining portion of the full-length protein one of the instability-determining amino acids as provided above.

Table 11 describes specific variants designed in accordance with the strategy described above.

TABLE 11

Deletion variant protein sequences of the full-length DIG-109 protein of SEQ ID NO: 5.

| DIG-109 Deletion Variant | Residues added at NH$_2$ terminus | Residues of SEQ ID NO: 5 |
|---|---|---|
| 1 | M | 52-1164 |
| 2 | MG | 52-1164 |
| 3 | M | 53-1164 |
| 4 | M | 54-1164 |
| 5 | M | 55-1164 |
| 6 | M | 56-1164 |
| 7 | M | 57-1164 |
| 8 | MG | 57-1164 |
| 9 | M | 58-1164 |
| 10 | M | 59-1164 |
| 11 | M | 60-1164 |
| 12 | M | 61-1164 |
| 13 | MG | 61-1164 |
| 14 | M | 62-1164 |
| 15 | MG | 62-1164 |
| 16 | M | 63-1164 |
| 17 | MG | 63-1164 |
| 18 | M | 64-1164 |
| 19 | M | 65-1164 |
| 20 | MG | 65-1164 |
| 21 | M | 66-1164 |
| 22 | M | 67-1164 |
| 23 | M | 68-1164 |
| 24 | M | 69-1164 |
| 25 | M | 70-1164 |
| 26 | M | 71-1164 |
| 27 | MG | 71-1164 |
| 28 | M | 72-1164 |
| 29 | MG | 72-1164 |
| 30 | M | 73-1164 |
| 31 | MG | 73-1164 |
| 32 | M | 74-1164 |
| 33 | MG | 74-1164 |
| 34 | M | 75-1164 |
| 35 | M | 76-1164 |
| 36 | MG | 76-1164 |
| 37 | M | 77-1164 |
| 38 | MG | 77-1164 |
| 39 | M | 78-1164 |
| 40 | M | 79-1164 |
| 41 | MG | 79-1164 |
| 42 | M | 80-1164 |
| 43 | MG | 80-1164 |
| 44 | M | 81-1164 |
| 45 | MG | 81-1164 |
| 46 | M | 82-1164 |
| 47 | MG | 82-1164 |
| 48 | M | 83-1164 |
| 49 | MG | 83-1164 |
| 50 | M | 84-1164 |
| 51 | MG | 84-1164 |
| 52 | M | 85-1164 |
| 53 | MG | 85-1164 |
| 54 | M | 86-1164 |
| 55 | MG | 86-1164 |
| 56 | M | 87-1164 |
| 57 | MG | 87-1164 |
| 58 | M | 88-1164 |
| 59 | MG | 88-1164 (DIG-110) |
| 60 | M | 89-1164 |
| 61 | M | 90-1164 |
| 62 | MG | 90-1164 |
| 63 | M | 91-1164 |
| 64 | MG | 91-1164 |
| 65 | M | 92-1164 |

Additional nucleic acids encoding the DIG-109 protein variants described in Table 11 are designed in accordance with the general principles for synthetic genes intended for expression in plants, as taught in Example 6.

EXAMPLE 14

Design of Additional DIG-109 Protein Variants

As disclosed in Example 12, the initial translation product comprising the full length DIG-109 protein is processed to various degrees in plants, and one of the products corresponds in size to the 65 kDa trypsin truncated core toxin peptide. This core toxin is considered to be the activated form of the toxin that binds to receptors in the insect midgut and results in toxicity. Trypsins are endopeptidases that cleave proteins on the C-terminal side of arginine (R) or lysine (K) residues. Thus, the 65 kDa DIG-109 peptide seen in maize may correspond to the 65 kDa fragment generated by cleavage after residues R28 and R628 of SEQ ID NO:5 bp a maize trypsin-like protease. It is noted that this 65 kDa core toxin peptide may comprise amino acids 28 to 619 of the Cry1Ca core toxin segment of SEQ ID NO:1 and amino acids 1 to 9 of the Cry1Ab protoxin segment of SEQ ID NO:4. It is to be understood, however, that the precise C-terminus of the 65 kDa truncation product, or of other truncation products observed in the transgenic maize and discussed below, has not been experimentally determined. Thus, the designs of the DIG-109 variant proteins discussed herein are intended to be illustrative and other DIG-109 truncated variant proteins that retain insecticidal activity are within the scope of this invention.

The concentration of DIG-109 peptide products present in most transgenic maize plants was determined to be approximately 200 ppm. Thus, insufficient material is available for purification from the plant tissues on hand to determine the amino acid sequences of the DIG-109 peptides. Surrogate peptides that are similar in size to the truncated products detected in maize were generated by using different proteases to cleave full length DIG-152 protein.

Identity of the 70 kDa Peptide.

The SDS-PAGE profile of full length DIG-152 produced as inclusion bodies in *Pseudomonas fluorescens* (Pf) revealed a significant amount of a protein having an apparent molecular size of 70 kDa and which was relatively stable to trypsin treatment. Following purification from solubilized full length DIG-152 inclusion bodies by a combination of anion exchange and size exclusion chromatography, this peptide had identical mobility on SDS-PAGE as the approximately 70 kDa DIG-109 peptide detected in extracts from transgenic maize plants. Both peptides were recognized by a polyclonal antibody directed against DIG-152, and amino acid sequence analysis of the Pf-produced peptide identified MDNNP as the N-terminal sequence (residues 1 to 5 of DIG-109, SEQ ID NO:5). Thus the 70 kDa peptide contains the native N-terminus of the full length DIG-109 protein. Trypsin cleavage at the putative core toxin C-terminal cleavage site (R628), while leaving intact the first 28 residues that are characteristically removed from the DIG-109 protein by trypsin cleavage at R28 to generate the core toxin, generates a peptide (comprised of DIG-109 residues 1-628) with a calculated size of 70.5 kDa, nearly identical to the apparent molecular weight of the DIG-152 peptides isolated from Pf inclusion bodies and detected in transgenic maize plants. Thus, the identity of the 70 kDa protein is proposed to correspond to a truncated DIG-109 peptide comprised of amino acids 1-628.

Identities of the 60 kDa and 55 kDa peptides. The pDAS5162- and pDAS5848-transformed maize plants were found to also produce DIG-109-derived proteins of mobilities corresponding to 60 kDa and 55 kDa. Peptides of these sizes were produced experimentally by first cleaving full length DIG-152 protein with trypsin and subsequently treating the trypsin-cleaved products with chymotrypsin. [Treatment of full length DIG-152 protein with chymotrypsin alone resulted in multiple truncated products somewhat larger than 60 kDa.] The trypsin/chymotrypsin cleaved products were prepared in bulk and then purified by anion exchange chromatography followed by Superose 200 size exclusion chromatography. Three major peaks were observed in the size exclusion chromatography step, eluting at 12.5 mL, 18.3 mL, and 20 mL collected volumes. The first major peak (12.5 mL) contained high molecular weight (700 kDa to 1000 kDa) aggregates of DIG-152 proteins, and the third major peak (20 mL) contained excess chymotrypsin. The 12.5 mL fraction also contained bands having mobilities that corresponded to the 65 kDa and 60 kDa products of DIG-152; thus it appears that oligomerization or aggregation of DIG-152-derived peptides is reversible.

Proteins in the 18.3 mL peak, along with DIG-152 protein cleaved with trypsin only, were analyzed by SDS-PAGE under reducing and denaturing conditions. These proteins comprised two major species with mobilities corresponding to 60 kDa and 55 kDa. Smaller proteins of 14 kDa and 9 kDa were also observed and were identified as chymotrypsin that was apparently bound to the DIG-152 peptides during purification. In addition, a high molecular weight band with mobility corresponding to 240 kDa was observed. Proteins in this band were recognized by the DIG152RPC1 antibody, demonstrating that it was most likely an oligomer (tetramer) of the DIG-152 cleavage products.

Proteins in extracts from plants producing DIG-109 were separated by SDS-PAGE and then electroblotted onto nitrocellulose, along with samples of purified, trypsin cleaved DIG-152 and DIG-152 protein cleaved with trypsin then chymotrypsin. Bands corresponding to DIG-109 or DIG-152 peptides were visualized using enhanced chemiluminescence elicited by a combination of a primary DIG152RPC1 rabbit antibody and a secondary anti-rabbit horseradish peroxidase labeled antibody. The trypsin treated DIG-152 sample exhibited a single band at approximately 65 kDa mobility. The extract from plants producing DIG-109 peptides exhibited four bands: one with mobility corresponding to 130 kDa, (representing the full length DIG-109 protein), bands of mobilities corresponding to 60 kDa and 55 kDa, and a band of mobility corresponding to approximately 20 kDa. The 20 kDa cleavage product of DIG-109 was not further characterized. The DIG-152 protein that was trypsin and then chymotrypsin treated exhibited two bands that had mobilities corresponding to approximately 60 kDa and 55 kDa, and which co-migrated with the 60 kDa and 55 kDa bands seen in the plant extracts. There was also a high molecular weight band with mobility corresponding to about 240 kDa in the DIG-152 protein sample that was trypsin and then chymotrypsin treated.

Thus, the major cleavage products of DIG-109 that are produced in maize correspond in size to the two products that are obtained when full length DIG-152 protein is first cleaved with trypsin, then cleaved further with chymotrypsin. The first five N-terminal residues from the enzymatically-produced 60 kDa and 55 kDa peptides were both determined to be DAFLV (corresponding to residues 74 to 78 of the DIG-109 protein, SEQ ID NO:5). It is noted that such cleavage after W73 of the full length DIG-109 protein results in removal of α-helix1, α-helix2A and part of α-helix2B (Table 1).

It is further noted that, since both the 60 kDa and 55 kDa peptides have the same N-terminal sequence, the 5 kDa segment that is removed in the production of the smaller (55 kDa) peptide must represent further processing from the C-terminal end of the 60 kDa peptide.

The presumptive amino acid coordinates of the five major DIG-109 peptides produced in pDAS5162- and pDAS5848-transformed maize plants are summarized in Table 12. The precise C-termini of these Species were not determined. It is noted that trypsin cleavage of the 60 kDa Species 4 after R568 would generate a peptide of 56 kDa, (i.e. close to that of Species 5).

TABLE 12

Proposed identities of processed peptides derived from DIG-109 and DIG-152 proteins. Approximate C-termini positions were deduced from approximate MW on gels. Amino acid numbers are inclusive.

| D1G-109 or DIG-152 peptide | Residues of SEQ ID NO: 5 |
|---|---|
| Species 1 (130 kDa) | 1 to 1164 (calculated MW 131.7) |
| Species 2 (70 kDa) | 1 to 628 (calculated MW 70.59) |
| Species 3 (trypsin generated core; 65 kDa) | 28 to 628 (600 residues, calculated MW 67.4) |
| Species 4 (60 kDa) | 74 to 628 (555 residues, calculated MW 62.7) |
| Species 5 (55 kDa) | 74 to 568 (495 residues, calculated MW 56.1) |

Design of DIG-109 Truncation Variants.

As set forth in Table 1, α-helix1 through α-helix4 of the DIG-109 core toxin reside within the first 145 amino acids of the DIG-109 protein. Cleavage at the first potential site on the N-terminal end of the DIG-109 core toxin (R87 of DIG-109; R59 of the core toxin) would remove 59 amino acids from the DIG-109 core, and yield a protein having a molecular weight of 61.02 kDa, with α-helix 1, α-helix2A, and α-helix2B removed. Removal of α-helix I of Cry1Ab has been implicated in allowing the protein to bypass an initial binding to the cadherin receptor, resulting in the formation of an oligomer pre-pore structure prior to insertion into the insect midgut cell membranes, and ultimately resulting in pore formation. By analogy to those studies, it is predicted that removal of the N-terminal portion of the trypsin truncated DIG-109 core, resulting in loss of α-helix1, is a necessary step to allow the formation of oligomers and for binding to a secondary aminopeptidase N receptor leading to formation of a functional pore. Thus, cleavage of the DIG-109 protein in plants in such fashion could result in a DIG-109 toxin peptide that upon ingestion by insects bypasses the requirement for binding to a cadherin receptor. Such an effect has been shown to result in overcoming resistance to Bt protein intoxication in insects having mutant cadherin receptor proteins.

The smaller peptides (60 kDa and 55 kDa) found in the pDAS5162 and pDAS5848 transgenic maize plants may represent the products of further cleavage by a trypsin-like protease. Since these peptides are only 5 kDa to 10 kDa smaller than the 65 kDa core peptide, such further cleavage would remove less than a total of approximately 80 residues from either end of the core toxin. Within the first 130 residues from the N-terminus of the DIG-109 protein, potential trypsin cleavage sites are located at R28 (R-1 of the core toxin), R87 (R59 of the core toxin), R93 (R65 of the core toxin), KI15 (K87 of the core toxin), K122 (K94 of the core toxin), R127 (R99 of the core toxin), and R129 (R101 of the core toxin). Within the final 100 amino acids of the C-terminus of the core toxin, potential trypsin cleavage sites are located at 8530 (R502 of the core toxin), R533 (R505 of the core toxin), K557 (K529 of the core toxin), R568 (R540 of the core toxin), R571 (R543 of the core toxin), R582 (R554 of the core toxin), and K610 (K582 of the core toxin).

Using the locations of the above identified potential protease cleavage sites as a guide, DNA sequences derived from the maize-optimized DIG-109 coding sequence disclosed in SEQ ID NO:8 were designed to encode genetically truncated DIG-109 protein variants. The guidelines for addition of 5' terminal methionine and glycine codons to initiate the truncated coding regions as disclosed in Example 13 were also employed for these constructs. The first such embodiment, DIG-110, disclosed as SEQ ID NO:27, comprises amino acids 88 to 1164 of the DIG-109 protein, with an N-terminal addition of methionine and glycine. A maize optimized DNA sequence encoding DIG-110 is disclosed as SEQ ID NO:28. A second embodiment, DIG-111, disclosed as SEQ ID NO:29, comprises amino acids 88 to 628 of the DIG-109 protein, with an N-terminal addition of methionine and glycine. A maize optimized DNA sequence encoding DIG-111 is disclosed as SEQ ID NO:30. A third embodiment, DIG-112, disclosed as SEQ ID NO:31, comprises amino acids 123 to 1164 of the DIG-109 protein, with an N-terminal addition of methionine and glycine. A maize optimized DNA sequence encoding DIG-112 is disclosed as SEQ ID NO:32. A fourth embodiment, DIG-113, disclosed as SEQ ID NO:33, comprises amino acids 123 to 628 of the DIG-109 protein, with an N-terminal addition of methionine and glycine. A maize optimized DNA sequence encoding DIG-113 is disclosed as SEQ ID NO:34. A fifth embodiment, DIG-114, disclosed as SEQ ID NO:35, comprises amino acids 1 to 582 of the DIG-109 protein. A maize optimized DNA sequence encoding DIG-114 is disclosed as SEQ ID NO:36.

It is to be noted that the DIG-110 and DIG-112 proteins include the Cry1Ab protoxin segment disclosed in SEQ ID NO:4. It is thought that this C-terminal protoxin segment might function in some instances to stabilize the protein in the plant or make it more soluble. Cleavage at the trypsin site at R543 of DIG-110, thus removing most of the protoxin segment, would generate a peptide of calculated size 61.2 kDa, a size that is very close to that of the 60 kDa DIG-109 truncated peptide observed in the pDAS5162- and pDAS5848-transformed maize plants. The DIG-111 protein (which lacks all of the Cry1Ab protoxin segment except for the first 9 amino acids) comprises the segment of DIG-110 that would result from such cleavage (i.e. amino acids 1 to 543 of DIG-110; calculated size of 61.2 kDa).

Similarly, cleavage at the analogous R508 site of DIG-112 would generate a peptide of calculated size 57.2 kDa, a size that is very close to that of the 55 kDa DIG-109 peptide observed in the pDAS5162- and pDAS5848-transformed maize plants. The DIG-113 protein (which lacks all of the Cry1Ab protoxin segment except for the first 9 amino acids) comprises the segment of DIG-112 that would result from such cleavage (i.e. amino acids 1 to 508 of DIG-112; calculated size of 57.2 kDa).

The DIG-114 protein retains amino acids 1 to 28 of the DIG-109 protein (these residues may be enzymatically removed in plant cells or in the insect midgut) and terminates at the potential trypsin cleavage site at R582 of the DIG-109 protein. Thus this DIG-109 variant may exist as a 65.7 kDa protein, or as a 62.6 peptide, depending on whether or not the N-terminal 28 amino acids are removed in vivo.

Additional maize optimized coding sequences may be designed to encode further DIG-109 protein variants by the principles disclosed herein.

EXAMPLE 15

Construction of Expression Plasmids Encoding DIG-109 and DIG-109 Variant Proteins and Expression in *Pseudomonas*

Standard cloning methods [as described in, for example, Sambrook et al., (1989) and Ausubel et al., (1995), and updates thereof] were used in the construction of *Pseudomonas fluorescens* (Pf) expression constructs engineered to produce the DIG-109 protein or a DIG-110, DIG-111, DIG-112, DIG-113, or DIG-114 protein (collectively referred to as DIG-109 variant proteins). Protein production was performed in *Pseudomonas fluorescens* strain MB214 (a derivative of strain MB101; *P. fluorescens* biovar I), having an insertion of a modified lac operon as disclosed in U.S. Pat. No. 5,169,760. The basic cloning strategy entailed subcloning a DNA fragment encoding DIG-109 or a DIG-109 variant protein into plasmid pDOW1169, whereby it is placed under the expression control of the Ptac promoter and the rrnBT1T2 terminator from plasmid pKK223-3 (PL Pharmacia, Milwaukee, Wis.). pDOW1169 is a medium copy plasmid with the RSF1010 origin of replication, a pyrF gene, and a ribosome binding site preceding the restriction enzyme recognition sites into which DNA fragments containing protein coding regions may be introduced (US Patent Application No. 20080193974). The expression plasmid was transformed by electroporation into DC454 (a near wild-type *P. fluorescens* strain having mutations ΔpyrF and lsc::lacI$^{Q1}$), or its derivatives, recovered in SOC-Soy hydrolysate medium, and plated on selective medium (M9 glucose agar lacking uracil, Sambrook et al., supra). Details of the microbiological manipulations are available in Squires et al., (2004), US Patent Application No. 20060008877, US Patent Application No. 20080193974, and US Patent Application No. 20080058262, incorporated herein by reference. Colonies were first screened by PCR and positive clones were then analyzed by restriction digestion of miniprep plasmid DNA. Plasmid DNA of selected clones containing inserts was sequenced by contract with a commercial sequencing vendor such as MWG Biotech (Huntsville, Ala.). Sequence data was assembled and analyzed using the Sequencher™ software (Gene Codes Corp., Ann Arbor, Mich.).

Growth and Expression Analysis in Shake Flasks

Production of DIG-109 protein or DIG-109 variant proteins for characterization and insect bioassay was accomplished by shake-flask-grown *P. fluorescens* strains containing appropriate expression plasmids. Production of DIG-109 protein or DIG-109 variant proteins was driven by the Ptac promoter and was conducted as described previously in U.S. Pat. No. 5,527,883. Expression was induced by addition of isopropyl-β-D-1-thiogalactopyranoside (IPTG) after an initial incubation of 24 hours at 30° with shaking. Cultures were sampled at the time of induction and at various times post-induction. Cell density was measured by optical density at 600 nm ($OD_{600}$). At each sampling time, the cell density of samples was adjusted to $OD_{600}$=20 and 1 mL aliquots were centrifuged at 14000×g for five minutes. The cell pellets were frozen at −80°.

EXAMPLE 16

Cell Fractionation and SDS-PAGE Analysis of Shake Flask Samples of *Pseudomonas* Production of DIG-109 and DIG-109 Variant Proteins Soluble and insoluble fractions from frozen shake flask cell pellet samples are generated using EasyLyse™ Bacterial Protein Extraction Solution (EPICENTRE® Biotechnologies, Madison, Wis.). The methods and guidelines as disclosed in Example 2 are employed

EXAMPLE 17

Insecticidal Activity of DIG-109 Variant Proteins Produced in *Pseudomonas fluorescens*

Insecticidal activity of the DIG-109 variant proteins is demonstrated on Lepidopteran species including the European corn borer (ECB; *Ostrinia nubilalis* (Hübner)), cry 1F-resistant ECB (rECB), corn earworm (CEW; *Helicoverpa zea* (Boddie)), black cutworm (BCW; *Agrotis ipsilon* (Hufnagel)), fall armyworm (FAW, *Spodoptera frugiperda* (J. E. Smith)), Cry1F-resistant FAW (rFAW), southwestern corn borer (SWCB, *Diatraea grandiosella*), sugarcane borer (SCB; *Diatraea saccharalis*) and Cry1Ab-resistant SCB (rSCB).

The methods, guidelines and data analyses disclosed in Example 3 and Example 4 are followed.

EXAMPLE 18

Construction of Plant Transformation Vectors Containing Plant-Expressible Genes Encoding DIG-109 Variant Proteins The *Agrobacterium* superbinary system (Japan Tobacco, Tokyo, JP) is conveniently used for transformation of monocot plant hosts. Construction of plant expression vectors, and the generation of superbinary plasmids and their validation are performed by methods as disclosed in Example 7 and Example 8. The physical arrangements of the T-DNA components of the pSB11 derivative plasmids are conveniently illustrated as:

RB>maize Ubi1 promoter:DIG-109 variant CDS:maize Per5 3'UTR>rice Act1 promoter:DSM2 CDS:maize Lip 3'UTR>LB, or RB>maize Ubi1 promoter:DIG-109 variant CDS: maize Per5 3' UTR>maize Ubi1 promoter:AAD-1 CDS:maize Lip 3' UTR>LB

EXAMPLE 19

Production of DIG-109 Protein Variants in Maize Plants

*Agrobacterium*-Mediated Transformation of Maize

Transgenic maize plants that produce DIG109 variant proteins are generated by the methods disclosed in Example 9.

Those skilled in the art of maize transformation will understand that other methods are available for maize transformation and for selection of transformed plants when other plant expressible selectable marker genes (e.g. herbicide tolerance genes) are used.

EXAMPLE 20

Biochemical and Molecular Analysis and Insect Bioassay of Transgenic Maize Plants Expressing Genes that Encode DIG-109 Variant Proteins Biochemical characterization of the DIG-109 variant proteins produced by transgenic maize plants that harbor and express genes encoding DIG-109 variant proteins is conducted by the methods and reagents of Example 10 and Example 12. Transgene analysis of the genes encoding DIG-109 variant proteins is performed according to methods and reagents disclosed in Example 11. Insect bioassay of leaf pieces derived from transgenic maize plants that harbor and express genes encoding DIG-109 variant proteins is conducted by the methods disclosed in Example 10.

The invention claimed is:

1. A Cry1Ca variant protein that has insecticidal activity, in which all or part of N-terminal alpha helices 1, 2A, and/or 2B of a corresponding wild-type Cry1Ca are deleted, wherein said protein is at least 99% identical to a sequence selected from the group consisting of: SEQ ID NO: 3 and SEQ ID NO:5.

2. The variant protein of claim 1 wherein deletions remove all of α-helix 1 and all or part of α-helix 2 in Domain I, said protein comprising α-helices 3 through 7.

3. The variant protein of claim 1 wherein said deletions improve insecticidal activity of insecticidal protein DIG-109, wherein said deletions initiate before α-helix 2A start and terminate after α-helix 2B end but do not extend into α-helix 3.

4. The variant protein of claim 1 wherein said deletions improve insecticidal activity of insecticidal protein DIG-152, wherein said deletions initiate before α-helix 2A start and terminate after α-helix 2B end but do not extend into α-helix 3.

5. The variant protein of claim 1 wherein N-terminal deletions begin with at least one destabilizing amino acids, and said protein comprises an added codon that specifies a glycine amino acid between a translational initiation methionine and the destabilizing amino acid.

6. The variant protein of claim 1 wherein said protein lacks C-terminal protoxin sequence.

7. The protein of claim 1, wherein said protein has improved activity against an insect compared to the wild-type Cry1Ca protein.

8. The protein of claim 7 wherein said insect is selected from the group consisting of fall armyworm and sugarcane borer.

9. The protein of claim 1, wherein said protein is at least 99% identical to SEQ ID NO:3.

10. The protein of claim 1, wherein said protein is at least 99% identical to SEQ ID NO:5.

11. The protein of claim 9, wherein said protein comprises SEQ ID NO:3.

12. The protein of claim 10, wherein said protein comprises SEQ ID NO:5.

* * * * *